(12) United States Patent
Garvey

(10) Patent No.: US 8,846,674 B2
(45) Date of Patent: *Sep. 30, 2014

(54) NITRIC OXIDE ENHANCING PROSTAGLANDIN COMPOUNDS, COMPOSITIONS AND METHODS OF USE

(75) Inventor: David S. Garvey, Dover, MA (US)

(73) Assignee: Nicox, S.A., Sophia Antipolis (FR)

( * ) Notice: Subject to any disclaimer, the term of this patent is extended or adjusted under 35 U.S.C. 154(b) by 0 days.

This patent is subject to a terminal disclaimer.

(21) Appl. No.: 13/275,768

(22) Filed: Oct. 18, 2011

(65) Prior Publication Data

US 2012/0034321 A1 Feb. 9, 2012

Related U.S. Application Data

(62) Division of application No. 12/294,642, filed as application No. PCT/US2007/006749 on Mar. 19, 2007, now Pat. No. 8,067,414.

(60) Provisional application No. 60/786,689, filed on Mar. 29, 2006.

(51) Int. Cl.

| A61K 31/5377 | (2006.01) |
| A61K 31/4523 | (2006.01) |
| A61K 31/41 | (2006.01) |
| A61K 31/4245 | (2006.01) |
| A61K 31/4035 | (2006.01) |
| A61K 31/535 | (2006.01) |
| C07D 233/02 | (2006.01) |
| C07D 271/08 | (2006.01) |
| C07D 263/06 | (2006.01) |
| C07D 265/06 | (2006.01) |
| C07D 211/94 | (2006.01) |
| C07D 209/46 | (2006.01) |
| C07D 207/46 | (2006.01) |

(52) U.S. Cl.
CPC ............ *C07D 271/08* (2013.01); *C07D 233/02* (2013.01); *C07D 263/06* (2013.01); *C07D 265/06* (2013.01); *C07D 211/94* (2013.01); *C07D 209/46* (2013.01); *C07D 207/46* (2013.01)
USPC ........ 514/236.2; 514/326; 514/361; 514/364; 514/414; 514/422

(58) Field of Classification Search
None
See application file for complete search history.

(56) References Cited

U.S. PATENT DOCUMENTS

| 4,868,179 A | 9/1989 | Cohn |
| 5,284,872 A | 2/1994 | Sandrock et al. |
| 5,344,991 A | 9/1994 | Reitz et al. |
| 5,380,738 A | 1/1995 | Norman et al. |
| 5,380,758 A | 1/1995 | Stamler et al. |
| 5,393,790 A | 2/1995 | Reitz et al. |
| 5,409,944 A | 4/1995 | Black et al. |
| 5,428,061 A | 6/1995 | Sandrock et al. |
| 5,434,178 A | 7/1995 | Talley et al. |
| 5,436,265 A | 7/1995 | Black et al. |
| 5,466,823 A | 11/1995 | Talley et al. |
| 5,474,995 A | 12/1995 | Ducharme et al. |
| 5,510,368 A | 4/1996 | Lau et al. |
| 5,536,752 A | 7/1996 | Ducharme et al. |
| 5,550,142 A | 8/1996 | Ducharme et al. |
| 5,552,422 A | 9/1996 | Gauthier et al. |
| 5,604,253 A | 2/1997 | Lau et al. |
| 5,604,260 A | 2/1997 | Guay et al. |
| 5,625,083 A | 4/1997 | Bezuglov et al. |
| 5,639,780 A | 6/1997 | Lau et al. |
| 5,650,447 A | 7/1997 | Keefer et al. |
| 5,661,129 A | 8/1997 | Feelisch et al. |
| 5,703,073 A | 12/1997 | Garvey et al. |
| 5,703,758 A | 12/1997 | Snyder et al. |
| 5,807,847 A | 9/1998 | Thatcher et al. |
| 5,883,122 A | 3/1999 | Thatcher et al. |
| 5,910,316 A | 6/1999 | Keefer et al. |
| 5,932,598 A | 8/1999 | Talley et al. |
| 6,133,272 A | 10/2000 | Garvey et al. |
| 6,172,068 B1 | 1/2001 | Garvey et al. |
| 6,177,428 B1 | 1/2001 | Garvey et al. |
| 6,197,778 B1 | 3/2001 | Garvey et al. |
| 6,197,782 B1 | 3/2001 | Garvey et al. |
| 6,211,179 B1 | 4/2001 | Garvey et al. |
| 6,221,881 B1 | 4/2001 | Garvey et al. |
| 6,232,321 B1 | 5/2001 | Garvey et al. |

(Continued)

FOREIGN PATENT DOCUMENTS

| EP | 0 574 726 | 12/1993 |
| EP | 0 683 159 | 11/1995 |

(Continued)

OTHER PUBLICATIONS

Brideau et al. "A human whole blood assay for clinical evaluation of biochemical efficacy of cyclooxygenase inhibitors," Inflamm. Res. 45: 68-74 (7 pages) (1996).

(Continued)

*Primary Examiner* — Alicia L Otton

(74) *Attorney, Agent, or Firm* — Wilmer Cutler Pickering Hale and Dorr LLP

(57) ABSTRACT

The invention provides methods for treating ophthalmic disorders comprising at least one nitric oxide enhancing prostaglandin compound or a pharmaceutically acceptable salt thereof, and, optionally, at least one nitric oxide enhancing compound and/or at least one therapeutic agent. The nitric oxide enhancing prostaglandin compounds comprise at least one heterocyclic nitric oxide donor group and/or at least one nitroxide group.

6 Claims, No Drawings

(56) References Cited

U.S. PATENT DOCUMENTS

| | | |
|---|---|---|
| 6,232,336 B1 | 5/2001 | Hrabie et al. |
| RE37,234 E | 6/2001 | Garvey et al. |
| 6,316,457 B1 | 11/2001 | Garvey et al. |
| 6,331,542 B1 | 12/2001 | Carr et al. |
| 6,633,272 B1 | 10/2003 | Kumagawa et al. |
| 7,273,946 B2 | 9/2007 | Ongini et al. |
| 2004/0171681 A1 | 9/2004 | Orihashi et al. |
| 2005/0153946 A1 | 7/2005 | Hirsh et al. |
| 2005/0272743 A1 | 12/2005 | Ongini et al. |

FOREIGN PATENT DOCUMENTS

| | | | |
|---|---|---|---|
| WO | WO-93/09806 | | 5/1993 |
| WO | WO-94/01422 | | 1/1994 |
| WO | WO-94/03387 | | 2/1994 |
| WO | WO-94/15723 | | 7/1994 |
| WO | WO-94/20480 | | 9/1994 |
| WO | WO-94/26731 | | 11/1994 |
| WO | WO-94/27980 | | 12/1994 |
| WO | WO-95/00501 | | 1/1995 |
| WO | WO-95/15316 | | 6/1995 |
| WO | WO-96/03387 | | 2/1996 |
| WO | WO-96/03388 | | 2/1996 |
| WO | WO-96/06840 | | 3/1996 |
| WO | WO-96/21667 | | 7/1996 |
| WO | WO-96/31509 | | 10/1996 |
| WO | WO-96/36623 | | 11/1996 |
| WO | WO-97/14691 | | 4/1997 |
| WO | WO-97/16435 | | 5/1997 |
| WO | WO-97/27749 | | 8/1997 |
| WO | WO-97/46521 | | 12/1997 |
| WO | WO-98/19672 | | 5/1998 |
| WO | WO-98/58910 A1 | | 12/1998 |
| WO | WO-99/64417 | | 12/1999 |
| WO | WO-00/28988 | | 5/2000 |
| WO | WO-00/51978 A1 | | 9/2000 |
| WO | WO-00/54756 | | 9/2000 |
| WO | WO-01/45703 | | 6/2001 |
| WO | WO-01/87343 | | 11/2001 |
| WO | WO-03/013432 A | | 2/2003 |
| WO | WO-03/017996 | | 3/2003 |
| WO | WO 05/068421 | * 7/2005 | ............ C07C 405/00 |
| WO | WO-2007/123818 A2 | | 11/2007 |

OTHER PUBLICATIONS

Cena et al. "Antiinflammatory, gastrosparing, and antiplatelet properties of new NO-donor esters of aspirin," J. Med. Chem. 46: 747-754 (8 pages) (2003).

Cerecetto, et al. "1,2,5-Oxadiazole N-oxide derivatives and related compounds as potential antitrypanosomal drugs: structure-activity relationships," J. Med. Chem. 42: 1941-1950 (10 pages) (1999).

De Stilo, et al. "New 1,4-dihydropyridines conjugated to furoxanyl moieties, endowed with both nitric oxide-like and calcium channel antagonist vasodilator activities," J. Med. Chem. 41: 5393-5401 (9 pages) (1998).

Fruttero, et al. "The furoxan system as a useful tool for balancing "hybrids" with mixed $a_1$-antagonist and NO-like vasodilator activities," J. Med. Chem. 38: 4944-4949 (6 pages) (1995).

Ignarro et al. "Endothelium-derived relaxing factor produced and released from artery and vein is nitric oxide," Proc. Natl. Acad. Sci. 84: 9265-9269 (5 pages) (1987).

Oae et al. "Organic thionitrites and related substances," Org. Prep. Proc. Int. 15(3): 165-198 (38 pages) (1983).

Palmer et al. "Nitric oxide release accounts for the biological activity of endothelium-derived relaxing factor," Nature, 327: 524-526 (3 pages) (1987).

International Search Report mailed Sep. 12, 2007 for International Patent Application No. PCT/US07/06749 (2 pages).

Rokach et al. "Nomenclature of isoprostanes: a proposal," Prostaglandins, 54: 853-873 (21 pages) (1997).

Rokach et al. "The isoprostanes: a perspective," Prostaglandins, 54: 823-851 (29 pages) (1997).

Sorba, et al. "Mixed Antisecretory and gastroprotective activities of a new $H_2$-Antagonist Containing a Nitric Oxide-donor FuroxanMoiety," Arzneim. Forsch. Drug Res. 47: 849-854 (8 pages) (1997).

Wang et al. "Nitric oxide donors: chemical activities and biological applications," Chem. Rev. 102: 1091-1134 (44 pages) (2002).

Supplemental Search Report and Written Opinion mailed Aug. 8, 2011 for corresponding European Patent Application No. 07753382.6 (5 pages).

* cited by examiner

NITRIC OXIDE ENHANCING PROSTAGLANDIN COMPOUNDS, COMPOSITIONS AND METHODS OF USE

RELATED APPLICATIONS

This application is a divisional of U.S. application Ser. No. 12/294,642, filed Sep. 26, 2008, issued as U.S. Pat. No. 8,067,414, which is U.S. national phase application under 35 U.S.C. §371 of International Application No. PCT/US2007/0006749, filed Mar. 19, 2007, which claims priority under 35 USC §119(e) to U.S. Application No. 60/786,689 filed Mar. 29, 2006; the disclosure of each of which is incorporated by reference herein in its entirety.

FIELD OF THE INVENTION

The invention describes compositions and kits comprising at least one nitric oxide enhancing prostaglandin compound or a pharmaceutically acceptable salt thereof, and, optionally, at least one nitric oxide enhancing compound and/or at least one therapeutic agent. The invention also provides methods for (a) treating ophthalmic disorders; (b) treating cerebrovascular disorders; (c) treating cardiovascular disorders; (d) treating benign prostatic hyperplasia (BPH); (e) treating peptic ulcers; (e) treating sexual dysfunctions and (f) inducing abortions. The nitric oxide enhancing prostaglandin compounds comprise at least one heterocyclic nitric oxide donor group and/or at least one nitroxide group.

BACKGROUND OF THE INVENTION

Most drugs conventionally used to treat ophthalmic disorders have potentially serious side effects such as blurring of vision and other visual side effects which may lead either to decreased patient compliance or to the termination of therapy. Occasionally systemically administered drugs can also cause serious side effects, such as nausea, dyspepsia, fatigue, and metabolic acidosis, which affect patient compliance and/or necessitate the termination of treatment. Additionally, some β-adrenergic antagonists have increasingly become associated with serious pulmonary side effects attributable to their effects on β-2 receptors in pulmonary tissue. Hence there is a need in the art for compounds that have improved efficacy, lower toxicity and/or fewer side effects and that can be used at low dosages. The invention is directed to these, as well as other, important ends.

SUMMARY OF THE INVENTION

The invention provides novel nitric oxide enhancing prostaglandin compounds that are substituted with at least one heterocyclic nitric oxide donor group and/or at least one nitroxide group and pharmaceutically acceptable salts thereof. The prostaglandin compound can be substituted with the heterocyclic nitric oxide donor group and/or the nitroxide group through one or more sites such as oxygen (hydroxyl condensation), sulfur (sulfhydryl condensation) and/or nitrogen via a bond or moiety that can be hydrolyzed. The heterocyclic nitric oxide donors are furoxans, sydnonimines, oxatriazole-5-ones and/or oxatriazole-5-imines. The invention also provides compositions comprising the novel compounds described herein in a pharmaceutically acceptable carrier.

The invention is also based on the discovery that administering at least one nitric oxide enhancing prostaglandin compound (i.e. heterocyclic nitric oxide donor group and/or nitroxide group), or a pharmaceutically acceptable salt thereof, and, optionally, at least one nitric oxide enhancing compound improves the properties of the prostaglandin compound. Nitric oxide enhancing compounds include, for example, S-nitrosothiols, nitrites, nitrates, N-oxo-N-nitrosamines, furoxans, sydnonimines, SPM 3672, SPM 4757, SPM 5185, SPM 5186 and analogues thereof, substrates of the various isozymes of nitric oxide synthase, and nitroxides. Thus, another embodiment of the invention provides compositions comprising at least one nitric oxide enhancing prostaglandin compound and at least one nitric oxide enhancing compound. The invention also provides for such compositions in a pharmaceutically acceptable carrier.

The invention provides compositions comprising at least one nitric oxide enhancing prostaglandin compound, and, optionally, at least one nitric oxide enhancing compound and/or at least one therapeutic agent, including, but not limited to, aldosterone antagonists, α-adrenergic receptor agonists, α-adrenergic receptor antagonists, β-adrenergic agonists, antidiabetic compounds, antimicrobial compounds, anti-hyperlipidemic drugs, angiotensin II antagonists, angiotensin-converting enzyme (ACE) inhibitors, antioxidants, antithrombotic and vasodilator drugs, β-adrenergic antagonists, calcium channel blockers, carbonic anhydrase inhibitors, diuretics, endothelin antagonists, hydralazine compounds, $H_2$ receptor antagonists, neutral endopeptidase inhibitors, nonsteroidal antiinflammatory compounds (NSAIDs), phosphodiesterase inhibitors, potassium channel blockers, platelet reducing agents, prostaglandins, proton pump inhibitors, renin inhibitors, selective cyclooxygenase-2 (COX-2) inhibitors, steroids, compounds used for the treatment of glaucoma, and combinations of two or more thereof. The invention also provides for such compositions in a pharmaceutically acceptable carrier.

Another embodiment of the invention provides compositions comprising at least one nitric oxide enhancing prostaglandin compound, and at least one therapeutic agent selected from the group consisting of an α-adrenergic receptor antagonist, a β-adrenergic agonist, an antimicrobial compound, a β-adrenergic antagonist, a calcium channel blocker, a carbonic anhydrase inhibitor, a nonsteroidal antiinflammatory compound (NSAID), a phosphodiesterase inhibitor, a potassium channel blocker, a prostaglandin, a proton pump inhibitor, a selective cyclooxygenase-2 (COX-2) inhibitor, a steroid, a compound used for the treatment of glaucoma, and combinations of two or more thereof. The invention also provides for such compositions in a pharmaceutically acceptable carrier.

The invention provides methods for (a) treating ophthalmic disorders; (b) treating cerebrovascular disorders; (c) treating cardiovascular disorders; (d) treating benign prostatic hyperplasia (BPH); (e) treating peptic ulcers; (e) treating sexual dysfunctions and (f) inducing abortions in a patient in need thereof comprising administering to the patient an effective amount of at least one nitric oxide enhancing prostaglandin compound, and, optionally, at least one therapeutic agent, such as, for example, aldosterone antagonists, α-adrenergic receptor agonists, α-adrenergic receptor antagonists, β-adrenergic agonists, antidiabetic compounds, antimicrobial compounds, anti-hyperlipidemic drugs, angiotensin II antagonists, angiotensin-converting enzyme (ACE) inhibitors, antioxidants, antithrombotic and vasodilator drugs, β-adrenergic antagonists, calcium channel blockers, carbonic anhydrase inhibitors, diuretics, endothelin antagonists, hydralazine compounds, $H_2$ receptor antagonists, neutral endopeptidase inhibitors, nonsteroidal antiinflammatory compounds (NSAIDs), phosphodiesterase inhibitors, potassium channel blockers, platelet reducing agents, prostaglandins, proton pump inhibitors, renin inhibitors, selective cyclooxygenase-2 (COX-2) inhibitors, steroids, compounds used for the treatment of glaucoma, and combinations of two or more thereof. The methods can optionally further comprises the administration of at least one nitric oxide enhancing compound. In this embodiment of the invention, the methods can involve (i) administering the nitric oxide enhancing prostaglandin compounds, (ii) administering the nitric oxide enhancing prostaglandin compounds and nitric oxide enhancing compounds, (iii) administering the nitric oxide enhancing prostaglandin compounds and therapeutic agents, or (iv) administering the nitric oxide enhancing prostaglandin compounds, nitric oxide enhancing compounds, and therapeutic agents. In one embodiment the at least one therapeutic agent is selected from the group consisting of an α-adrenergic receptor antagonist, a β-adrenergic agonist, an antimicrobial compound, a β-adrenergic antagonist, a calcium channel blocker, a carbonic anhydrase inhibitor, a nonsteroidal antiinflammatory compound (NSAID), a phosphodiesterase inhibitor, a potassium channel blocker, a prostaglandin, a proton pump inhibitor, a selective cyclooxygenase-2 (COX-2) inhibitor, a steroid, and a compound used for the treatment of glaucoma. In another embodiment the ophthalmic disorder is glaucoma, elevated ocular pressure, macular degeneration, ophthalmic infection, dry eye disorder, ocular hypertension, and diabetic retinopathy. The nitric oxide enhancing prostaglandin compounds, nitric oxide enhancing compounds, and/or therapeutic agents can be administered separately or as components of the same composition in one or more pharmaceutically acceptable carriers.

Another embodiment of the invention provides kits comprising at least one nitric oxide enhancing prostaglandin compound, and, optionally, at least one nitric oxide enhancing compound. The kit can further comprise at least one therapeutic agent, such as, for example, aldosterone antagonists, α-adrenergic receptor agonists, α-adrenergic receptor antagonists, β-adrenergic agonists, antidiabetic compounds, antimicrobial compounds, anti-hyperlipidemic drugs, angiotensin II antagonists, angiotensin-converting enzyme (ACE) inhibitors, antioxidants, antithrombotic and vasodilator drugs, β-adrenergic antagonists, calcium channel blockers, carbonic anhydrase inhibitors, diuretics, endothelin antagonists, hydralazine compounds, $H_2$ receptor antagonists, neutral endopeptidase inhibitors, nonsteroidal antiinflammatory compounds (NSAIDs), phosphodiesterase inhibitors, potassium channel blockers, platelet reducing agents, prostaglandins, proton pump inhibitors, renin inhibitors, selective cyclooxygenase-2 (COX-2) inhibitors, steroids, compounds used for the treatment of glaucoma, and combinations of two or more thereof. The nitric oxide enhancing prostaglandin compound, the nitric oxide enhancing compound and/or therapeutic agent, can be separate components in the kit or can be in the form of a composition in one or more pharmaceutically acceptable carriers.

These and other aspects of the invention are described in detail herein.

DETAILED DESCRIPTION OF THE INVENTION

As used throughout the disclosure, the following terms, unless otherwise indicated, shall be understood to have the following meanings.

"Ophthalmic disorders" include, but are not limited to, glaucoma, elevated intraocular pressure, ocular pain (e.g., following corneal surgery), cataracts, ophthalmic infections, dry eye disorder, ocular hypertension, ocular bleeding, retinal diseases or disorders, presbyopia, macular degeneration, choroidal neovascularization (CNV), retinopathies, such as for example, diabetic retinopathy, vitreoretinopathy, and the like, retinitis, such as for example, cytomegalovirus (CMV) retinitis, uveitis, macular edema, neuropathies and the like.

"Ophthalmic infections" include, but are not limited to an inflammation of the conjunctiva (conjunctivitis), inflammation of the cornea (keratitis), corneal ulcers, and the like, caused by an organisms such as, for example, Staphylococci, Streptococci, Enterococci, *Bacillus, Corynebacterium, Chlamydia, Neisseria*, and the like, including important species of these genus such as, for example, *Staphylococcus aureus, Streptococcus viridans, Staphylococcus epidermis, Streptococcus pneumoniae*, staphylococci, streptococci, enterococci, and the like.

"Sexual dysfunction" refers to and includes male erectile dysfunction and female sexual dysfunction. Sexual dysfunction includes, but is not limited to, for example, sexual pain disorders, sexual desire disorders, sexual arousal dysfunction, orgasmic dysfunction, dyspareunia, vaginismus, and the like.

"Therapeutic agent" includes any therapeutic agent that can be used to treat or prevent the diseases described herein. "Therapeutic agents" include, for example, aldosterone antagonists, α-adrenergic receptor agonists, α-adrenergic receptor antagonists, β-adrenergic agonists, anti-allergic compounds, antidiabetic compounds, antimicrobial compounds, anti-hyperlipidemic drugs, antitussive compounds, angiotensin II antagonists, angiotensin-converting enzyme (ACE) inhibitors, antioxidants, antithrombotic and vasodilator drugs, β-adrenergic antagonists, bronchodilators, calcium channel blockers, carbonic anhydrase inhibitors, diuretics, endothelin antagonists, expectorants, hydralazine compounds, $H_2$ receptor antagonists, neutral endopeptidase inhibitors, nonsteroidal antiinflammatory compounds (NSAIDs), phosphodiesterase inhibitors, potassium channel blockers, platelet reducing agents, prostaglandins, proton pump inhibitors, renin inhibitors, selective cyclooxygenase-2 (COX-2) inhibitors, steroids, compounds used for the treatment of glaucoma, and the like. Therapeutic agent includes the pharmaceutically acceptable salts thereof, pro-drugs, and pharmaceutical derivatives thereof including, but not limited to, the corresponding nitrosated and/or nitrosylated and/or heterocyclic nitric oxide donor derivatives and/or nitroxide derivatives. Although nitric oxide donors have therapeutic activity, the term "therapeutic agent" does not include the nitric oxide donors described herein, since nitric oxide donors are separately defined.

"Prodrug" refers to a compound that is made more active in vivo.

"Antioxidant" refers to and includes any compound that can react and quench a free radical.

"Angiotensin converting enzyme (ACE) inhibitor" refers to compounds that inhibit an enzyme which catalyzes the conversion of angiotensin I to angiotensin II. ACE inhibitors include, but are not limited to, amino acids and derivatives thereof, peptides, including di- and tri-peptides, and antibodies to ACE which intervene in the renin-angiotensin system by inhibiting the activity of ACE thereby reducing or eliminating the formation of the presser substance angiotensin II.

"Angiotensin II antagonists" refers to compounds which interfere with the function, synthesis or catabolism of angiotensin II. Angiotensin II antagonists include peptide compounds and non-peptide compounds, including, but not limited to, angiotensin II antagonists, angiotensin II receptor antagonists, agents that activate the catabolism of angiotensin II, and agents that prevent the synthesis of angiotensin I from angiotensin II. The renin-angiotensin system is involved in the regulation of hemodynamics and water and electrolyte balance. Factors that lower blood volume, renal perfusion pressure, or the concentration of sodium in plasma tend to activate the system, while factors that increase these parameters tend to suppress its function.

"Anti-hyperlipidemic compounds" refers to any compound or agent that has the effect of beneficially modifying serum cholesterol levels such as, for example, lowering serum low density lipoprotein (LDL) cholesterol levels, or inhibiting oxidation of LDL cholesterol, whereas high density lipoprotein (HDL) serum cholesterol levels may be lowered, remain the same, or be increased. Preferably, the anti-hyperlipidemic compound brings the serum levels of LDL cholesterol and HDL cholesterol (and, more preferably, triglyceride levels) to normal or nearly normal levels.

"Diuretic compound" refers to and includes any compound or agent that increases the amount of urine excreted by a patient.

"Neutral endopeptidase inhibitors" refers to and includes compounds that are antagonists of the renin angiotensin aldosterone system including compounds that are dual inhibitors of neutral endopeptidases and angiotensin converting (ACE) enzymes.

"Renin inhibitors" refers to compounds which interfere with the activity of renin.

"Phosphodiesterase inhibitor" or "PDE inhibitor" refers to any compound that inhibits the enzyme phosphodiesterase. The term refers to selective or non-selective inhibitors of cyclic guanosine 3',5'-monophosphate phosphodiesterases (cGMP-PDE) and cyclic adenosine 3',5'-monophosphate phosphodiesterases (cAMP-PDE).

"Platelet reducing agents" refers to compounds that prevent the formation of a blood thrombus via any number of potential mechanisms. Platelet reducing agents include, but are not limited to, fibrinolytic agents, anti-coagulant agents and any inhibitors of platelet function. Inhibitors of platelet function include agents that impair the ability of mature platelets to perform their normal physiological roles (i.e., their normal function, such as, for example, adhesion to cellular and non-cellular entities, aggregation, release of factors such as growth factors) and the like.

"Proton pump inhibitor" refers to any compound that reversibly or irreversibly blocks gastric acid secretion by inhibiting the $H^+/K^+$-ATPase enzyme system at the secretory surface of the gastric parietal cell.

"NSAID" refers to a nonsteroidal anti-inflammatory compound or a nonsteroidal anti-inflammatory drug. NSAIDs inhibit cyclooxygenase, the enzyme responsible for the biosyntheses of the prostaglandins and certain autacoid inhibitors, including inhibitors of the various isozymes of cyclooxygenase (including but not limited to cyclooxygenase-1 and -2), and as inhibitors of both cyclooxygenase and lipoxygenase.

"Cyclooxygenase-2 (COX-2) selective inhibitor" refers to a compound that selectively inhibits the cyclooxygenase-2 enzyme over the cyclooxygenase-1 enzyme. In one embodiment, the compound has a cyclooxygenase-2 $IC_{50}$ of less than about 2 μM and a cyclooxygenase-1 $IC_{50}$ of greater than about 5 μM, in the human whole blood COX-2 assay (as described in Brideau et al., *Inflamm Res.*, 45: 68-74 (1996)) and also has a selectivity ratio of cyclooxygenase-2 inhibition over cyclooxygenase-1 inhibition of at least 10, and preferably of at least 40. In another embodiment, the compound has a cyclooxygenase-1 $IC_{50}$ of greater than about 1 μM, and preferably of greater than 20 μM. The compound can also inhibit the enzyme, lipoxygenase. Such selectivity may indicate an ability to reduce the incidence of common NSAID-induced side effects.

"Patient" refers to animals, preferably mammals, most preferably humans, and includes males and females, and children and adults.

"Transdermal" refers to the delivery of a compound by passage through the skin and into the blood stream.

"Transmucosal" refers to delivery of a compound by passage of the compound through the mucosal tissue and into the blood stream.

"Penetration enhancement" or "permeation enhancement" refers to an increase in the permeability of the skin or mucosal tissue to a selected pharmacologically active compound such that the rate at which the compound permeates through the skin or mucosal tissue is increased.

"Carriers" or "vehicles" refers to carrier materials suitable for compound administration and include any such material known in the art such as, for example, any liquid, gel, solvent, liquid diluent, solubilizer, or the like, which is non-toxic and which does not interact with any components of the composition in a deleterious manner.

"Sustained release" refers to the release of an active compound and/or composition such that the blood levels of the active compound are maintained within a desirable therapeutic range over a period of time. The sustained release formulation can be prepared using any conventional method known to one skilled in the art to obtain the desired release characteristics.

"Nitric oxide enhancing" refers to compounds and functional groups which, under physiological conditions can increase endogenous nitric oxide. Nitric oxide enhancing compounds include, but are not limited to, nitric oxide releasing compounds, nitric oxide donating compounds, nitric oxide donors, radical scavenging compounds and/or reactive oxygen species scavenger compounds. In one embodiment the radical scavenging compound contains a nitroxide group.

"Nitroxide group" refers to compounds that have the ability to mimic superoxide dimutase and catalase and act as radical scavengers, or react with superoxide or other reactive oxygen species via a stable aminoxyl radical i.e. N-oxide.

"Nitric oxide adduct" or "NO adduct" refers to compounds and functional groups which, under physiological conditions, can donate, release and/or directly or indirectly transfer any of the three redox forms of nitrogen monoxide ($NO^+$, $NO^-$, NO.), such that the biological activity of the nitrogen monoxide species is expressed at the intended site of action.

"Nitric oxide releasing" or "nitric oxide donating" refers to methods of donating, releasing and/or directly or indirectly transferring any of the three redox forms of nitrogen monoxide ($NO^+$, $NO^-$, NO.), such that the biological activity of the nitrogen monoxide species is expressed at the intended site of action.

"Nitric oxide donor" or "NO donor" refers to compounds that donate, release and/or directly or indirectly transfer a nitrogen monoxide species, and/or stimulate the endogenous production of nitric oxide or endothelium-derived relaxing factor (EDRF) in vivo and/or elevate endogenous levels of nitric oxide or EDRF in vivo and/or are oxidized to produce nitric oxide and/or are substrates for nitric oxide synthase and/or cytochrome P450. "NO donor" also includes compounds that are precursors of L-arginine, inhibitors of the enzyme arginase and nitric oxide mediators.

"Heterocyclic nitric oxide donor" refers to a trisubstituted 5-membered ring comprising two or three nitrogen atoms and at least one oxygen atom. The heterocyclic nitric oxide donor is capable of donating and/or releasing a nitrogen monoxide species upon decomposition of the heterocyclic ring. Exemplary heterocyclic nitric oxide donors include oxatriazol-5-ones, oxatriazol-5-imines, sydnonimines, furoxans, and the like.

"Alkyl" refers to a lower alkyl group, a substituted lower alkyl group, a haloalkyl group, a hydroxyalkyl group, an alkenyl group, a substituted alkenyl group, an alkynyl group, a bridged cycloalkyl group, a cycloalkyl group or a heterocyclic ring, as defined herein. An alkyl group may also comprise one or more radical species, such as, for example a cycloalkylalkyl group or a heterocyclicalkyl group.

"Lower alkyl" refers to branched or straight chain acyclic alkyl group comprising one to about ten carbon atoms (preferably one to about eight carbon atoms, more preferably one to about six carbon atoms). Exemplary lower alkyl groups include methyl, ethyl, n-propyl, isopropyl, n-butyl, isobutyl, sec-butyl, t-butyl, pentyl, neopentyl, iso-amyl, hexyl, octyl, and the like.

"Substituted lower alkyl" refers to a lower alkyl group, as defined herein, wherein one or more of the hydrogen atoms have been replaced with one or more $R^{100}$ groups, wherein each $R^{100}$ is independently a hydroxy, an ester, an amidyl, an oxo, a carboxyl, a carboxamido, a halo, a cyano, a nitrate, a nitrite, a thionitrate, a thionitrite or an amino group, as defined herein.

"Haloalkyl" refers to a lower alkyl group, an alkenyl group, an alkynyl group, a bridged cycloalkyl group, a cycloalkyl group or a heterocyclic ring, as defined herein, to which is appended one or more halogens, as defined herein. Exemplary haloalkyl groups include trifluoromethyl, chloromethyl, 2-bromobutyl, 1-bromo-2-chloro-pentyl, and the like.

"Alkenyl" refers to a branched or straight chain $C_2$-$C_{10}$ hydrocarbon (preferably a $C_2$-$C_8$ hydrocarbon, more preferably a $C_2$-$C_6$ hydrocarbon) that can comprise one or more carbon-carbon double bonds. Exemplary alkenyl groups include propylenyl, buten-1-yl, isobutenyl, penten-1-yl, 2,2-methylbuten-1-yl, 3-methylbuten-1-yl, hexan-1-yl, hepten-1-yl, octen-1-yl, and the like.

"Lower alkenyl" refers to a branched or straight chain $C_2$-$C_4$ hydrocarbon that can comprise one or two carbon-carbon double bonds.

"Substituted alkenyl" refers to a branched or straight chain $C_2$-$C_{10}$ hydrocarbon (preferably a $C_2$-$C_8$ hydrocarbon, more preferably a $C_2$-$C_6$ hydrocarbon) which can comprise one or more carbon-carbon double bonds, wherein one or more of the hydrogen atoms have been replaced with one or more $R^{100}$ groups, wherein each $R^{100}$ is independently a hydroxy, an oxo, a carboxyl, a carboxamido, a halo, a cyano or an amino group, as defined herein.

"Alkynyl" refers to an unsaturated acyclic $C_2$-$C_{10}$ hydrocarbon (preferably a $C_2$-$C_8$ hydrocarbon, more preferably a $C_2$-$C_6$ hydrocarbon) that can comprise one or more carbon-carbon triple bonds. Exemplary alkynyl groups include ethynyl, propynyl, butyn-1-yl, butyn-2-yl, pentyl-1-yl, pentyl-2-yl, 3-methylbutyn-1-yl, hexyl-1-yl, hexyl-2-yl, hexyl-3-yl, 3,3-dimethyl-butyn-1-yl, and the like.

"Bridged cycloalkyl" refers to two or more cycloalkyl groups, heterocyclic groups, or a combination thereof fused via adjacent or non-adjacent atoms. Bridged cycloalkyl groups can be unsubstituted or substituted with one, two or three substituents independently selected from alkyl, alkoxy, amino, alkylamino, dialkylamino, hydroxy, halo, carboxyl, alkylcarboxylic acid, aryl, amidyl, ester, alkylcarboxylic ester, carboxamido, alkylcarboxamido, oxo and nitro. Exemplary bridged cycloalkyl groups include adamantyl, decahydronapthyl, quinuclidyl, 2,6-dioxabicyclo(3.3.0)octane, 7-oxabicyclo(2.2.1)heptyl, 8-azabicyclo(3,2,1)oct-2-enyl and the like.

"Cycloalkyl" refers to a saturated or unsaturated cyclic hydrocarbon comprising from about 3 to about 10 carbon atoms. Cycloalkyl groups can be unsubstituted or substituted with one, two or three substituents independently selected from alkyl, alkoxy, amino, alkylamino, dialkylamino, arylamino, diarylamino, alkylarylamino, aryl, amidyl, ester, hydroxy, halo, carboxyl, alkylcarboxylic acid, alkylcarboxylic ester, carboxamido, alkylcarboxamido, oxo, alkylsulfinyl, and nitro. Exemplary cycloalkyl groups include cyclopropyl, cyclobutyl, cyclopentyl, cyclohexyl, cyclohexenyl, cyclohepta-1,3-dienyl, and the like.

"Heterocyclic ring or group" refers to a saturated or unsaturated cyclic hydrocarbon group having about 2 to about 10 carbon atoms (preferably about 4 to about 6 carbon atoms) where 1 to about 4 carbon atoms are replaced by one or more nitrogen, oxygen and/or sulfur atoms. Sulfur may be in the thio, sulfinyl or sulfonyl oxidation state. The heterocyclic ring or group can be fused to an aromatic hydrocarbon group. Heterocyclic groups can be unsubstituted or substituted with one, two or three substituents independently selected from alkyl, alkoxy, amino, alkylthio, aryloxy, arylthio, arylalkyl, hydroxy, oxo, thial, halo, carboxyl, carboxylic ester, alkylcarboxylic acid, alkylcarboxylic ester, aryl, arylcarboxylic acid, arylcarboxylic ester, amidyl, ester, alkylcarbonyl, arylcarbonyl, alkylsulfinyl, carboxamido, alkylcarboxamido, arylcarboxamido, sulfonic acid, sulfonic ester, sulfonamide nitrate and nitro. Exemplary heterocyclic groups include pyrrolyl, furyl, thienyl, 3-pyrrolinyl,4,5,6-trihydro-2H-pyranyl, pyridinyl, 1,4-dihydropyridinyl, pyrazolyl, triazolyl, pyrimidinyl, pyridazinyl, oxazolyl, thiazolyl, imidazolyl, indolyl, thiophenyl, furanyl, tetrahydrofuranyl, tetrazolyl, pyrrolinyl, pyrrolindinyl, oxazolindinyl 1,3-dioxolanyl, imidazolinyl, imidazolindinyl, pyrazolinyl, pyrazolidinyl, isoxazolyl, isothiazolyl, 1,2,3-oxadiazolyl, 1,2,3-triazolyl, 1,3,4-thiadiazolyl, 2H-pyranyl, 4H-pyranyl, piperidinyl, 1,4-dioxanyl, morpholinyl, 1,4-dithianyl, thiomorpholinyl, pyrazinyl, piperazinyl, 1,3,5-triazinyl, 1,3,5-trithianyl, benzo(b)thiophenyl, benzimidazolyl, benzothiazolinyl, quinolinyl, 2,6-dioxabicyclo(3.3.0)octane, and the like.

"Heterocyclic compounds" refer to mono- and polycyclic compounds comprising at least one aryl or heterocyclic ring.

"Aryl" refers to a monocyclic, bicyclic, carbocyclic or heterocyclic ring system comprising one or two aromatic rings. Exemplary aryl groups include phenyl, pyridyl, napthyl, quinoyl, tetrahydronaphthyl, furanyl, indanyl, indenyl, indoyl, and the like. Aryl groups (including bicyclic aryl groups) can be unsubstituted or substituted with one, two or three substituents independently selected from alkyl, alkoxy, alkylthio, amino, alkylamino, dialkylamino, arylamino, diarylamino, alkylarylamino, halo, cyano, alkylsulfinyl, hydroxy, carboxyl, carboxylic ester, alkylcarboxylic acid, alkylcarboxylic ester, aryl, arylcarboxylic acid, arylcarboxylic ester, alkylcarbonyl, arylcarbonyl, amidyl, ester, carboxamido, alkylcarboxamido, carbomyl, sulfonic acid, sulfonic ester, sulfonamido and nitro. Exemplary substituted aryl groups include tetrafluorophenyl, pentafluorophenyl, sulfonamide, alkylsulfonyl, arylsulfonyl, and the like.

"Cycloalkenyl" refers to an unsaturated cyclic $C_2$-$C_{10}$ hydrocarbon (preferably a $C_2$-$C_8$ hydrocarbon, more preferably a $C_2$-$C_6$ hydrocarbon) which can comprise one or more carbon-carbon double bonds.

"Alkylaryl" refers to an alkyl group, as defined herein, to which is appended an aryl group, as defined herein. Exemplary alkylaryl groups include benzyl, phenylethyl, hydroxybenzyl, fluorobenzyl, fluorophenylethyl, and the like.

"Arylalkyl" refers to an aryl radical, as defined herein, attached to an alkyl radical, as defined herein. Exemplary arylalkyl groups include benzyl, phenylethyl, 4-hydroxybenzyl, 3-fluorobenzyl, 2-fluorophenylethyl, and the like.

"Arylalkenyl" refers to an aryl radical, as defined herein, attached to an alkenyl radical, as defined herein. Exemplary arylalkenyl groups include styryl, propenylphenyl, and the like.

"Cycloalkylalkyl" refers to a cycloalkyl radical, as defined herein, attached to an alkyl radical, as defined herein.

"Cycloalkylalkoxy" refers to a cycloalkyl radical, as defined herein, attached to an alkoxy radical, as defined herein.

"Cycloalkylalkylthio" refers to a cycloalkyl radical, as defined herein, attached to an alkylthio radical, as defined herein.

"Heterocyclicalkyl" refers to a heterocyclic ring radical, as defined herein, attached to an alkyl radical, as defined herein.

"Arylheterocyclic ring" refers to a bi- or tricyclic ring comprised of an aryl ring, as defined herein, appended via two adjacent carbon atoms of the aryl ring to a heterocyclic ring, as defined herein. Exemplary arylheterocyclic rings include dihydroindole, 1,2,3,4-tetra-hydroquinoline, and the like.

"Alkylheterocyclic ring" refers to a heterocyclic ring radical, as defined herein, attached to an alkyl radical, as defined herein. Exemplary alkylheterocyclic rings include 2-pyridylmethyl, 1-methylpiperidin-2-one-3-methyl, and the like.

"Alkoxy" refers to $R_{50}O-$, wherein $R_{50}$ is an alkyl group, as defined herein (preferably a lower alkyl group or a haloalkyl group, as defined herein). Exemplary alkoxy groups include methoxy, ethoxy, t-butoxy, cyclopentyloxy, trifluoromethoxy, and the like.

"Aryloxy" refers to $R_{55}O-$, wherein $R_{55}$ is an aryl group, as defined herein. Exemplary arylkoxy groups include napthyloxy, quinolyloxy, isoquinolizinyloxy, and the like.

"Alkylthio" refers to $R_{50}S-$, wherein $R_{50}$ is an alkyl group, as defined herein.

"Lower alkylthio" refers to a lower alkyl group, as defined herein, appended to a thio group, as defined herein.

"Arylalkoxy" or "alkoxyaryl" refers to an alkoxy group, as defined herein, to which is appended an aryl group, as defined herein. Exemplary arylalkoxy groups include benzyloxy, phenylethoxy, chlorophenylethoxy, and the like.

"Arylalklythio" refers to an alkylthio group, as defined herein, to which is appended an aryl group, as defined herein. Exemplary arylalklythio groups include benzylthio, phenylethylthio, chlorophenylethylthio, and the like.

"Arylalklythioalkyl" refers to an arylalkylthio group, as defined herein, to which is appended an alkyl group, as defined herein. Exemplary arylalklythioalkyl groups include benzylthiomethyl, phenylethylthiomethyl, chlorophenylethylthioethyl, and the like.

"Alkylthioalkyl" refers to an alkylthio group, as defined herein, to which is appended an alkyl group, as defined herein. Exemplary alkylthioalkyl groups include allylthiomethyl, ethylthiomethyl, trifluoroethylthiomethyl, and the like.

"Alkoxyalkyl" refers to an alkoxy group, as defined herein, appended to an alkyl group, as defined herein. Exemplary alkoxyalkyl groups include methoxymethyl, methoxyethyl, isopropoxymethyl, and the like.

"Alkoxyhaloalkyl" refers to an alkoxy group, as defined herein, appended to a haloalkyl group, as defined herein. Exemplary alkoxyhaloalkyl groups include 4-methoxy-2-chlorobutyl and the like.

"Cycloalkoxy" refers to $R_{54}O-$, wherein $R_{54}$ is a cycloalkyl group or a bridged cycloalkyl group, as defined herein. Exemplary cycloalkoxy groups include cyclopropyloxy, cyclopentyloxy, cyclohexyloxy, and the like.

"Cycloalkylthio" refers to $R_{54}S-$, wherein $R_{54}$ is a cycloalkyl group or a bridged cycloalkyl group, as defined herein. Exemplary cycloalkylthio groups include cyclopropylthio, cyclopentylthio, cyclohexylthio, and the like.

"Haloalkoxy" refers to an alkoxy group, as defined herein, in which one or more of the hydrogen atoms on the alkoxy group are substituted with halogens, as defined herein. Exemplary haloalkoxy groups include 1,1,1-trichloroethoxy, 2-bromobutoxy, and the like.

"Hydroxy" refers to —OH.

"Oxy" refers to —O—

"Oxo" refers to =O.

"Oxylate" refers to $-O^-R_{77}^+$ wherein $R_{77}$ is an organic or inorganic cation.

"Thiol" refers to —SH.

"Thio" refers to —S—.

"Oxime" refers to $=N-OR_{81}$ wherein $R_{81}$ is a hydrogen, an alkyl group, an aryl group, an alkylsulfonyl group, an arylsulfonyl group, a carboxylic ester, an alkylcarbonyl group, an arylcarbonyl group, a carboxamido group, an alkoxyalkyl group or an alkoxyaryl group.

"Hydrazone" refers to $=N-N(R_{81})(R'_{81})$ wherein $R'_{81}$ is independently selected from $R_{81}$, and $R_{81}$ is as defined herein.

"Hydrazino" refers to $H_2N-N(H)-$.

"Organic cation" refers to a positively charged organic ion. Exemplary organic cations include alkyl substituted ammonium cations, and the like.

"Inorganic cation" refers to a positively charged metal ion. Exemplary inorganic cations include Group I metal cations such as for example, sodium, potassium, magnesium, calcium, and the like.

"Hydroxyalkyl" refers to a hydroxy group, as defined herein, appended to an alkyl group, as defined herein.

"Nitrate" refers to —O—$NO_2$ i.e. oxidized nitrogen.

"Nitrite" refers to —O—NO i.e. oxidized nitrogen.

"Thionitrate" refers to —S—$NO_2$.

"Thionitrite" and "nitrosothiol" refer to —S—NO.

"Nitro" refers to the group —$NO_2$ and "nitrosated" refers to compounds that have been substituted therewith.

"Nitroso" refers to the group —NO and "nitrosylated" refers to compounds that have been substituted therewith.

"Nitrile" and "cyano" refer to —CN.

"Halogen" or "halo" refers to iodine (I), bromine (Br), chlorine (Cl), and/or fluorine (F).

"Imine" refers to $-C(=N-R_{51})-$ wherein $R_{51}$ is a hydrogen atom, an alkyl group, an aryl group or an arylheterocyclic ring, as defined herein "Amine" refers to any organic compound that contains at least one basic nitrogen atom.

"Amino" refers to —$NH_2$, an alkylamino group, a dialkylamino group, an arylamino group, a diarylamino group, an alkylarylamino group or a heterocyclic ring, as defined herein.

"Alkylamino" refers to $R_{50}NH-$, wherein $R_{50}$ is an alkyl group, as defined herein. Exemplary alkylamino groups include methylamino, ethylamino, butylamino, cyclohexylamino, and the like.

"Arylamino" refers to $R_{55}NH-$, wherein $R_{55}$ is an aryl group, as defined herein.

"Dialkylamino" refers to $R_{52}R_{53}N-$, wherein $R_{52}$ and $R_{53}$ are each independently an alkyl group, as defined herein. Exemplary dialkylamino groups include dimethylamino, diethylamino, methyl propargylamino, and the like.

"Diarylamino" refers to $R_{55}R_{60}N$—, wherein $R_{55}$ and $R_{60}$ are each independently an aryl group, as defined herein.

"Alkylarylamino" or "arylalkylamino" refers to $R_{52}R_{55}N$—, wherein $R_{52}$ is an alkyl group, as defined herein, and $R_{55}$ is an aryl group, as defined herein.

"Alkylarylalkylamino" refers to $R_{52}R_{79}N$—, wherein $R_{52}$ is an alkyl group, as defined herein, and $R_{79}$ is an arylalkyl group, as defined herein.

"Alkylcycloalkylamino" refers to $R_{52}R_{80}N$—, wherein $R_{52}$ is an alkyl group, as defined herein, and $R_{80}$ is a cycloalkyl group, as defined herein.

"Aminoalkyl" refers to an amino group, an alkylamino group, a dialkylamino group, an arylamino group, a diarylamino group, an alkylarylamino group or a heterocyclic ring, as defined herein, to which is appended an alkyl group, as defined herein. Exemplary aminoalkyl groups include dimethylaminopropyl, diphenylaminocyclopentyl, methylaminomethyl, and the like.

"Aminoaryl" refers to an aryl group to which is appended an alkylamino group, an arylamino group or an arylalkylamino group. Exemplary aminoaryl groups include anilino, N-methylanilino, N-benzylanilino, and the like.

"Sulfinyl" refers to —S(O)—.

"Methanthial" refers to —C(S)—.

"Thial" refers to =S.

"Sulfonyl" refers to —S(O)$_2$.

"Sulfonic acid" refers to —S(O)$_2$OR$_{76}$, wherein $R_{76}$ is a hydrogen, an organic cation or an inorganic cation, as defined herein.

"Alkylsulfonic acid" refers to a sulfonic acid group, as defined herein, appended to an alkyl group, as defined herein.

"Arylsulfonic acid" refers to a sulfonic acid group, as defined herein, appended to an aryl group, as defined herein.

"Sulfonic ester" refers to —S(O)$_2$OR$_{58}$, wherein $R_{58}$ is an alkyl group, an aryl group, or an aryl heterocyclic ring, as defined herein.

"Sulfonamido" refers to —S(O)$_2$—N(R$_{51}$)(R$_{57}$), wherein $R_{51}$ and $R_{57}$ are each independently a hydrogen atom, an alkyl group, an aryl group or an arylheterocyclic ring, as defined herein, or $R_{51}$ and $R_{57}$ when taken together are a heterocyclic ring, a cycloalkyl group or a bridged cycloalkyl group, as defined herein.

"Alkylsulfonamido" refers to a sulfonamido group, as defined herein, appended to an alkyl group, as defined herein.

"Arylsulfonamido" refers to a sulfonamido group, as defined herein, appended to an aryl group, as defined herein.

"Alkylthio" refers to $R_{50}S$—, wherein $R_{50}$ is an alkyl group, as defined herein (preferably a lower alkyl group, as defined herein).

"Arylthio" refers to $R_{55}S$—, wherein $R_{55}$ is an aryl group, as defined herein.

"Arylalkylthio" refers to an aryl group, as defined herein, appended to an alkylthio group, as defined herein.

"Alkylsulfinyl" refers to $R_{50}$—S(O)—, wherein $R_{50}$ is an alkyl group, as defined herein.

"Alkylsulfonyl" refers to $R_{50}$—S(O)$_2$—, wherein $R_{50}$ is an alkyl group, as defined herein.

"Alkylsulfonyloxy" refers to $R_{50}$—S(O)$_2$—O—, wherein $R_{50}$ is an alkyl group, as defined herein.

"Arylsulfinyl" refers to $R_{55}$—S(O)—, wherein $R_{55}$ is an aryl group, as defined herein.

"Arylsulfonyl" refers to $R_{55}$—S(O)$_2$—, wherein $R_{55}$ is an aryl group, as defined herein.

"Arylsulfonyloxy" refers to $R_{55}$—S(O)$_2$—O—, wherein $R_{55}$ is an aryl group, as defined herein.

"Amidyl" refers to $R_{51}C(O)N(R_{57})$— wherein $R_{51}$ and $R_{57}$ are each independently a hydrogen atom, an alkyl group, an aryl group or an arylheterocyclic ring, as defined herein.

"Ester" refers to $R_{51}C(O)R_{82}$— wherein $R_{51}$ is a hydrogen atom, an alkyl group, an aryl group or an arylheterocyclic ring, as defined herein and $R_{82}$ is oxygen or sulfur.

"Carbamoyl" refers to —O—C(O)N(R$_{51}$)(R$_{57}$), wherein $R_{51}$ and $R_{57}$ are each independently a hydrogen atom, an alkyl group, an aryl group or an arylheterocyclic ring, as defined herein, or $R_{51}$ and $R_{57}$ taken together are a heterocyclic ring, a cycloalkyl group or a bridged cycloalkyl group, as defined herein.

"Carboxyl" refers to —C(O)OR$_{76}$, wherein $R_{76}$ is a hydrogen, an organic cation or an inorganic cation, as defined herein.

"Carbonyl" refers to —C(O)—.

"Alkylcarbonyl" refers to $R_{52}$—C(O)—, wherein $R_{52}$ is an alkyl group, as defined herein.

"Arylcarbonyl" refers to $R_{55}$—C(O)—, wherein $R_{55}$ is an aryl group, as defined herein.

"Arylalkylcarbonyl" refers to $R_{55}$—R$_{52}$—C(O)—, wherein $R_{55}$ is an aryl group, as defined herein, and $R_{52}$ is an alkyl group, as defined herein.

"Alkylarylcarbonyl" refers to $R_{52}$—R$_{55}$—C(O)—, wherein $R_{55}$ is an aryl group, as defined herein, and $R_{52}$ is an alkyl group, as defined herein.

"Heterocyclicalkylcarbonyl" refer to $R_{78}C(O)$— wherein $R_{78}$ is a heterocyclicalkyl group, as defined herein.

"Carboxylic ester" refers to —C(O)OR$_{58}$, wherein $R_{58}$ is an alkyl group, an aryl group or an aryl heterocyclic ring, as defined herein.

"Alkylcarboxylic acid" and "alkylcarboxyl" refer to an alkyl group, as defined herein, appended to a carboxyl group, as defined herein.

"Alkylcarboxylic ester" refers to an alkyl group, as defined herein, appended to a carboxylic ester group, as defined herein.

"Alkyl ester" refers to an alkyl group, as defined herein, appended to an ester group, as defined herein.

"Arylcarboxylic acid" refers to an aryl group, as defined herein, appended to a carboxyl group, as defined herein.

"Arylcarboxylic ester" and "arylcarboxyl" refer to an aryl group, as defined herein, appended to a carboxylic ester group, as defined herein.

"Aryl ester" refers to an aryl group, as defined herein, appended to an ester group, as defined herein.

"Carboxamido" refers to —C(O)N(R$_{51}$)(R$_{57}$), wherein $R_{51}$ and $R_{57}$ are each independently a hydrogen atom, an alkyl group, an aryl group or an arylheterocyclic ring, as defined herein, or $R_{51}$ and $R_{57}$ when taken together are a heterocyclic ring, a cycloalkyl group or a bridged cycloalkyl group, as defined herein.

"Alkylcarboxamido" refers to an alkyl group, as defined herein, appended to a carboxamido group, as defined herein.

"Arylcarboxamido" refers to an aryl group, as defined herein, appended to a carboxamido group, as defined herein.

"Urea" refers to —N(R$_{59}$)—C(O)N(R$_{51}$)(R$_{57}$) wherein $R_{51}$, $R_{57}$, and $R_{59}$ are each independently a hydrogen atom, an alkyl group, an aryl group or an arylheterocyclic ring, as defined herein, or $R_{51}$ and $R_{57}$ taken together are a heterocyclic ring, a cycloalkyl group or a bridged cycloalkyl group, as defined herein.

"Phosphoryl" refers to —P(R$_{70}$)(R$_{71}$)(R$_{72}$), wherein $R_{70}$ is a lone pair of electrons, thial or oxo, and $R_{71}$ and $R_{72}$ are each independently a covalent bond, a hydrogen, a lower alkyl, an alkoxy, an alkylamino, a hydroxy, an oxy or an aryl, as defined herein.

"Phosphoric acid" refers to —P(O)(OR$_{51}$)OH wherein R$_{51}$ is a hydrogen atom, an alkyl group, an aryl group or an arylheterocyclic ring, as defined herein.

"Phosphinic acid" refers to —P(O)(R$_{51}$)OH wherein R$_{51}$ is a hydrogen atom, an alkyl group, an aryl group or an arylheterocyclic ring, as defined herein.

"Silyl" refers to —Si(R$_{73}$)(R$_{74}$)(R$_{75}$), wherein R$_{73}$, R$_{74}$ and R$_{75}$ are each independently a covalent bond, a lower alkyl, an alkoxy, an aryl or an arylalkoxy, as defined herein.

Suitable prostaglandins include, but are not limited to, naturally occurring prostaglandins such as, for example, PGE$_0$, PGE$_1$, PGA$_1$, PGB$_1$, PGF$_1$, PGF$_2$, PGE$_{1\alpha}$, 19-hydroxy-PGA$_1$, 19-hydroxy-PGB$_1$, PGE$_2$, PGA$_2$, PGB$_2$, 19-hydroxy-PGA$_2$, 19-hydroxy-PGB$_2$, PGE$_3$, PGF$_3$, PGD$_2$, PGI$_2$, prostacyclins, thromboxanes, leukotrienes, 6-keto-PGE$_1$ derivatives and carbacyclin derivatives; or semisynthetic or synthetic derivatives of natural prostaglandins, including, but not limited to, carboprost tromethamine, dinoprost tromethamine, dinoprostone, gemeprost, metenoprost, sulprostone and triprost. Also included are the hydroxy derivatives of PGE$_2$ including, for example, 19-OH-PGE$_2$, 18-OH-PGE$_2$, 20-OH-PGE$_2$ and the salts and esters thereof as disclosed in WO 99/02164, the disclosure of which is incorporated by reference herein in its entirety. Other prostaglandin compound for use in the present invention include isoprostanes, such as 8-iso-PGE$_{2\alpha}$, 8-iso-PGE$_2$, iPF$_2\alpha$-VI, 12-iso-PGF$_{2\alpha}$, and the like, as described by, for example, Rokach et al *Prostaglandins*, 54: 823-851, (1997) and Rokach et al, *Prostaglandins*, 54: 853-873, (1997), the disclosure of which is incorporated by reference herein in its entirety. In one embodiment the prostaglandin is selected from the group consisting of arbaprostil, alprostadil, beraprost, bimatoprost, carboprost, cloprostenol, dimoxaprost, dinoprost, enprostil, enisoprost, fluprostenol, fenprostalene, froxiprost, gemeprost, latanoprost, limaprost, meteneprost, mexiprostil, misoprostol, misoprost, misoprostol acid, nocloprost, ONO 373, ornoprostil, prostalene, PGE$_1$, PGE$_2$, PGF$_1$, PGF$_{2\alpha}$, rioprostil, rosaprostol, remiprostol, sulprostone, tafluprost, trimoprostil, tiprostanide, travoprost and unoprostone. PGE$_1$ compounds include, but are not limited to, alprostadil, misoprostol and enprostil and their α-cyclodextrin complexes. All the prostaglandins described herein can be modified to contain at least one nitric oxide enhancing group following the methods described herein.

The contemplated prostaglandin compounds of the invention are described more fully in the literature, such as in Goodman and Gilman, The Pharmacological Basis of Therapeutics (9th Edition), McGraw-Hill, (1996); Merck Index on CD-ROM, 13$^{th}$ Edition; STN Express, file phar and file registry, the disclosures of each of which are incorporated by reference herein in their entirety.

In one embodiment, the invention describes prostaglandins of Formula (I) and pharmaceutically acceptable salts thereof: wherein the compound of Formula (I) is:

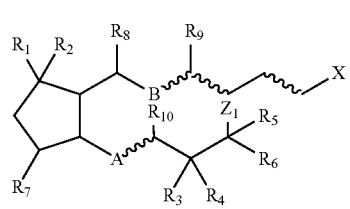

wherein ∼∼∼ indicates a single or a double bond;

R$_1$ is —OD$_1$ or —Cl;

R$_2$ and R$_8$ are a hydrogen; or R$_1$ and R$_2$ taken together are =CH$_2$ or =O;

R$_3$ and R$_4$ are each independently a hydrogen, a fluorine, —OD$_1$ or —CH$_3$; or R$_3$ and R$_4$ taken together are =O;

R$_5$ and R$_6$ are each independently a hydrogen, —OD$_1$, —CH$_3$, —OCH$_3$ or —CH=CH$_2$;

R$_7$ is a hydrogen or —OD$_1$;

R$_9$ is hydrogen or absent when the carbon to which it is attached is the central carbon of an allene functionality; or R$_8$ and R$_9$ taken together with the chain to which they are attached form a substituted benzene ring with the proviso that R$_1$ is an oxygen atom which is attached to the carbon atom at the position of the benzene ring defined by B;

R$_{10}$ is a hydrogen; or is absent when the carbon to which it is attached is —C≡;

A is —CH=, —CH$_2$, —S—, —O— or —C≡;

B is —CH=, —CH$_2$, —S—, or —C(O)—;

X is —CH$_2$OR$_{11}$, —C(O)OR$_{11}$ or —C(O)N(D$_1$)R$_{12}$;

R$_{11}$ is D$_1$, a lower alkyl group, or

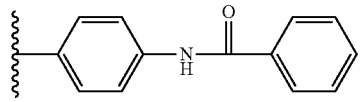 [SMILES: *c1ccc(NC(=O)c2ccccc2)cc1]

R$_{12}$ is a hydrogen, —C$_2$H$_5$; —S(O)$_2$CH$_3$ or —C(O)CH$_3$;

Z$_1$ is (a) an ethyl, (b) a butyl, (c) a hexyl, (d) a benzyl,

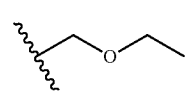

(e)

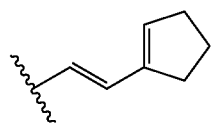

(f)

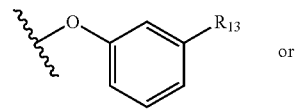

(g)

or

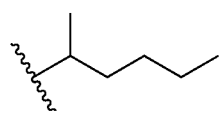

(h)

R$_{13}$ is a hydrogen, CF$_3$ or —Cl;

D$_1$ is a hydrogen or K; with the proviso that at least one D$_1$ in formula (I) must be a nitric oxide enhancing group;

K is —(W$_3$)$_a$-E$_b$-(C(R$_e$)(R$_f$))$_{p1}$-E$_c$-(C(R$_e$)(R$_f$))$_x$—(W$_3$)$_d$—(C(R$_e$)R$_f$))$_y$—(W$_3$)$_i$-E$_j$-(W$_3$)$_g$—(C(R$_e$)(R$_f$))$_z$—V$_4$;

a, b, c, d, g, i and j are each independently an integer from 0 to 3;

p$_1$, x, y and z are each independently an integer from 0 to 10;

V$_4$ is V$_3$, R$_e$, —U$_3$—V$_5$ or V$_6$;

V₃ is:
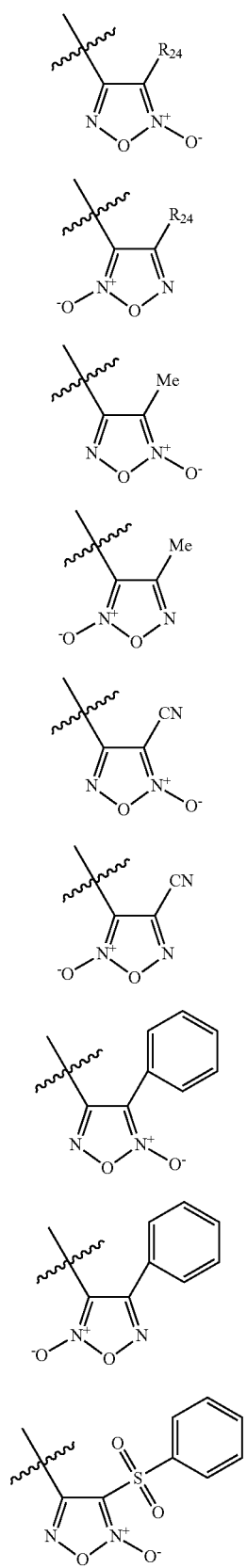
(1)
(2)
(3)
(4)
(5)
(6)
(7)
(8)
(9)
-continued
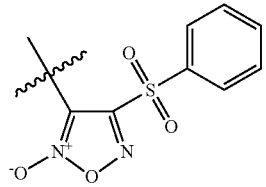
(10)
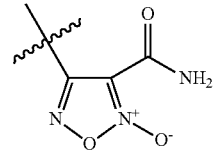
(11)
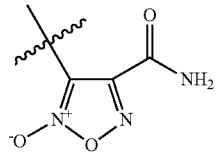
(12)
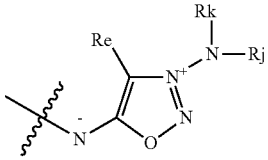
(13)
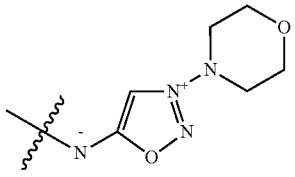
(14)
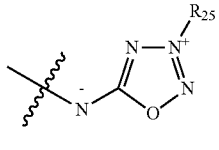
(15)
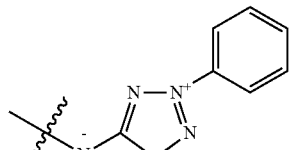
(16)
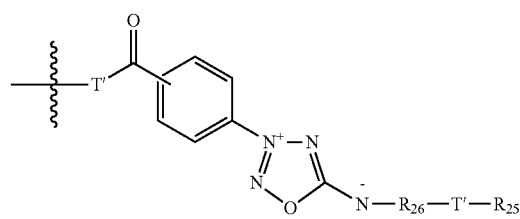
(17)

(18)
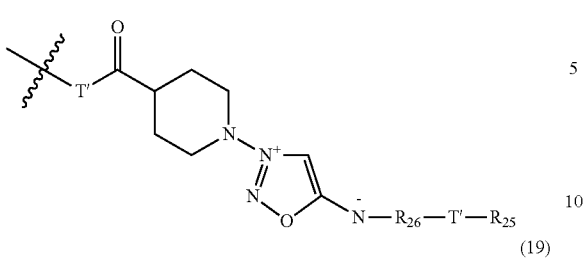

(19)
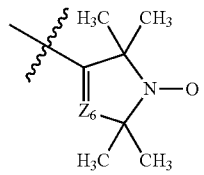

(2)
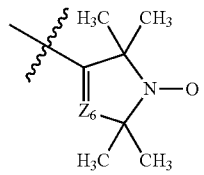

(3)
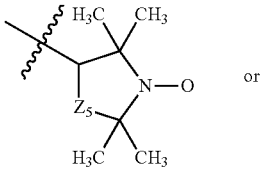
or (4)
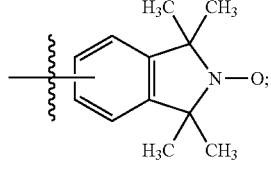

(20)
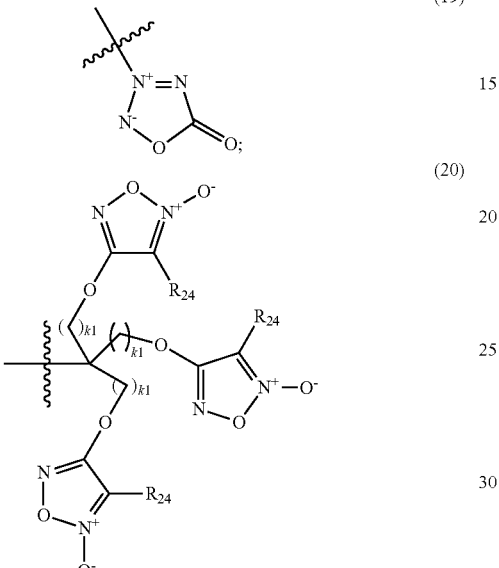

$Z_5$ is —CH$_2$ or oxygen;
$Z_6$ is —CH or nitrogen;
W$_3$ at each occurrence is independently —C(O)—, —C(S)—, —T$_3$—, —(C(R$_e$)(R$_f$))$_h$—, —N(R$_a$)R$_i$, an alkyl group, an aryl group, a heterocyclic ring, an arylheterocyclic ring, —(CH$_2$CH$_2$O)$_{q1}$— or a heterocyclic nitric oxide donor;
E at each occurrence is independently —T$_3$—, an alkyl group, an aryl group, —(C(R$_e$)(R$_f$))$_h$—, a heterocyclic ring, an arylheterocyclic ring, —(CH$_2$CH$_2$O)$_{q1}$— or Y$_4$;
Y$_4$ is:

(21)
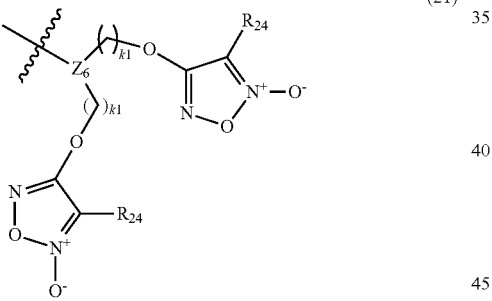

(1)
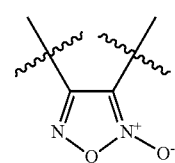

(2)
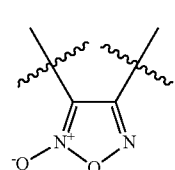

(3)
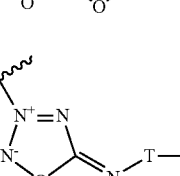

R$_{24}$ is —C$_6$H$_4$R$_{37}$, —CN, —S(O)$_2$—C$_6$H$_4$R$_{37}$, —C(O)—N(R$_a$)(R$_i$), —NO$_2$, —C(O)—OR$_{25}$ or —S(O)$_2$—R$_{25}$;
R$_{25}$ is an aryl group, a lower alkyl group, a haloalkyl group, a hydroxyalkyl group or an arylalkyl group;
R$_{26}$ is —C(O)— or —S(O)$_2$—;
R$_{37}$ is a hydrogen, —CN, —S(O)$_2$—R$_{25}$, —C(O)—N(R$_a$)(R$_i$), —NO$_2$ or —C(O)—OR$_{25}$;
T' is oxygen, sulfur or NR$_{16}$;
R$_{16}$ is a hydrogen, a lower alkyl group, or an aryl group;
V$_6$ is:

(1)
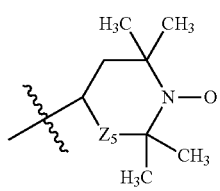

(4)
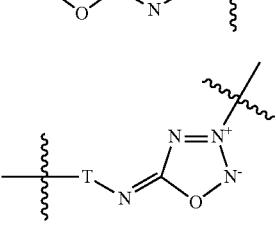

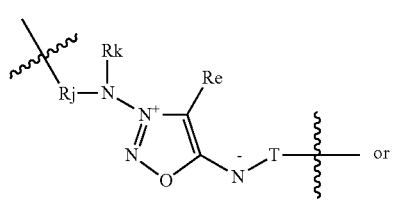
(5)

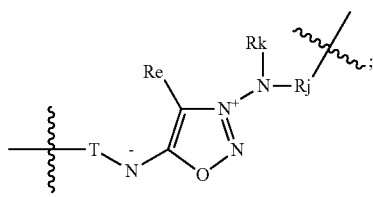
(6)

T is a —S(O)$_o$—; a carbonyl or a covalent bond;

o is an integer from 0 to 2;

R$_j$ and R$_k$ are independently selected from an alkyl group, an aryl group, or R$_j$ and R$_k$ taken together with the nitrogen atom to which they are attached are a heterocylic ring;

T$_3$ at each occurrence is independently a covalent bond, a carbonyl, an oxygen, —S(O)$_o$— or —N(R$_a$)R$_i$;

h is an integer form 1 to 10;

q$_1$ is an integer from 1 to 5;

R$_e$ and R$_f$ are each independently a hydrogen, an alkyl, a cycloalkoxy, a halogen, a hydroxy, an hydroxyalkyl, an alkoxyalkyl, an arylheterocyclic ring, an alkylaryl, an alkylcycloalkyl, an alkylheterocyclic ring, a cycloalkylalkyl, a cycloalkylthio, an arylalklythio, an arylalklythioalkyl, an alkylthioalkyl, a cycloalkenyl, an heterocyclicalkyl, an alkoxy, a haloalkoxy, an amino, an alkylamino, a dialkylamino, an arylamino, a diarylamino, an alkylarylamino, an alkoxyhaloalkyl, a sulfonic acid, a sulfonic ester, an alkylsulfonic acid, an arylsulfonic acid, an arylalkoxy, an alkylthio, an arylthio, a cyano, an aminoalkyl, an aminoaryl, an aryl, an arylalkyl, an alkylaryl, a carboxamido, an alkylcarboxamido, an arylcarboxamido, an amidyl, a carboxyl, a carbamoyl, an alkylcarboxylic acid, an arylcarboxylic acid, an alkylcarbonyl, an arylcarbonyl, an ester, a carboxylic ester, an alkylcarboxylic ester, an arylcarboxylic ester, a sulfonamido, an alkylsulfonamido, an arylsulfonamido, an alkylsulfonyl, an alkylsulfonyloxy, an arylsulfonyl, arylsulphonyloxy, a sulfonic ester, an alkyl ester, an aryl ester, a urea, a phosphoryl, a nitro, —U$_3$—V$_5$, V$_6$, —(C(R$_o$)(R$_p$))$_{k1}$—U$_3$—V$_5$, —(C(R$_o$)(R$_p$))$_{k1}$—U$_3$—V$_3$, —(C(R$_o$)(R$_p$))$_{k1}$—U$_3$—V$_6$, —(C(R$_o$)(R$_p$))$_{k1}$—U$_3$—C(O)—V$_6$, or R$_e$ and R$_f$ taken together with the carbons to which they are attached form a carbonyl, a methanthial, a heterocyclic ring, a cycloalkyl group, an aryl group, an oxime, an imine, a hydrazone a bridged cycloalkyl group,

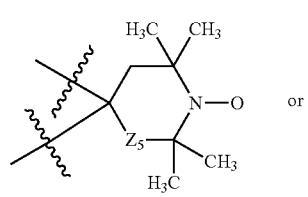
(1)

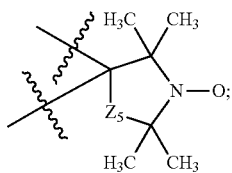
(2)

R$_o$ and R$_p$ are each independently a hydrogen, an alkyl, a cycloalkoxy, a halogen, a hydroxy, an hydroxyalkyl, an alkoxyalkyl, an arylheterocyclic ring, an alkylaryl, an alkylcycloalkyl, an alkylheterocyclic ring, a cycloalkylalkyl, a cycloalkylthio, an arylalklythio, an arylalklythioalkyl, an alkylthioalkyl a cycloalkenyl, an heterocyclicalkyl, an alkoxy, a haloalkoxy, an amino, an alkylamino, a dialkylamino, an arylamino, a diarylamino, an alkylarylamino, an alkoxyhaloalkyl, a sulfonic acid, a sulfonic ester, an alkylsulfonic acid, an arylsulfonic acid, an arylalkoxy, an alkylthio, an arylthio, a cyano an aminoalkyl, an aminoaryl, an aryl, an arylalkyl, an alkylaryl, a carboxamido, an alkylcarboxamido, an arylcarboxamido, an amidyl, a carboxyl, a carbamoyl, an alkylcarboxylic acid, an arylcarboxylic acid, an alkylcarbonyl, an arylcarbonyl, an ester, a carboxylic ester, an alkylcarboxylic ester, an arylcarboxylic ester, a sulfonamido, an alkylsulfonamido, an arylsulfonamido, an alkylsulfonyl, an alkylsulfonyloxy, an arylsulfonyl, arylsulphonyloxy, a sulfonic ester, an alkyl ester, an aryl ester, a urea, a phosphoryl, a nitro, —U$_3$—V$_5$, V$_6$, or R$_o$ and R$_p$ taken together with the carbons to which they are attached form a carbonyl, a methanthial, a heterocyclic ring, a cycloalkyl group, an aryl group, an oxime, an imine, a hydrazone a bridged cycloalkyl group,

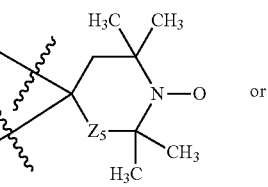
(1)

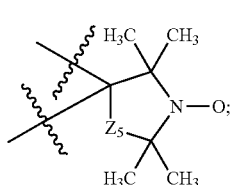
(2)

U$_3$ is an oxygen, sulfur or —N(R$_a$)R$_i$;

V$_5$ is —NO or —NO$_2$ (i.e. an oxidized nitrogen);

k$_1$ is an integer from 1 to 3;

R$_a$ is a lone pair of electrons, a hydrogen or an alkyl group;

R$_i$ is a hydrogen, an alkyl, an aryl, an alkylcarboxylic acid, an arylcarboxylic acid, an alkylcarboxylic ester, an arylcarboxylic ester, an alkylcarboxamido, an arylcarboxamido, an alkylaryl, an alkylsulfinyl, an alkylsulfonyl, an alkylsulfonyloxy, an arylsulfinyl, an arylsulfonyl, an arylsulphonyloxy, a sulfonamido, a carboxamido, a carboxylic ester, an aminoalkyl, an aminoaryl, —CH$_2$—C—(U$_3$—V$_5$)(R$_e$)(R$_f$), a bond to an adjacent atom creating a double bond to that atom or —(N$_2$O$_2$—).M$_1^+$, wherein M$_1^+$ is an organic or inorganic cation; and with the proviso that the prostaglandin compound of Formula (I) must contain at least heterocyclic nitric oxide donor group and/or nitroxide group linked to the prostaglandin compound of Formula (I) through an oxygen atom, a nitrogen atom or a sulfur atom via a bond or moiety that can be hydrolyzed.

In cases where multiple designations of variables which reside in sequence are chosen as a "covalent bond" or the integer chosen is 0, the intent is to denote a single covalent bond connecting one radical to another. For example, $E_0$ would denote a covalent bond, while $E_2$ denotes (E-E) and $(C(R_4)(R_4))_2$ denotes —C(R_4)(R_4)—C(R_4)(R_4)—.

The compound of Formula (I) that contains at least one nitric oxide enhancing group linked to the compound of Formula (I) through an oxygen atom, a nitrogen atom or a sulfur atom via a bond or moiety that can be hydrolyzed are prodrugs of the parent prostaglandin compound and can be hydrolyzed to give the parent prostaglandin compound and a moiety that contains the nitric oxide enhancing group.

In other embodiments of the invention the compound of Formula (I) is a nitric oxide enhancing arbaprostil analogue, a nitric oxide enhancing alprostadil analogue, a nitric oxide enhancing bimatoprost analogue, a nitric oxide enhancing carboprost analogue, a nitric oxide enhancing cloprostenol analogue, a nitric oxide enhancing dimoxaprost analogue, a nitric oxide enhancing dinoprost analogue, a nitric oxide enhancing enprostil analogue, a nitric oxide enhancing enisoprost analogue, a nitric oxide enhancing fenprostalene analogue, a nitric oxide enhancing froxiprost analogue, a nitric oxide enhancing gemeprost analogue, a nitric oxide enhancing latanoprost analogue, a nitric oxide enhancing meteneprost analogue, a nitric oxide enhancing mexiprostil analogue, a nitric oxide enhancing misoprostol analogue, a nitric oxide enhancing misoprostil analogue, a nitric oxide enhancing misoprostol acid analogue, a nitric oxide enhancing nocloprost analogue, a nitric oxide enhancing ONO 373 analogue, a nitric oxide enhancing ornoprostil analogue, a nitric oxide enhancing prostalene analogue, a nitric oxide enhancing $PGE_1$ analogue, a nitric oxide enhancing $PGE_2$ analogue, a nitric oxide enhancing $PGF_1$ analogue, a nitric oxide enhancing $PGF_{2\alpha}$ analogue, a nitric oxide enhancing rioprostil analogue, a nitric oxide enhancing rosaprostol analogue, a nitric oxide enhancing remiprostol analogue, a nitric oxide enhancing sulprostone analogue, a nitric oxide enhancing tafluprost analogue, a nitric oxide enhancing travoprost analogue, a nitric oxide enhancing trimoprostil analogue, a nitric oxide enhancing tiprostanide analogue, a nitrosated unoprostone analogue, and pharmaceutically acceptable salts thereof.

In other embodiments of the invention the compound of Formula (I) is a nitric oxide enhancing arbaprostil analogue of Formula (II), a nitric oxide enhancing alprostadil or $PGE_1$ analogue of Formula (III), a nitric oxide enhancing bimatoprost analogue of Formula (IV), a nitric oxide enhancing carboprost analogue of Formula (V), a nitric oxide enhancing cloprostenol analogue of Formula (VI), a nitric oxide enhancing dimoxaprost analogue of Formula (VII), a nitric oxide enhancing dinoprost analogue of Formula (VIII), a nitric oxide enhancing enprostil analogue of Formula (IX), a nitric oxide enhancing enisoprost analogue of Formula (X), a nitric oxide enhancing fenprostalene analogue of Formula (XI), a nitric oxide enhancing froxiprost analogue of Formula (XII), a nitric oxide enhancing gemeprost analogue of Formula (XIII), a nitric oxide enhancing latanoprost analogue of Formula (XIV), a nitric oxide enhancing meteneprost analogue of Formula (XV), a nitric oxide enhancing mexiprostil analogue of Formula (XVI), a nitric oxide enhancing misoprostol analogue of Formula (XVII), a nitric oxide enhancing misoprostol acid analogue of Formula (XVIII), a nitric oxide enhancing nocloprost analogue of Formula (XIX), a nitric oxide enhancing ONO 373 analogue of Formula (XX), a nitric oxide enhancing ornoprostil analogue of Formula (XXI), a nitric oxide enhancing prostalene analogue of Formula (XXII), a nitric oxide enhancing $PGE_2$ analogue of Formula (XXIII), a nitric oxide enhancing $PGF_1$ analogue of Formula (XXIV), a nitric oxide enhancing $PGF_{2\alpha}$ analogue of Formula (XXV), a nitric oxide enhancing rioprostil analogue of Formula (XXVI), a nitric oxide enhancing rosaprostol analogue of Formula (XXVII), a nitric oxide enhancing remiprostol analogue of Formula (XXVIII), a nitric oxide enhancing sulprostone analogue of Formula (XXIX), a nitric oxide enhancing tafluprost analogue of Formula (XXX), a nitric oxide enhancing travoprost analogue of Formula (XXXI), a nitric oxide enhancing trimoprostil analogue of Formula (XXXII), a nitric oxide enhancing tiprostanide analogue of Formula (XXXIII), a nitric oxide enhancing unoprostone analogue of Formula (XXXIV), and pharmaceutically acceptable salts thereof:

wherein the compound of Formula (II) is:

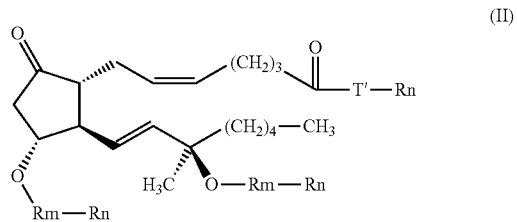

(II)

wherein the compound of Formula (III) is:

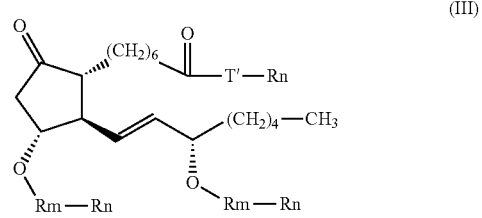

(III)

wherein the compound of Formula (IV) is:

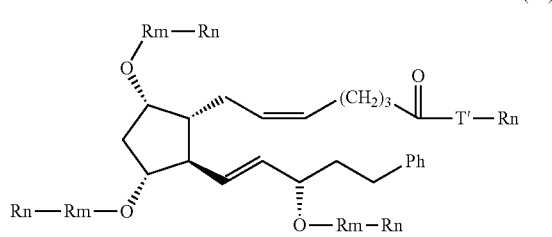

(IV)

wherein the compound of Formula (V) is:

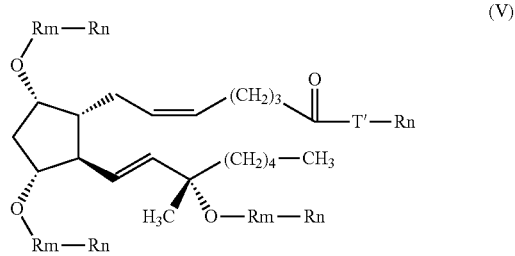

(V)

wherein the compound of Formula (VI) is:

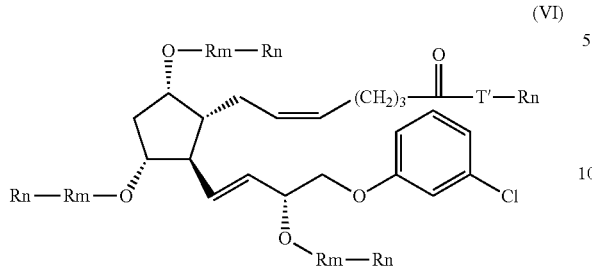
(VI)

wherein the compound of Formula (VII) is:

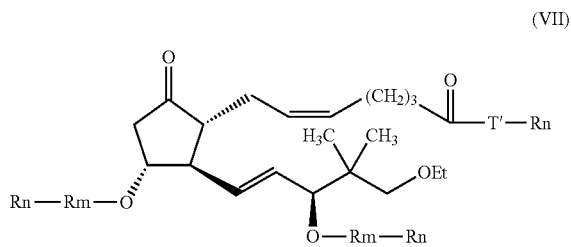
(VII)

wherein the compound of Formula (VIII) is:

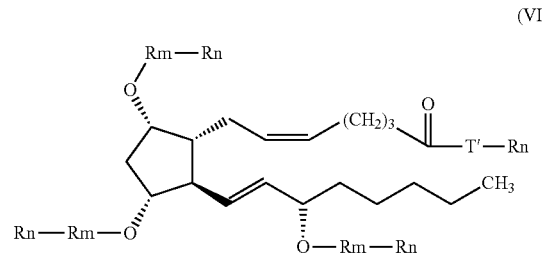
(VIII)

wherein the compound of Formula (IX) is:

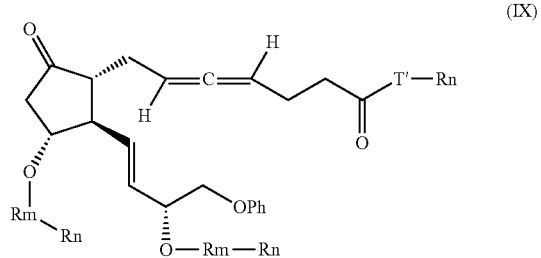
(IX)

wherein the compound of Formula (X) is:

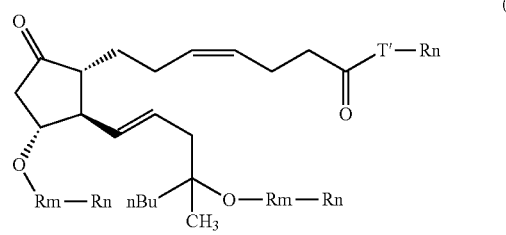
(X)

wherein the compound of Formula (XI) is:

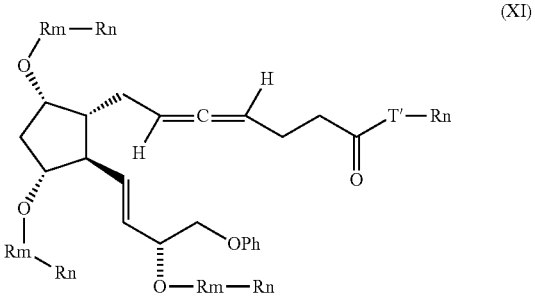
(XI)

wherein the compound of Formula (XII) is:

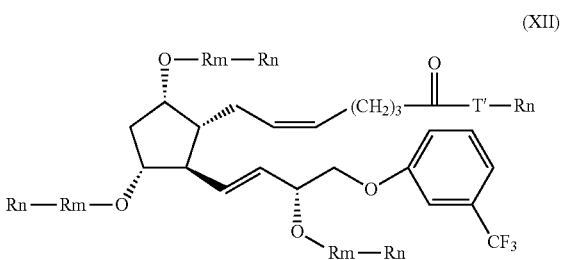
(XII)

wherein the compound of Formula (XIII) is:

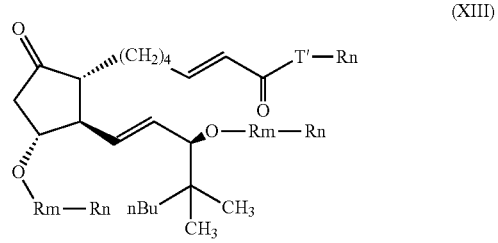
(XIII)

wherein the compound of Formula (XIV) is:

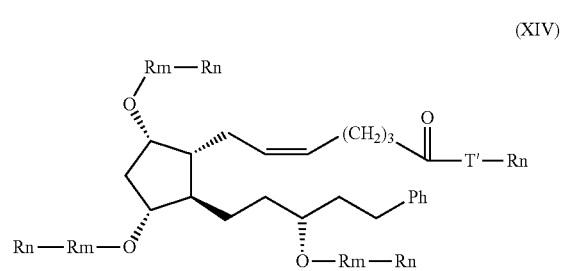
(XIV)

wherein the compound of Formula (XV) is:

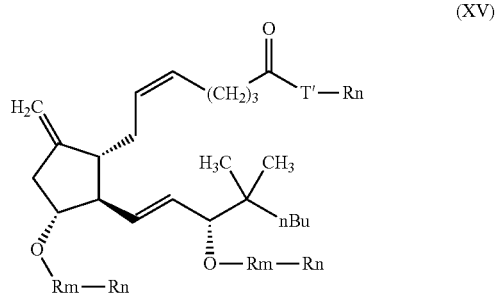
(XV)

wherein the compound of Formula (XVI) is:

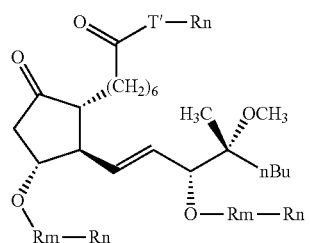
(XVI)

wherein the compound of Formula (XVII) is:

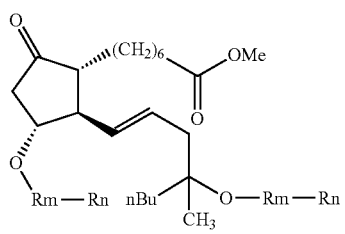
(XVII)

wherein the compound of Formula (XVIII) is:

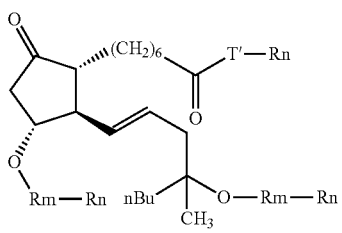
(XVIII)

wherein the compound of Formula (XIX) is:

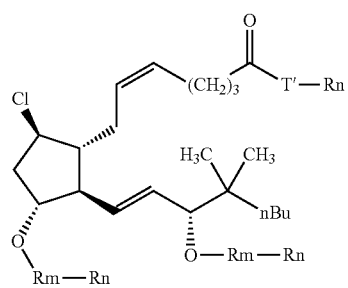
(XIX)

wherein the compound of Formula (XX) is:

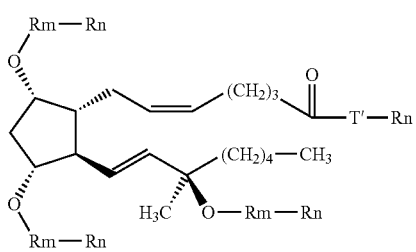
(XX)

wherein the compound of Formula (XXI) is:

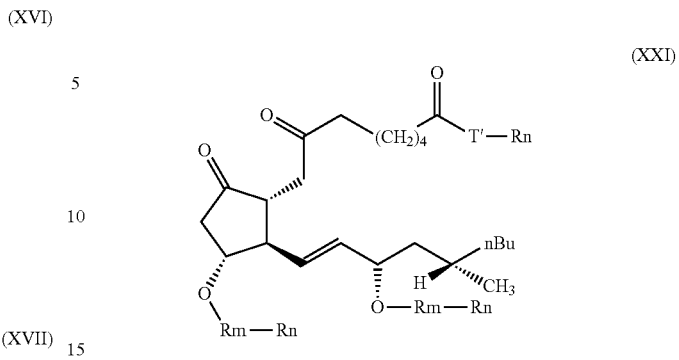
(XXI)

wherein the compound of Formula (XXII) is:

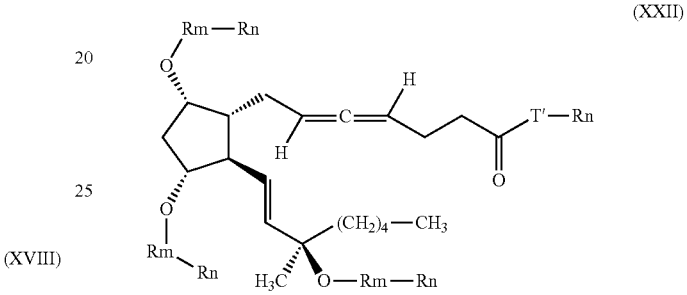
(XXII)

wherein the compound of Formula (XXIII) is:

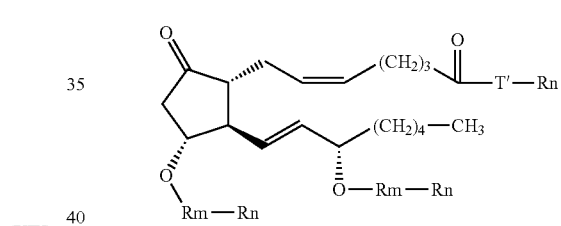
(XXIII)

wherein the compound of Formula (XXIV) is:

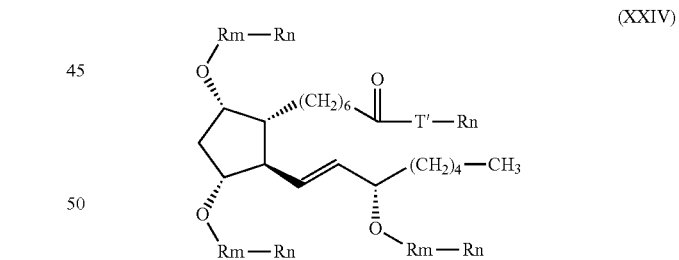
(XXIV)

wherein the compound of Formula (XXV) is:

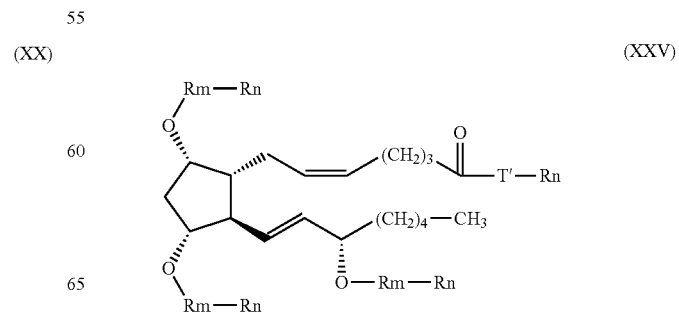
(XXV)

wherein the compound of Formula (XXVI) is:

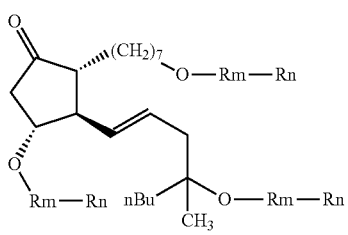
(XXVI)

wherein the compound of Formula (XXVII) is:

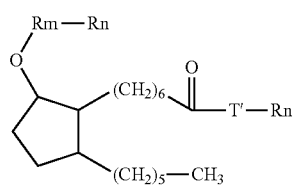
(XXVII)

wherein the compound of Formula (XXVIII) is:

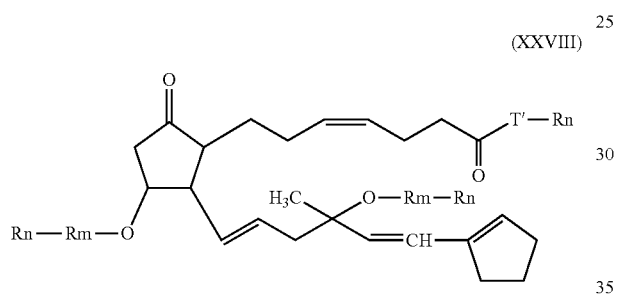
(XXVIII)

wherein the compound of Formula (XXIX) is:

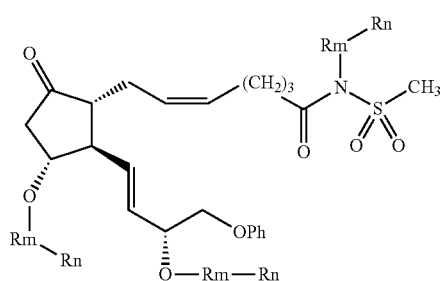
(XXIX)

wherein the compound of Formula (XXX) is:

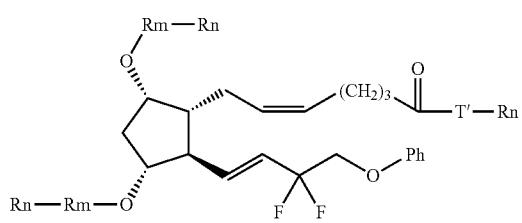
(XXX)

wherein the compound of Formula (XXXI) is:

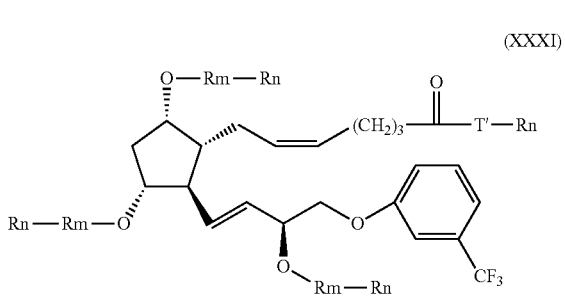
(XXXI)

wherein the compound of Formula (XXXII) is:

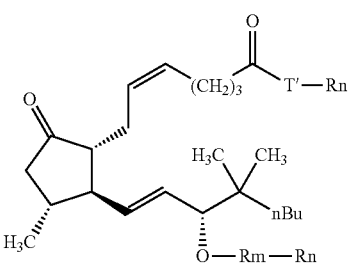
(XXXII)

wherein the compound of Formula (XXXIII) is:

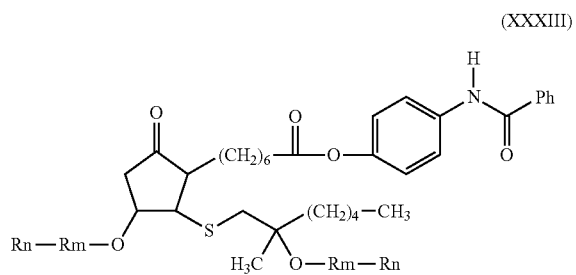
(XXXIII)

wherein the compound of Formula (XXXIV) is:

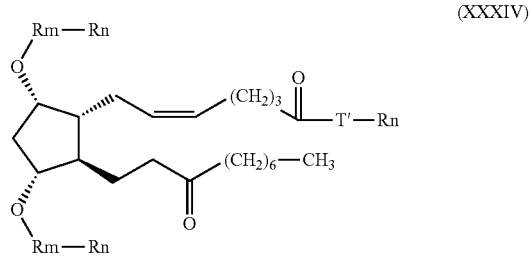
(XXXIV)

wherein
T' is oxygen, sulfur or $NR_{16}$;
nBu is the lower alkyl group $CH_3$—$CH_2$—$CH_2$—$CH_2$—;
OEt is the alkoxy group —$OCH_2$—$CH_3$;
OPh is the alkoxy group —$OC_6H_5$;
Ph is a aryl group —$C_6H_5$;
$R_{16}$ is a hydrogen, a lower alkyl group, an aryl group;

wherein
$R_m$—$R_n$ taken together are a hydrogen atom; or
$R_m$ is:
(i) —C—(O)—;
(ii) —C—(O)—NR$_{16}$;
(iii) —C(O)—O—;
(iv) —C(O)—S;
(v) —CH$_2$—O—;
(vi) —CH(CH$_3$)—O—;
(vii) a covalent bond;
(viii) —(C—(R$_e$)(R$_f$))$_{2-5}$—;
(ix) —(C—(R$_e$)(R$_f$))$_{2-5}$-T'-;
(x) —(C—(R$_e$)(R$_f$))$_{2-5}$—T'—C(O)—; or
(xi) —N—C(O)—S—;
(xii) —N—C(O)—CH$_2$—;
(xiii) —N—C(O)—O—;
$R_n$ is:
a hydrogen or:
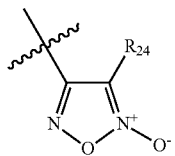
(1)
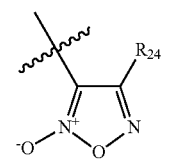
(2)
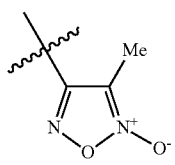
(3)
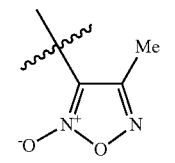
(4)
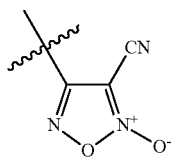
(5)
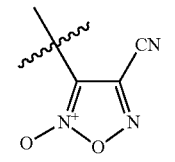
(6)
-continued
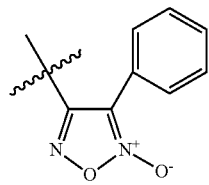
(7)
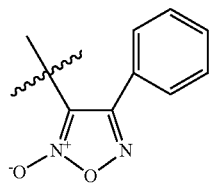
(8)
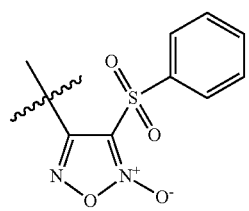
(9)
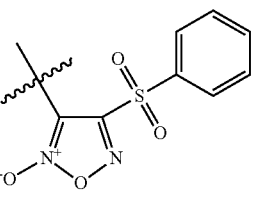
(10)
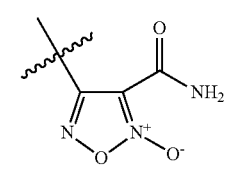
(11)
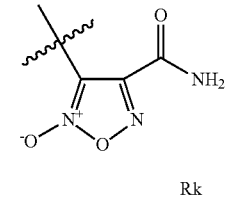
(12)
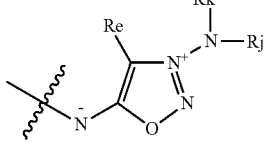
(13)
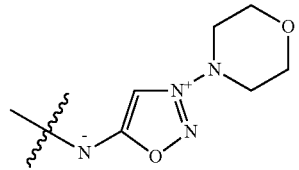
(14)
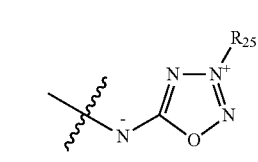
(15)

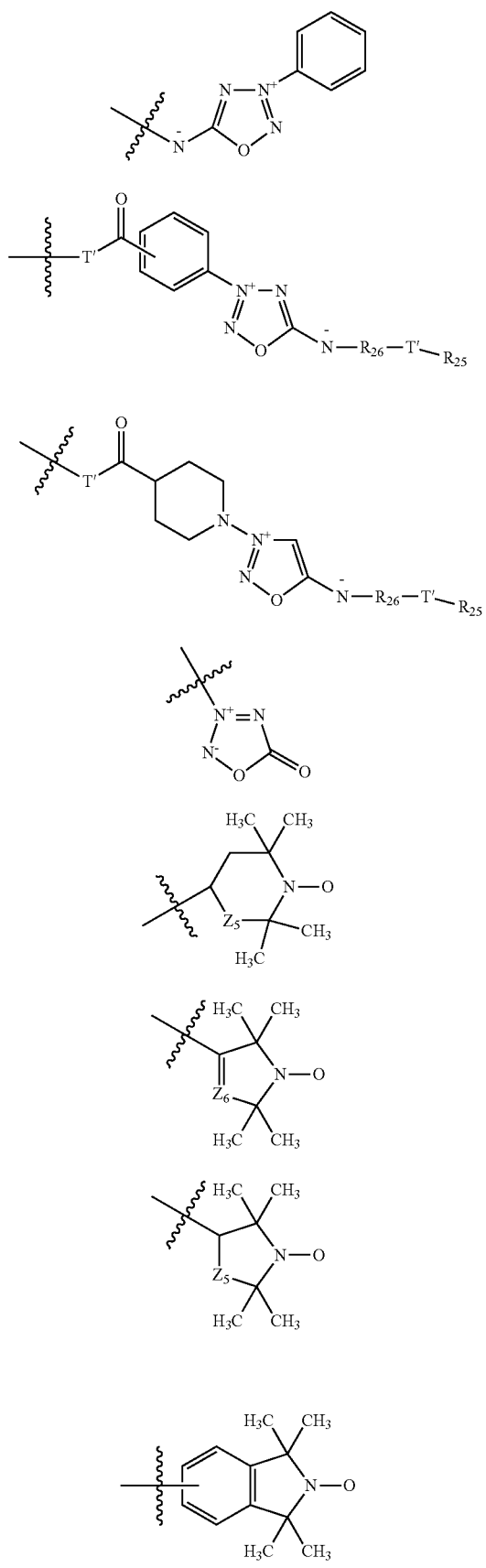

$Z_5$ is —$CH_2$ or oxygen;
$Z_6$ is —CH or nitrogen;
$R_{24}$ is —$C_6H_4R_{37}$, —CN, —$S(O)_2$—$C_6H_4R_{37}$, —C(O)—$N(R_a)(R_i)$, —$NO_2$, —C(O)—$OR_{25}$ or —$S(O)_2$—$R_{25}$;
$R_{25}$ is an aryl group, a lower alkyl group, a haloalkyl group, a hydroxyalkyl group or an arylalkyl group;
$R_{26}$ is —C(O)— or —$S(O)_2$—;
$R_{37}$ is a hydrogen, —CN, —$S(O)_2$—$R_{25}$, —C(O)—$N(R_a)(R_i)$, —$NO_2$ or —C(O)—$OR_{25}$;
T' is oxygen, sulfur or $NR_{16}$;
$R_{16}$ is a hydrogen, a lower alkyl group, or an aryl group;
$k_1$ is an integer from 1 to 3;
$R_j$ and $R_k$ are independently selected from an alkyl group, an aryl group, or $R_j$ and $R_k$ taken together with the nitrogen atom to which they are attached are a heterocylic ring; and with the proviso that the compounds of Formula (II) to Formula (XXXIV) must contain at least one nitric oxide enhancing group linked to the compounds of Formula (II) to Formula (XXXIV) via a bond or moiety that can be hydrolyzed.

In other embodiments of the invention the compound of Formula (I) is a nitric oxide enhancing arbaprostil analogue of Formula (XXXV), a nitric oxide enhancing alprostadil or $PGE_1$ analogue of Formula (XXXVI), a nitric oxide enhancing bimatoprost analogue of Formula (XXXVII), a nitric oxide enhancing carboprost analogue of Formula (XXXVIII), a nitric oxide enhancing cloprostenol analogue of Formula (XXXIX), a nitric oxide enhancing dimoxaprost analogue of Formula (XL), a nitric oxide enhancing dinoprost analogue of Formula (XLI), a nitric oxide enhancing enprostil analogue of Formula (XLII), a nitric oxide enhancing enisoprost analogue of Formula (XLIII), a nitric oxide enhancing fenprostalene analogue of Formula (XLIV), a nitric oxide enhancing froxiprost analogue of Formula (XLV), a nitric oxide enhancing gemeprost analogue of Formula (XLVI), a nitric oxide enhancing latanoprost analogue of Formula (XLVII), a nitric oxide enhancing meteneprost analogue of Formula (XLVIII), a nitric oxide enhancing mexiprostil analogue of Formula (XLIX), a nitric oxide enhancing misoprostol analogue of Formula (L), a nitric oxide enhancing misoprostol acid analogue of Formula (LI), a nitric oxide enhancing nocloprost analogue of Formula (LII), a nitric oxide enhancing ONO 373 analogue of Formula (LIII), a nitric oxide enhancing ornoprostil analogue of Formula (LIV), a nitric oxide enhancing prostalene analogue of Formula (LV), a nitric oxide enhancing $PGE_2$ analogue of Formula (LVI), a nitric oxide enhancing $PGF_1$ analogue of Formula (LVII), a nitric oxide enhancing $PGF_{2\alpha}$ analogue of Formula (LVIII), a nitric oxide enhancing rioprostil analogue of Formula (LIX), a nitric oxide enhancing rosaprostol analogue of Formula (LX), a nitric oxide enhancing remiprostol analogue of Formula (LXI), a nitric oxide enhancing sulprostone analogue of Formula (LXII), a nitric oxide enhancing tafluprost analogue of Formula (LXIII), a nitric oxide enhancing travoprost analogue of Formula (LXIV), a nitric oxide enhancing trimoprostil analogue of Formula (LXV), a nitric oxide enhancing tiprostanide analogue of Formula (LXVI), a nitric oxide enhancing unoprostone analogue of Formula (LXVII), and pharmaceutically acceptable salts thereof;

wherein the compound of Formula (XXXV) is:

(XXXV)

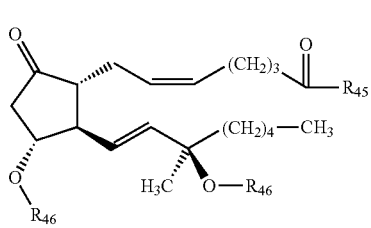

wherein the compound of Formula (XXXVI) is:

(XXXVI)

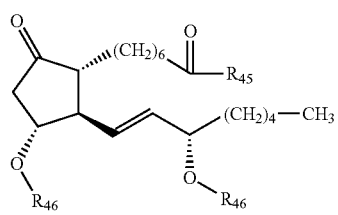

wherein the compound of Formula (XXXVII) is:

(XXXVII)

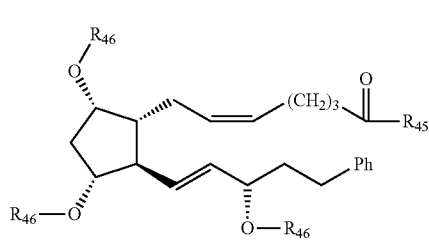

wherein the compound of Formula (XXXVIII) is:

(XXXVIII)

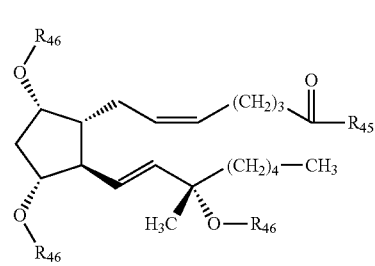

wherein the compound of Formula (XXXIX) is:

(XXXIX)

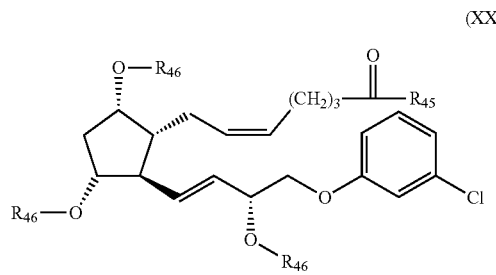

wherein the compound of Formula (XL) is:

(XL)

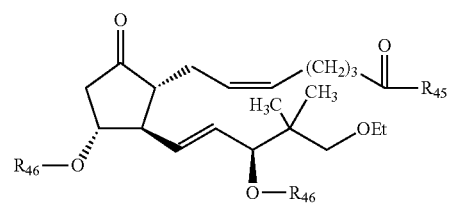

wherein the compound of Formula (XLI) is:

(XLI)

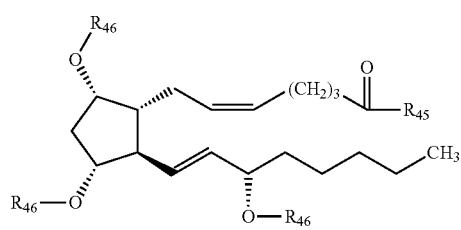

wherein the compound of Formula (XLII) is:

(XLII)

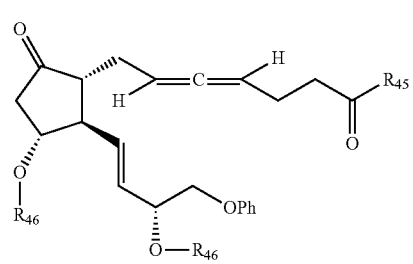

wherein the compound of Formula (XLIII) is:

(XLIII)

wherein the compound of Formula (XLIV) is:

(XLIV)

wherein the compound of Formula (XLV) is:

(XLV)

wherein the compound of Formula (XLVI) is:

(XLVI)

wherein the compound of Formula (XLVII) is:

(XLVII)

wherein the compound of Formula (XLVIII) is:

(XLVIII)

wherein the compound of Formula (XLIX) is:

(XLIX)

wherein the compound of Formula (L) is:

(L)

wherein the compound of Formula (LI) is:

(LI)

wherein the compound of Formula (LII) is:

(LII)

wherein the compound of Formula (LIII) is:

(LIII)

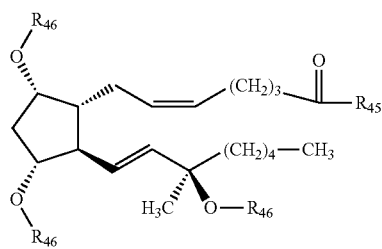

wherein the compound of Formula (LIV) is:

(LIV)

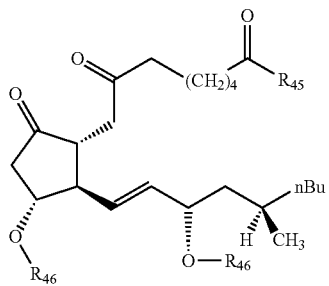

wherein the compound of Formula (LV) is:

(LV)

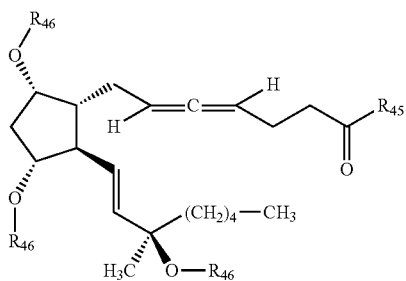

wherein the compound of Formula (LVI) is:

(LVI)

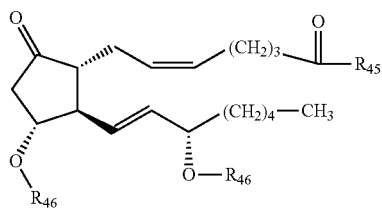

wherein the compound of Formula (LVII) is:

(LVII)

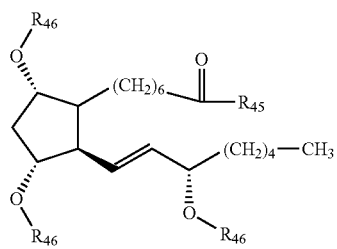

wherein the compound of Formula (LVIII) is:

(LVIII)

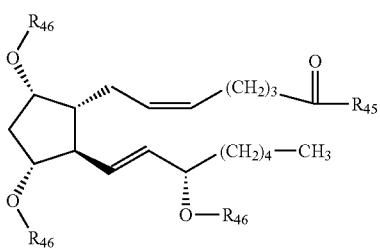

wherein the compound of Formula (LIX) is:

(LIX)

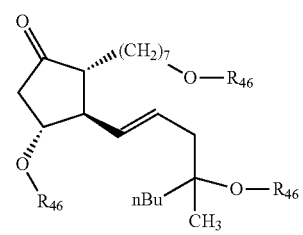

wherein the compound of Formula (LX) is:

(L)

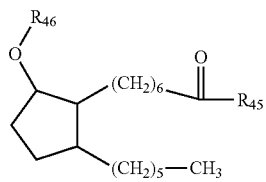

wherein the compound of Formula (LXI) is:

(LI)

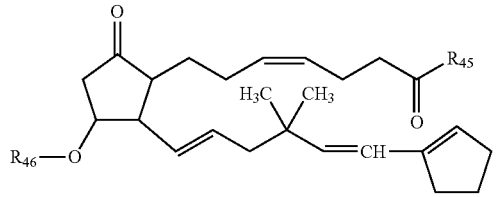

wherein the compound of Formula (LXII) is:

(LXII)

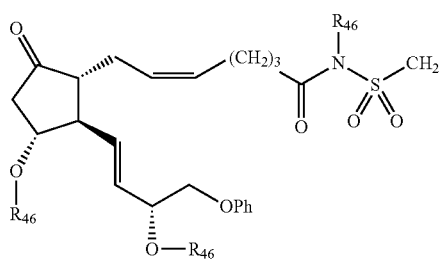

wherein the compound of Formula (LXIII) is:

(LXIII)
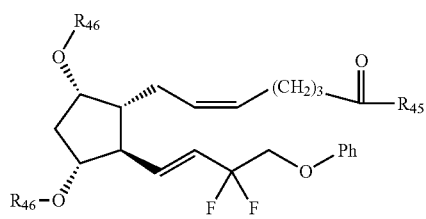

wherein the compound of Formula (LXIV) is:

(LXIV)
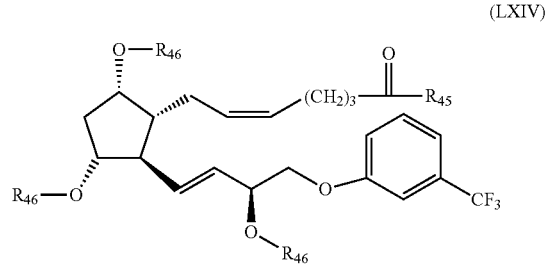

wherein the compound of Formula (LXV) is:

(LXV)
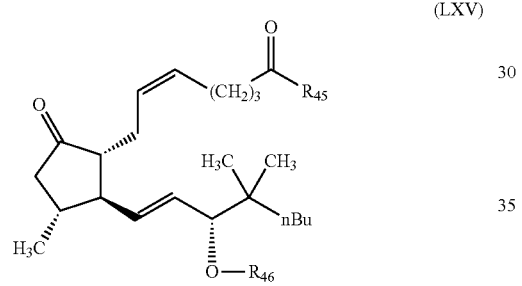

wherein the compound of Formula (LXVI) is:

(LXVI)
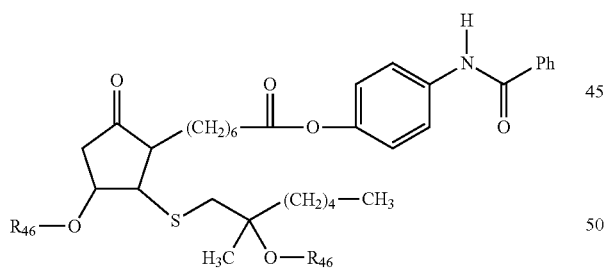

wherein the compound of Formula (LXVII) is:

(LXVII)
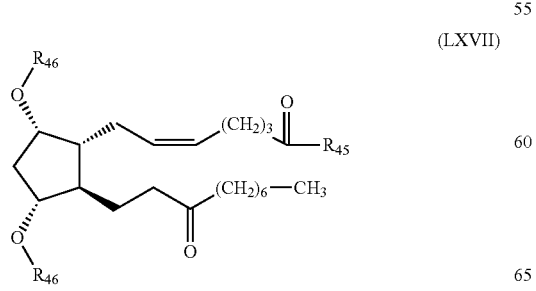

wherein:
nBu is the lower alkyl group $CH_3-CH_2-CH_2-CH_2-$;
OMe is the alkoxy group $-O-CH_3$;
OEt is the alkoxy group $-OCH_2-CH_3$;
OPh is the alkoxy group $-OC_6H_5$;
Ph is an aryl group $-C_6H_5$;
$R_{45}$ is:

(1)
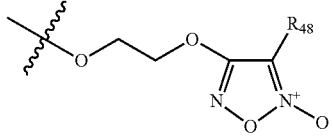

(2)
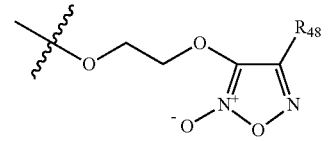

(3)
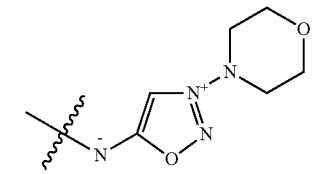

(4)
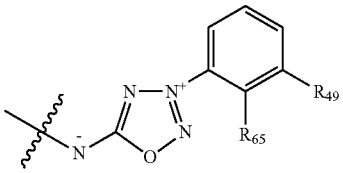

(5)
—OH;

(6)
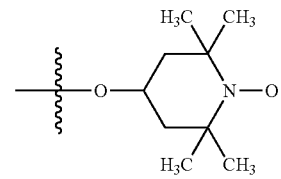

(7)
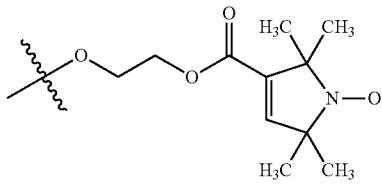

(8)
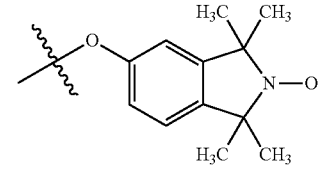

(9)
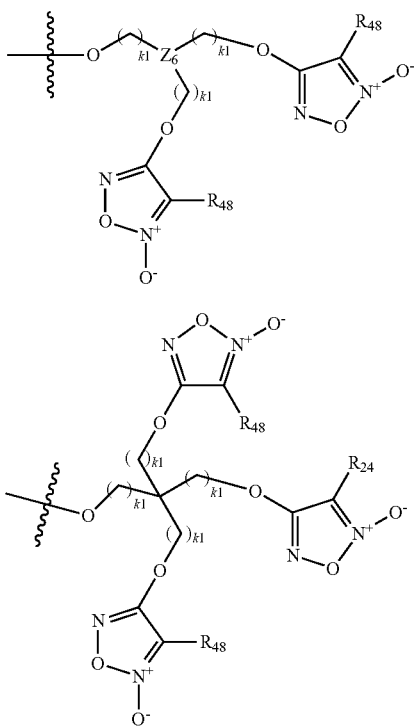
(10)
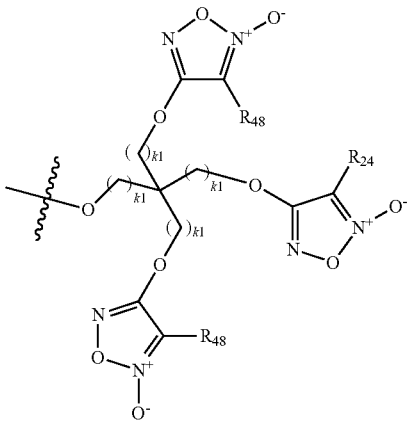
$R_{48}$ is —S(O)$_2$—C$_6$H$_5$; —CN, —C(O)—NH$_2$ or —C(O)OCH$_3$, and
$R_{49}$ is a hydrogen or chlorine;
$R_{65}$ is a hydrogen or a methyl group;
$k_1$ is an integer from 1 to 3;
$Z_6$ is CH or nitrogen;
$R_{46}$ is:
(1)
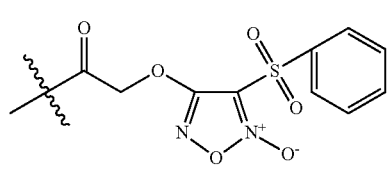
(2)
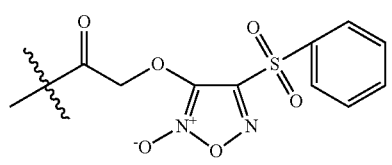
(3)
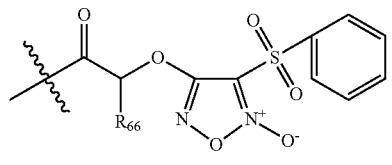
(4)
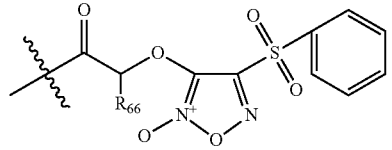
(5)
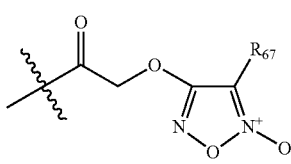
(6)
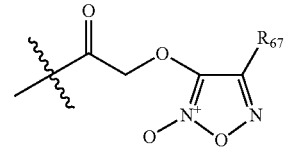
(7)
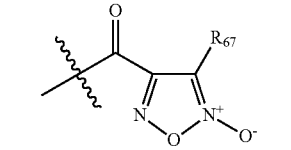
(8)
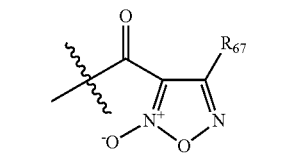
(9)
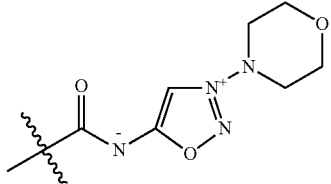
(10)
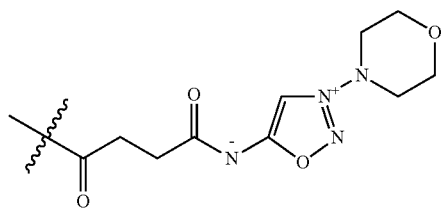
(11)
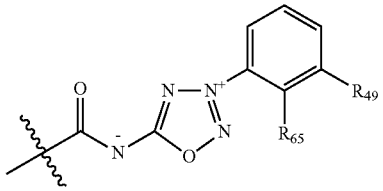
(12)
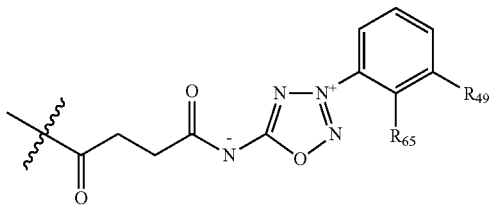

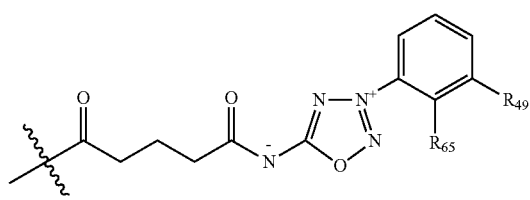
(13)

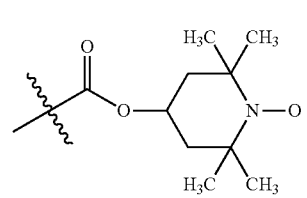
(14) H;

(15)
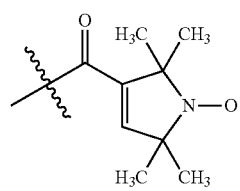

(16)
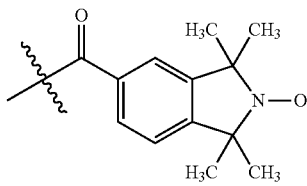

(17)
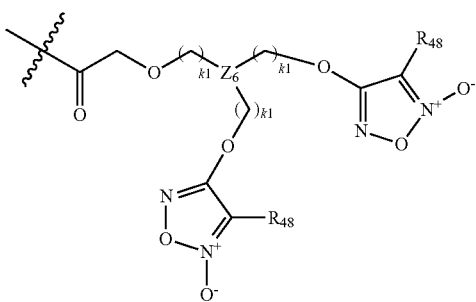

(18)
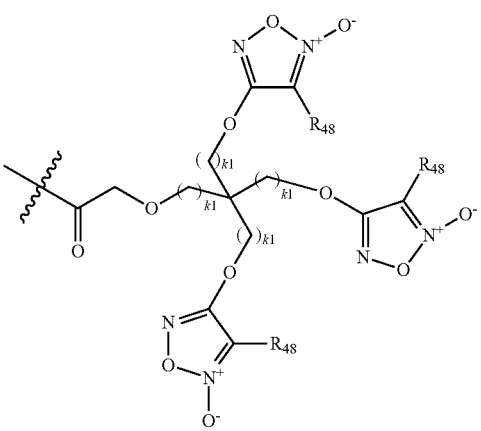

(19)

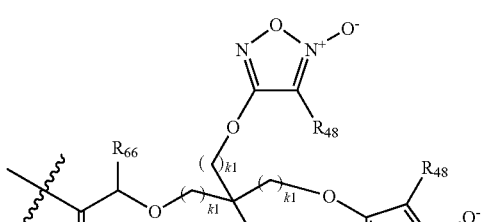
(20)

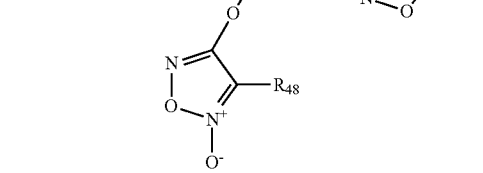
(21)

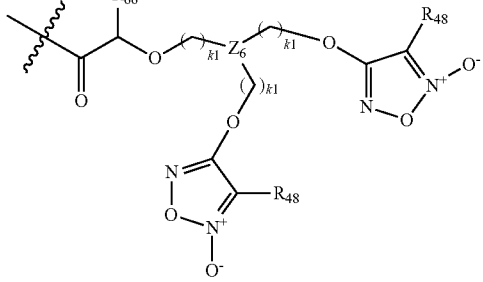

wherein:

$R_{66}$ is —$(CH_2)_2$—O—C(O)—$CH_3$ or —$(CH_2)_2$—NH—C(O)—$CH_3$;

$R_{67}$ is —CN, —C(O)—$NH_2$ or —C(O)—$OCH_3$;

$R_{49}$, $R_{65}$, $Z_6$ and $k_1$ are as defined herein; and with the proviso that the compounds of Formula (XXXV) to (LXVII) must contain at least one nitric oxide enhancing group linked to the compounds of Formula (XXXV) to (LXVII) via a bond or moiety that can be hydrolyzed.

Compounds of the invention that have one or more asymmetric carbon atoms may exist as the optically pure enantiomers, pure diastereomers, mixtures of enantiomers, mixtures of diastereomers, racemic mixtures of enantiomers, diastereomeric racemates or mixtures of diastereomeric racemates. It is to be understood that the invention anticipates and includes within its scope all such isomers and mixtures thereof.

Another embodiment of the invention describes the metabolites of the nitric oxide enhancing prostaglandin compounds and pharmaceutically acceptable salts thereof. These metabolites, include but are not limited to, the non-nitric oxide enhancing derivatives, degradation products, hydrolysis products, and the like, of the nitric oxide enhancing prostaglandin compounds and pharmaceutically acceptable salts thereof.

Another embodiment of the invention provides processes for making the novel compounds of the invention and to the intermediates useful in such processes. The reactions are performed in solvents appropriate to the reagents and materials used are suitable for the transformations being effected. It is understood by one skilled in the art of organic synthesis that the functionality present in the molecule must be consistent with the chemical transformation proposed. This will, on occasion, necessitate judgment by the routineer as to the order of synthetic steps, protecting groups required, and deprotection conditions. Substituents on the starting materials may be incompatible with some of the reaction conditions required in some of the methods described, but alternative methods and substituents compatible with the reaction conditions will be readily apparent to one skilled in the art. The use of sulfur and oxygen protecting groups is well known for protecting thiol and alcohol groups against undesirable reactions during a synthetic procedure and many such protecting groups are known and described by, for example, Greene and Wuts, *Protective Groups in Organic Synthesis*, Third Edition, John Wiley & Sons, New York (1999).

The chemical reactions described herein are generally disclosed in terms of their broadest application to the preparation of the compounds of this invention. Occasionally, the reactions may not be applicable as described to each compound included within the disclosed scope. The compounds for which this occurs will be readily recognized by one skilled in the art. In all such cases, either the reactions can be successfully performed by conventional modifications known to one skilled in the art, e.g., by appropriate protection of interfering groups, by changing to alternative conventional reagents, by routine modification of reaction conditions, and the like, or other reactions disclosed herein or otherwise conventional, will be applicable to the preparation of the corresponding compounds of this invention. In all preparative methods, all starting materials are known or readily prepared from known starting materials.

The compounds of Formulas (I) to (LVII) can be synthesized by one skilled in the art using conventional methods. Some of the parent prostaglandin compounds (i.e. prostaglandin compounds that do not contain a nitric oxide enhancing group) are commercially available or their synthesis has been reported in the scientific literature. The prostaglandin compounds that are substituted to contain a nitric oxide enhancing group linked to the prostaglandin compound through one or more sites such as oxygen, sulfur and/or nitrogen via a bond or moiety that can be hydrolyzed, can be synthesized using conventional methods known to one skilled in the art. Known methods for linking the nitric oxide enhancing groups to compounds are described in WO 99/64417, WO 94/01422; EP 0 574 726 A1, EP 0 683 159 A1; and in *J. Med. Chem.*, 47: 2688-2693 (2004); *J. Med. Chem.*, 47: 1840-1846 (2004); *J. Med. Chem.*, 46: 3762-3765 (2003); *J. Med. Chem.*, 46: 747-754 (2003); *Chem. Rev.*, 102: 1091-1134 (2002); J. Med. Chem., 42: 1941-1950 (1999); *J. Med. Chem.*, 41: 5393-5401 (1998); *J. Med. Chem.*, 38: 4944-4949 (1995); *Arzneim. Forsch. Drug Res.*, 47 (II): 847-854 (1997); the disclosures of each of which are incorporated by reference herein in their entirety. The methods of linking the nitric oxide enhancing group to compounds described in these references can be applied by one skilled in the art to produce any of the nitric oxide enhancing prostaglandin compounds described herein. The prostaglandin compounds of the invention comprising at least one nitric oxide enhancing group donate or transfer a biologically active form of nitrogen monoxide (i.e., nitric oxide).

Compounds contemplated for use in the invention, e.g., prostaglandin compounds that contain at least one nitric oxide enhancing group, linked through one or more sites such as oxygen (hydroxyl condensation), sulfur (sulfhydryl condensation) and/or nitrogen, via a bond or moiety that is hydrolyzed, are, optionally, used in combination with nitric oxide enhancing compounds that release nitric oxide, increase endogeneous levels of nitric oxide or otherwise directly or indirectly deliver or transfer a biologically active form of nitrogen monoxide to a site of its intended activity, such as on a cell membrane in vivo.

Nitrogen monoxide can exist in three forms: NO– (nitroxyl), NO. (nitric oxide) and NO+ (nitrosonium). NO. is a highly reactive short-lived species that is potentially toxic to cells. This is critical because the pharmacological efficacy of NO depends upon the form in which it is delivered. In contrast to the nitric oxide radical (NO.), nitrosonium (NO+) does not react with $O_2$ or $O_2$— species, and functionalities capable of transferring and/or releasing NO+ and NO— are also resistant to decomposition in the presence of many redox metals. Consequently, administration of charged NO equivalents (positive and/or negative) does not result in the generation of toxic by-products or the elimination of the active NO group.

The term "nitric oxide" encompasses uncharged nitric oxide (NO.) and charged nitrogen monoxide species, preferably charged nitrogen monoxide species, such as nitrosonium ion (NO+) and nitroxyl ion (NO–). The reactive form of nitric oxide can be provided by gaseous nitric oxide. The nitrogen monoxide releasing, delivering or transferring compounds have the structure F—NO, wherein F is a nitrogen monoxide releasing, delivering or transferring group, and include any and all such compounds which provide nitrogen monoxide to its intended site of action in a form active for its intended purpose.

The term "NO adducts" encompasses any nitrogen monoxide releasing, delivering or transferring compounds, including, for example, S-nitrosothiols, nitrites, nitrates, S-nitrothiols, sydnonimines, 2-hydroxy-2-nitrosohydrazines, (NONOates), (E)-alkyl-2-((E)-hydroxyimino)-5-nitro-3-hexeneamide (FK-409), (E)-alkyl-2((E)-hydroxyimino)-5-nitro-3-hexeneamines, N-((2Z,3E)-4-ethyl-2-(hydroxyimino)-6-methyl-5-nitro-3-heptenyl)-3-pyridinecarboxamide (FR 146801), N-nitrosoamines, N-hydroxyl nitrosamines, nitrosimines, diazetine dioxides, oxatriazole 5-imines, oximes, hydroxylamines, N-hydroxyguanidines, hydroxyureas, benzofuroxanes, furoxans as well as substrates for the endogenous enzymes which synthesize nitric oxide.

Suitable NONOates include, but are not limited to, (Z)-1-(N-methyl-N-(6-(N-methyl-ammoniohexyl)amino))diazen-1-ium-1,2-diolate ("MAHMA/NO"), (Z)-1-(N-(3-ammoniopropyl)-N-(n-propyl)amino)diazen-1-ium-1,2-diolate ("PAPA/NO"), (Z)-1-(N-(3-aminopropyl)-N-(4-(3-aminopropylammonio)butyl)-amino)diazen-1-ium-1,2-diolate (spermine NONOate or "SPER/NO") and sodium(Z)-1-(N,N-diethylamino)diazenium-1,2-diolate (diethylamine NONOate or "DEA/NO") and derivatives thereof. NONOates are also described in U.S. Pat. Nos. 6,232,336, 5,910,316 and 5,650,447, the disclosures of which are incorporated herein by reference in their entirety. The "NO adducts" can be mono-nitrosylated, poly-nitrosylated, mono-nitrosated and/or poly-nitrosated at a variety of naturally susceptible or artificially provided binding sites for biologically active forms of nitrogen monoxide.

Suitable furoxanes include, but are not limited to, CAS 1609, C93-4759, C92-4678, S35b, CHF 2206, CHF 2363, and the like.

Suitable sydnonimines include, but are not limited to, molsidomine (N-ethoxycarbonyl-3-morpholinosydnonimine), SIN-1 (3-morpholinosydnonimine) CAS 936 (3-(cis-2,6-dimethylpiperidino)-N-(4-methoxybenzoyl)-sydnonimine, pirsidomine), C87-3754 (3-(cis-2,6-dimethylpiperidino)sydnonimine, linsidomine, C4144 (3-(3,3-dimethyl-1,4-thiazane-4-yl)sydnonimine hydrochloride), C89-4095 (3-(3,3-dimethyl-1,1-dioxo-1,4-thiazane-4-yl)sydnonimine hydrochloride, and the like.

Suitable oximes include, but are not limited to, NOR-1, NOR-3, NOR-4, and the like.

One group of NO adducts is the S-nitrosothiols, which are compounds that include at least one —S—NO group. These compounds include S-nitroso-polypeptides (the term "polypeptide" includes proteins and polyamino acids that do not possess an ascertained biological function, and derivatives thereof); S-nitrosylated amino acids (including natural and synthetic amino acids and their stereoisomers and racemic mixtures and derivatives thereof); S-nitrosylated sugars; S-nitrosylated, modified and unmodified, oligonucleotides (preferably of at least 5, and more preferably 5-200 nucleotides); straight or branched, saturated or unsaturated, aliphatic or aromatic, substituted or unsubstituted S-nitrosylated hydrocarbons; and S-nitroso heterocyclic compounds. S-nitrosothiols and methods for preparing them are described in U.S. Pat. Nos. 5,380,758 and 5,703,073; WO 97/27749; WO 98/19672; and Oae et al, Org. Prep. Proc. Int., 15(3): 165-198 (1983), the disclosures of each of which are incorporated by reference herein in their entirety.

Another embodiment of the invention is S-nitroso amino acids where the nitroso group is linked to a sulfur group of a sulfur-containing amino acid or derivative thereof. Such compounds include, for example, S-nitroso-N-acetylcysteine, S-nitroso-captopril, S-nitroso-N-acetylpenicillamine, S-nitroso-homocysteine, S-nitroso-cysteine, S-nitroso-glutathione, S-nitroso-cysteinyl-glycine, and the like.

Suitable S-nitrosylated proteins include thiol-containing proteins (where the NO group is attached to one or more sulfur groups on an amino acid or amino acid derivative thereof) from various functional classes including enzymes, such as tissue-type plasminogen activator (TPA) and cathepsin B; transport proteins, such as lipoproteins; heme proteins, such as hemoglobin and serum albumin; and biologically protective proteins, such as immunoglobulins, antibodies and cytokines Such nitrosylated proteins are described in WO 93/09806, the disclosure of which is incorporated by reference herein in its entirety. Examples include polynitrosylated albumin where one or more thiol or other nucleophilic centers in the protein are modified.

Other examples of suitable S-nitrosothiols include:
(i) HS(C($R_e$)($R_f$))$_m$SNO;
(ii) ONS(C($R_e$)($R_f$))$_m R_e$; or
(iii) $H_2N$—CH($CO_2H$)—($CH_2$)$_m$—C(O)NH—CH($CH_2$SNO)—C(O)NH—$CH_2$—$CO_2H$;
wherein m is an integer from 2 to 20;

$R_e$ and $R_f$ are each independently a hydrogen, an alkyl, a cycloalkoxy, a halogen, a hydroxy, an hydroxyalkyl, an alkoxyalkyl, an arylheterocyclic ring, an alkylaryl, an alkylcycloalkyl, an alkylheterocyclic ring, a cycloalkylalkyl, a cycloalkylthio, an arylalklythio, an arylalklythioalkyl, an alkylthioalkyl, a cycloalkenyl, an heterocyclicalkyl, an alkoxy, a haloalkoxy, an amino, an alkylamino, a dialkylamino, an arylamino, a diarylamino, an alkylarylamino, an alkoxyhaloalkyl, a sulfonic acid, a sulfonic ester, an alkylsulfonic acid, an arylsulfonic acid, an arylalkoxy, an alkylthio, an arylthio, a cyano, an aminoalkyl, an aminoaryl, an aryl, an arylalkyl, an alkylaryl, a carboxamido, an alkylcarboxamido, an arylcarboxamido, an amidyl, a carboxyl, a carbamoyl, an alkylcarboxylic acid, an arylcarboxylic acid, an alkylcarbonyl, an arylcarbonyl, an ester, a carboxylic ester, an alkylcarboxylic ester, an arylcarboxylic ester, a sulfonamido, an alkylsulfonamido, an arylsulfonamido, an alkylsulfonyl, an alkylsulfonyloxy, an arylsulfonyl, arylsulphonyloxy, a sulfonic ester, an alkyl ester, an aryl ester, a urea, a phosphoryl, a nitro, —$U_3$—$V_5$, $V_6$, —(C($R_o$)($R_p$))$_{k1}$—$U_3$—$V_5$, —(C($R_o$)($R_p$))$_{k1}$—$U_3$—$V_6$, —(C($R_o$)($R_p$))$_{k1}$—$U_3$—C(O)—$V_6$, or $R_e$ and $R_f$ taken together with the carbons to which they are attached form a carbonyl, a methanthial, a heterocyclic ring, a cycloalkyl group, an aryl group, an oxime, a hydrazone, a bridged cycloalkyl group,

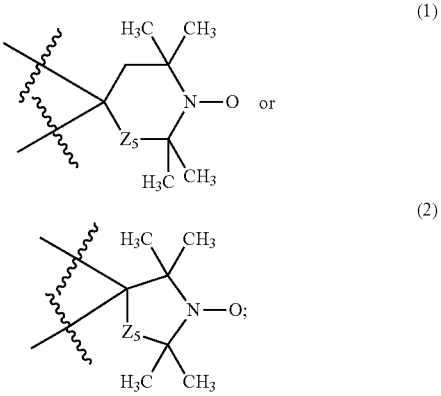

$R_o$ and $R_p$ are each independently a hydrogen, an alkyl, a cycloalkoxy, a halogen, a hydroxy, an hydroxyalkyl, an alkoxyalkyl, an arylheterocyclic ring, an alkylaryl, an alkylcycloalkyl, an alkylheterocyclic ring, a cycloalkylalkyl, a cycloalkylthio, an arylalklythio, an arylalklythioalkyl, an alkylthioalkyl a cycloalkenyl, an heterocyclicalkyl, an alkoxy, a haloalkoxy, an amino, an alkylamino, a dialkylamino, an arylamino, a diarylamino, an alkylarylamino, an alkoxyhaloalkyl, a sulfonic acid, a sulfonic ester, an alkylsulfonic acid, an arylsulfonic acid, an arylalkoxy, an alkylthio, an arylthio, a cyano, an aminoalkyl, an aminoaryl, an aryl, an arylalkyl, an alkylaryl, a carboxamido, an alkylcarboxamido, an arylcarboxamido, an amidyl, a carboxyl, a carbamoyl, an alkylcarboxylic acid, an arylcarboxylic acid, an alkylcarbonyl, an arylcarbonyl, an ester, a carboxylic ester, an alkylcarboxylic ester, an arylcarboxylic ester, a sulfonamido, an alkylsulfonamido, an arylsulfonamido, an alkylsulfonyl, an alkylsulfonyloxy, an arylsulfonyl, arylsulphonyloxy, a sulfonic ester, an alkyl ester, an aryl ester, a urea, a phosphoryl, a nitro, —$U_3$—$V_5$, $V_6$, or $R_o$ and $R_p$ taken together with the carbons to which they are attached form a carbonyl, a methanthial, a heterocyclic ring, a cycloalkyl group, an aryl group, an oxime, an imine, a hydrazone, a bridged cycloalkyl group,

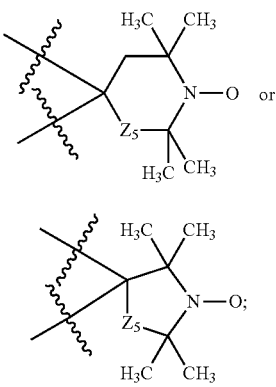

$k_1$ is an integer form 1 to 3;
$U_3$ is an oxygen, sulfur- or —N($R_a$)$R_i$;
$V_5$ is —NO or —$NO_2$ (i.e. an oxidized nitrogen);
$R_a$ is a lone pair of electrons, a hydrogen or an alkyl group;

$R_i$ is a hydrogen, an alkyl, an aryl, an alkylcarboxylic acid, an arylcarboxylic acid, an alkylcarboxylic ester, an arylcarboxylic ester, an alkylcarboxamido, an arylcarboxamido, an alkylaryl, an alkylsulfinyl, an alkylsulfonyl, an alkylsulfonyloxy, an arylsulfinyl, an arylsulfonyl, arylsulphonyloxy, a sulfonamido, a carboxamido, a carboxylic ester, an aminoalkyl, an aminoaryl, —$CH_2$—$C(U_3$—$V_5)(R_e)(R_f)$, a bond to an adjacent atom creating a double bond to that atom or —$(N_2O_2\text{-})^-.M_1^+$, wherein $M_1^+$ is an organic or inorganic cation.

In cases where $R_e$ and $R_f$ are independently a heterocyclic ring or taken together $R_e$ and $R_f$ are a heterocyclic ring, then $R_i$ can be a substituent on any disubstituted nitrogen contained within the radical wherein $R_i$ is as defined herein.

Nitrosothiols can be prepared by various methods of synthesis. In general, the thiol precursor is prepared first, then converted to the S-nitrosothiol derivative by nitrosation of the thiol group with $NaNO_2$ under acidic conditions (pH is about 2.5) which yields the S-nitroso derivative. Acids which can be used for this purpose include aqueous sulfuric, acetic and hydrochloric acids. The thiol precursor can also be nitrosylated by reaction with an organic nitrite such as tert-butyl nitrite, or a nitrosonium salt such as nitrosonium tetrafluoroborate in an inert solvent.

Another group of NO adducts for use in the invention, where the NO adduct is a compound that donates, transfers or releases nitric oxide, include compounds comprising at least one ON—O— or ON—N— group. The compounds that include at least one ON—O— or ON—N— group are preferably ON—O— or ON—N-polypeptides (the term "polypeptide" includes proteins and polyamino acids that do not possess an ascertained biological function, and derivatives thereof); ON—O— or ON—N-amino acids (including natural and synthetic amino acids and their stereoisomers and racemic mixtures); ON—O— or ON—N-sugars; ON—O— or —ON—N— modified or unmodified oligonucleotides (comprising at least 5 nucleotides, preferably 5-200 nucleotides); ON—O— or ON—N— straight or branched, saturated or unsaturated, aliphatic or aromatic, substituted or unsubstituted hydrocarbons; and ON—O—, ON—N— or ON—C-heterocyclic compounds. Examples of compounds comprising at least one ON—O— or ON—N— group include butyl nitrite, isobutyl nitrite, tert-butyl nitrite, amyl nitrite, isoamyl nitrite, N-nitrosamines, N-nitrosamides, N-nitrosourea, N-nitrosoguanidines, N-nitrosocarbamates, N-acyl-N-nitroso compounds (such as, N-methyl-N-nitrosourea); N-hydroxy-N-nitrosamines, cupferron, alanosine, dopastin, 1,3-disubstituted nitrosiminobenzimidazoles, 1,3,4-thiadiazole-2-nitrosimines, benzothiazole-2 (3H)-nitrosimines, thiazole-2-nitrosimines, oligonitroso sydnonimines, 3-alkyl-N-nitroso-sydnonimines, 2H-1,3,4-thiadiazine nitrosimines.

Another group of NO adducts for use in the invention include nitrates that donate, transfer or release nitric oxide, such as compounds comprising at least one $O_2N$—O—, $O_2N$—N— or $O_2N$—S— group. Among these compounds are $O_2N$—O—, $O_2N$—N— or $O_2N$—S— polypeptides (the term "polypeptide" includes proteins and also polyamino acids that do not possess an ascertained biological function, and derivatives thereof); $O_2N$—O—, $O_2N$—N— or $O_2N$—S— amino acids (including natural and synthetic amino acids and their stereoisomers and racemic mixtures); $O_2N$—O—, $O_2N$—N— or $O_2N$—S— sugars; $O_2N$—O—, $O_2N$—N— or $O_2N$—S— modified and unmodified oligonucleotides (comprising at least 5 nucleotides, preferably 5-200 nucleotides); $O_2N$—O—, $O_2N$—N— or $O_2N$—S-straight or branched, saturated or unsaturated, aliphatic or aromatic, substituted or unsubstituted hydrocarbons; and $O_2N$—O—, $O_2N$—N— or $O_2N$—S— heterocyclic compounds. Examples of compounds comprising at least one $O_2N$—O—, $O_2N$—N— or $O_2N$—S— group include isosorbide dinitrate, isosorbide mononitrate, clonitrate, erythrityl tetranitrate, mannitol hexanitrate, nitroglycerin, pentaerythritoltetranitrate, pentrinitrol, propatylnitrate and organic nitrates with a sulfhydryl-containing amino acid such as, for example SPM 3672, SPM 4757, SPM 5185, SPM 5186 and those disclosed in U.S. Pat. Nos. 5,284,872, 5,428,061, 5,661,129, 5,807,847 and 5,883,122 and in WO 97/46521, WO 00/54756 and in WO 03/013432, the disclosures of each of which are incorporated by reference herein in their entirety.

Another group of NO adducts are N-oxo-N-nitrosoamines that donate, transfer or release nitric oxide and are represented by the formula: $R^{1''}R^{2''}N$—$N(O\text{-}M^+)$-NO, where $R^{1''}$ and $R^{2''}$ are each independently a polypeptide, an amino acid, a sugar, a modified or unmodified oligonucleotide, a straight or branched, saturated or unsaturated, aliphatic or aromatic, substituted or unsubstituted hydrocarbon, or a heterocyclic group, and where $M_1^+$ is an organic or inorganic cation, such as, for example, an alkyl substituted ammonium cation or a Group I metal cation.

The invention is also directed to compounds that stimulate endogenous NO or elevate levels of endogenous endothelium-derived relaxing factor (EDRF) in vivo or are oxidized to produce nitric oxide and/or are substrates for nitric oxide synthase and/or cytochrome P450. Such compounds include, for example, L-arginine, L-homoarginine, and N-hydroxy-L-arginine, N-hydroxy-L-homoarginine, N-hydroxydebrisoquine, N-hydroxypentamidine including their nitrosated and/or nitrosylated analogs (e.g., nitrosated L-arginine, nitrosylated L-arginine, nitrosated N-hydroxy-L-arginine, nitrosylated N-hydroxy-L-arginine, nitrosated and nitrosylated L-homoarginine), N-hydroxyguanidine compounds, amidoxime, ketoximes, aldoxime compounds, that can be oxidized in vivo to produce nitric oxide. Compounds that may be substrates for a cytochrome P450, include, for example, imino(benzylamino)methylhydroxyl amine, imino(((4-methylphenyl)methyl)amino)methylhydroxylamine, imino(((4-methoxyphenyl)methyl)amino) methylhydroxylamine, imino(((4-(trifluoromethyl)phenyl)methyl)amino) methylhydroxylamine, imino(((4-nitrophenyl)methyl)amino)methylhydroxylamine, (butylamino) iminomethylhydroxylamine, imino (propylamino) methylhydroxylamine, imino(pentylamino)methylhydroxylamine, imino (propylamino)methylhydroxylamine, imino ((methylethyl)amino)methylhydroxylamine, (cyclopropylamino) iminomethylhydroxylamine, imino-2-1,2,3,4-tetrahydroisoquinolyl methylhydroxylamine, imino(1-methyl(2-1,2,3,4-tetrahydroisoquinolyl)) methylhydroxylamine, (1,3-dimethyl(2-1,2,3,4-tetrahydroisoquinolyl)) iminomethylhydroxylamine, (((4-chlorophenyl)methyl)amino)iminomethylhydroxylamine, ((4-chlorophenyl)amino) iminomethylhydroxylamine, (4-chlorophenyl)(hydroxyimino) methylamine, and 1-(4-chlorophenyl)-1-(hydroxyimino) ethane, and the like, precursors of L-arginine and/or physiologically acceptable salts thereof, including, for example, citrulline, ornithine, glutamine, lysine, polypeptides comprising at least one of these amino acids, inhibitors of the enzyme arginase (e.g., N-hydroxy-L-arginine and 2(S)-amino-6-boronohexanoic acid), nitric oxide mediators and/or physiologically acceptable salts thereof, including, for example, pyruvate, pyruvate precursors, α-keto acids having four or more carbon atoms, precursors of α-keto acids having four or more carbon atoms (as disclosed in WO 03/017996, the disclosure of which is incorporated herein in its entirety), and the substrates for nitric oxide synthase, cytokines, adenosin, bradykinin, calreticulin, bisacodyl, and phenolphthalein. EDRF is a vascular relaxing factor secreted by the endothelium, and has been identified as nitric oxide (NO) or a closely related derivative thereof (Palmer et al, *Nature,* 327:524-526 (1987); Ignarro et al, *Proc. Natl. Acad. Sci. USA,* 84:9265-9269 (1987)).

The invention is also directed to nitric oxide enhancing compounds that can increase endogenous nitric oxide. Such compounds, include for example, nitroxide containing compounds, include, but are not limited to, substituted 2,2,6,6-tetramethyl-1-piperidinyloxy compounds, substituted 2,2,5,5-tetramethyl-3-pyrroline-1-oxyl compounds, substituted 2,2,5,5-tetramethyl-1-pyrrolidinyloxyl compounds, substituted 1,1,3,3-tetramethylisoindolin-2-yloxyl compounds, substituted 2,2,4,4-tetramethyl-1-oxazolidinyl-3-oxyl compounds, substituted 3-imidazolin-1-yloxy, 2,2,5,5-tetramethyl-3-imidazolin-1-yloxyl compounds, OT-551, 4-hydroxy-2,2,6,6-tetramethyl-1-piperidinyloxy (tempol), and the like. Suitable substituents, include, but are not limited to, aminomethyl, benzoyl, 2-bromoacetamido, 2-(2-(2-bromoacetamido)ethoxy)ethylcarbamoyl, carbamoyl, carboxy, cyano, 5-(dimethylamino)-1-naphthalenesulfonamido, ethoxyfluorophosphinyloxy, ethyl, 5-fluoro-2,4-dinitroanilino, hydroxy, 2-iodoacetamido, isothiocyanato, isothiocyanatomethyl, methyl, maleimido, maleimidoethyl, 2-(2-maleimidoethoxy)ethylcarbamoyl, maleimidomethyl, maleimido, oxo, phosphonooxy, and the like.

The invention is also based on the discovery that compounds and compositions of the invention may be used in conjunction with other therapeutic agents for co-therapies, partially or completely, in place of other therapeutic agents, such as, for example, aldosterone antagonists, α-adrenergic receptor agonists, α-adrenergic receptor antagonists, β-adrenergic agonists, antidiabetic compounds, antimicrobial compounds, anti-hyperlipidemic drugs, angiotensin II antagonists, angiotensin-converting enzyme (ACE) inhibitors, antioxidants, antithrombotic and vasodilator drugs, β-adrenergic antagonists, calcium channel blockers, carbonic anhydrase inhibitors, diuretics, endothelin antagonists, hydralazine compounds, $H_2$ receptor antagonists, neutral endopeptidase inhibitors, nonsteroidal antiinflammatory compounds (NSAIDs), phosphodiesterase inhibitors, potassium channel blockers, platelet reducing agents, prostaglandins, proton pump inhibitors, renin inhibitors, selective cyclooxygenase-2 (COX-2) inhibitors, steroids, compounds used for the treatment of glaucoma, and combinations of two or more thereof.

Suitable aldosterone antagonists include, but are not limited to, canrenone, potassium canrenoate, drospirenone, spironolactone, eplerenone (INSPRA®), epoxymexrenone, fadrozole, pregn-4-ene-7,21-dicarboxylic acid, 9,11-epoxy-17-hydroxy-3-oxo, γ-lactone, methyl ester, (7α,11α,17β.)-; pregn-4-ene-7,21-dicarboxylic acid, 9,11-epoxy-17-hydroxy-3-oxo-dimethyl ester, (7α,11α,17β.)-; 3'H-cyclopropa(6,7)pregna-4,6-diene-21-carboxylic acid, 9,11-epoxy-6,7-dihydro-17-hydroxy-3-oxo-, γ-lactone, (6β,7β,11α,17β)-; pregn-4-ene-7,21-dicarboxylic acid, 9,11-epoxy-17-hydroxy-3-oxo-, 7-(1-methylethyl) ester, monopotassium salt, (7α,11α,17β.)-; pregn-4-ene-7,21-dicarboxylic acid, 9,11,-epoxy-17-hydroxy-3-oxo-, 7-methyl ester, monopotassium salt, (7α,11α,17β.)-; 3'H-cyclopropa(6,7) pregna-1,4,6-triene-21-carboxylic acid, 9,11-epoxy-6,7-dihydro-17-hydroxy-3-oxo-, γ-lactone, (6β,7β,11α)-; 3'H-cyclopropa(6,7) pregna-4,6-diene-21-carboxylic acid, 9,11-epoxy-6,7-dihydro-17-hydroxy-3-oxo-, methyl ester, (6β,7β,11α,17β)-; 3'H-cyclopropa (6,7)pregna-4,6-diene-21-carboxylic acid, 9,11-epoxy-6,7-dihydro-17-hydroxy-3-oxo-, monopotassium salt, (6β,7β,11α,17β)-; 3'H-cyclopropa(6,7)pregna-1,4,6-triene-21-carboxylic acid, 9,11-epoxy-6,7-dihydro-17-hydroxy-3-oxo-, γ-lactone, (6β,7β,11α,17β)-; pregn-4-ene-7,21-dicarboxylic acid, 9,11-epoxy-17-hydroxy-3-oxo-, γ-lactone, ethyl ester, (7α,11α,17β)-; pregn-4-ene-7,21-dicarboxylic acid, 9,11-epoxy-17-hydroxy-3-oxo-, γ-lactone, 1-methylethyl ester, (7α,11α,17β)-; RU-28318, and the like. Suitable aldosterone antagonists are described more fully in the literature, such as in Goodman and Gilman, The Pharmacological Basis of Therapeutics (9th Edition), McGraw-Hill, 1995; and the Merck Index on CD-ROM, $13^{th}$ Edition; and on STN Express, file phar and file registry.

In some embodiments the aldosterone antagonists is eplerenone or spironolactone (a potassium sparing diuretic that acts like an aldosterone antagonist). In more particular embodiments eplerenone is administered in an amount of about 25 milligrams to about 300 milligrams as a single dose or as multiple doses per day; the spironolactone is administered in an amount of about 25 milligrams to about 150 milligrams as a single dose or as multiple doses per day.

Suitable α-adrenergic receptor agonists include, but are not limited to, agmatine, p-aminoclonidine, apraclonidine (IOPIDINE®), 2-(arylamino) imidazolidine derivatives, azepexole, azepin derivatives, such as for example, 2-amino-6-alkyl-4,5,7,8-tetrahydro-6H-thiazolo-(5,4,d) azepine, 2-amino-6-ethyl-4,5,7,8-tetrahydro-6H-thiazolo-(5,4,d) azepine, 2-amino-6-ethyl-4,5,7,8-tetrahydro-6H-oxazolo-(5,4,d) azepine, and the like; brimonidine, clonidine, clonidine derivatives, detomidine, dexmedetomidine, dipivefrin, dipivalylepinephrine, epinephrine, guanabenz, guanfacine, imidazolidine derivatives, such as, for example, 5-bromo-6-(2-imidazolidine-2-ylamino)quinoxaline, and the like; p-iodoclonidine, medetomidine, methoxamine (VASOXYL®), mephentermine, metaraminol (ARAMINE®), methyldopa, mitodrine, naphazoline (PRIVINE®, NAPHCON®), norepinephrine, oxymetazoline (AFRIN®, OCUCLEAR®), phenylepinephrine (NEOSYNEPHRINE®), rilmenidine, tetrahydrozoline (TYZINE®, VISINE®), tramazoline, xylazine, xylometazoline (OTRIVIN®), B-HT 920 (6-allyl-2-amino-5,6,7,8-tetrahydro-4H-thiazolo(4,5-d)-azepine, B-HT 933 and UK 14,304, and the like. Suitable α-adrenergic receptor agonists are described more fully in the literature, such as in Goodman and Gilman, The Pharmacological Basis of Therapeutics (9th Edition), McGraw-Hill, (1996); Merck Index on CD-ROM, $13^{th}$ Edition; STN Express, file phar and file registry, the disclosures of each of which are incorporated by reference herein in their entirety.

In some embodiments the α-adrenergic receptor agonists are aminoclonidine, apraclonidine (IOPIDINE®), brimonidine, clonidine and clonidine derivatives.

Suitable α-adrenergic receptor antagonists receptor antagonists include, but are not limited to, phentolamine, tolazoline, idazoxan, deriglidole, RX 821002, BRL 44408, BRL 44409, BAM 1303, labetelol, ifenprodil, rauwolscine, corynathine, raubascine, tetrahydroalstonine, apoyohimbine, akuammigine, β-yohimbine, yohimbol, yohimbine, pseudoyohimbine, epi-3α-yohimbine, 10-hydroxy-yohimbine, 11-hydroxy-yohimbine, tamsulosin, benoxathian, atipamezole, BE 2254, WB 4101, HU-723, tedisamil, mirtazipine, setiptiline, reboxitine, delequamine, naftopil, saterinone, SL 89.0591, ARC 239, urapidil, 5-methylurapidil, monatepi, haloperidol, indoramin, SB 216469, moxisylyte, trazodone, dapiprozole, efaroxan, Recordati 15/2739, SNAP 1069, SNAP 5089, SNAP 5272, RS 17053, SL 89.0591, KMD 3213, spiperone, AH 11110A, chloroethylclonidine, BMY 7378, niguldipine, and the like. Suitable alpha-adrenergic receptor antagonists are described more fully in the literature, such as in Goodman and Gilman, The Pharmacological Basis of Therapeutics (9th Edition), McGraw-Hill, 1995; and the Merck Index on CD-ROM, Thirteenth Edition; and on STN Express, file phar and file registry.

Suitable β-adrenergic agonists include, but are not limited to, albuterol, bambuterol, bitolterol, carbuterol, clenbuterol, dobutamine, fenoterol, formoterol, hexoprenaline, isoprotenerol, mabuterol, metaproterenol, pirbuterol, prenalterol, procaterol, protokylol, ritodrine, rimiterol, reproterol, salmeterol, soterenol, terbutaline, tretoquinol, tulobuterol, and the like. Suitable β-adrenergic agonists are described more fully in the literature, such as in Goodman and Gilman, The Pharmacological Basis of Therapeutics (9th Edition), McGraw-Hill, 1995; and the Merck Index on CD-ROM, $13^{th}$ Edition; and on STN Express, file phar and file registry.

Suitable antidiabetic compounds include, but are not limited to, acarbose, acetohexamide, buformin, carbutamide, chlorpropamide, glibornuride, gliclazide, glimepiride, glipizide, gliquidone, glisoxepid, glyburide, glybuthiazol(e), glybuzole, glyhexamide, glymidine, glypinamide, insulin, metformin, miglitol, nateglinide, phenbutamide, phenformin, pioglitazone, repaglinide, rosiglitazone, tolazamide, tolbutamide, tolcyclamide, troglitazone, voglibose, and the like. Suitable antidiabetic compounds are described more fully in the literature, such as in Goodman and Gilman, The Pharmacological Basis of Therapeutics (9th Edition), McGraw-Hill, 1995; and the Merck Index on CD-ROM, Thirteenth Edition; and on STN Express, file phar and file registry.

Suitable antimicrobial compounds include, but are not limited to, acediasulfone, aceturate, acetyl sulfametossipirazine, acetyl sulfamethoxypyrazine, acranil, albendazole, alexidine, amatadine, ambazone, amdinocillin, amikacin, p-aminosalicylic acid, p-aminosalicylic acid hydrazine, amoxicillin, ampicillin, anisomycin, apalcillin, apicyclin, apramycin, arbekacin, argininsa, aspoxicillin, azidamfenicol, azidocillin, azithromycin, azlocillin, aztreonam, bacampicillin, bacitracin, benzoylpas, benzyl penicillin acid, benzyl sulfamide, bicozamycin, bipenam, brodimoprim, capreomycin, carbenicillin, carbomycin, cafazedone, carindacillin, carumonam, cefcapene pivoxil, cefaclor, cefadroxil, cefafroxil, cefamandole, cefatamet, cefatrizine, cefazedone, cefazolin, cefbuperazone, cefclidin, cefdinir, cefditoren, cefixime, cefmenoxime, cefmetazole, cefminox, cefodizime, cefonicid, cefoperazone, ceforanide, cefotaxime, cefotetan, cefotiam, cefoxitin, cefozopran, cefpimizole, cefpiramide, cefpirome, cefpodoxime proxetil, cefprozil, cefroxadine, cefsulodin, ceftazidime, cefteram, ceftezole, ceftibuten, ceftiofur, ceftizoxime, ceftriaxone, cefuroxime, cefuzonam, cephacetrile sodium, cephadrine, cephalexin, cephaloglycin, cephaloridine, cephalosporin C, cephalothin, cephapirin sodium, cephradine, chibrorifamycin, chloramphenicol, chlorotetracycline, cinoxacin, ciprofloxacin, clarithromycin, clavulanic acid, clinafloxacin, clindamycin, clofazimine, clofoctal, clometocillin, clomocycline, cloxacillin, cloxyquin, colistin, cyclacilline, cycloserine, danoflaxcin, dapsone, deoxycycline, deoxydihydrostreptomycin, dibekacin, dicloxacillin, difloxacin, dihydrostreptomycin, dimetridazole, diminazene, dirirtomycin, duramycin, eflornithine, enrofloxacin, enviomycin, epicillin, erythromycin, etacillin, ethambutol, ethionamide, famcyclovir, fenbecillin, fleroxacin, flomoxef, floxacillin, flumequine, n-formamidoylthienamycin, furonazide, fortimycin, furazolium chloride, gentamycin, glyconiazide, gramicidin, grepafloxacin, guamecycline, halofuginone, hetacillin, homidium, hydroxyl-stilbamidine, ibostamycin, imidocarb, imipenam, ipronidazole, isoniazide, josamycin, inosine, kanamycin, lauroguadine, lenampicillin, lincomycin, lomefloxacin, loracarbef, lymecyclin, mafenide, mebendazole, meclocyclin, meropenem, metampicillin, metacicline, methacycline, methicillin sodium, metronidazole, 4'-(methylsulfamoyl) sulfanilanilide, mezlocillin, meziocillin, micronomycin, midecamycin $A_1$, minocycline, miocamycin, miokamycin, morfazinamide, moxalactam, mupirocin, myxin, nadifloxacin, nalidixic acid, negamycin, neomycin, netlimycin, nifurfoline, nifurpirinol, nifurprazine, nimorazole, nitroxoline, norfloxacin, novobiocin, ofloxacin, oleandomycin, opiniazide, oxacillin, oxophenarsine, oxolinic acid, oxytetracycline, panipenam, paromycin, pazufloxacin, pefloxacin, penicillin G potassium salt, penicillin N, penicillin 0, penicillin V, penethamate hydroiodide, pentamidine, phenamidine, phenethicillin potassium salt, phenyl aminosalicyclate, pipacycline, pipemidic acid, piperacillin, pirlimycin, piromidic acid, pivampicillin, pivcefalexin, polymyxin B, profiromycin, propamidine, propicillin, protionamide, puraltadone, puromycin, pyrazinamide, pyrimethamine, quinacillin, quinacrine, quinapyramine, quintine, ribostamycin, rifabutine, rifamide, rifampin, rifamycin, rifanpin, rifapentine, rifaxymine, ritipenem, rokitamycin, rolitetracycline, rosamycin, rufloxacin, salazosulfadimidine, salinazid, sancycline, sarafloxacin, sedacamycin, secnidazole, sisomycin, sparfloxacin, spectinomycin, spiramycin, spiramycin I, spiramycin II, spiramycin III, stilbamidine, streptomycin, streptonicizid, sulbactam, sulbenicillin, succisulfone, sulfanilamide, sulfabenzamide, sulfacetamide, sulfachloropyridazine, sulfachrysoidine, sulfacytine, sulfadiazine, sulfadicramide, sulfadimethoxine, sulfadoxine, sulfadrazine, sulfaetidol, sulfafenazol, sulfaguanidine, sulfaguanole, sulfalene, sulfamerazine, sulfameter, sulfamethazine, sulfamethizole, sulfamethomidine, sulfamethoxazole, sulfamethoxypyridazine, sulfamethylthiazol, sulfamethylthiazole, sulfametrole, sulfamidochrysoidine, sulfamoxole, sulfanilamide, 4-sulfanilamido salicylic acid, 4-4'-sulfanilylbenzylamine, p-sulfanilylbenzylamine, 2-p-sulfinylanilinoethanol, sulfanilylurea, sulfoniazide, sulfaperine, sulfaphenazole, sulfaproxyline, sulfapyrazine, sulfapyridine, sulfathiazole, sulfaethidole, sulfathiourea, sulfisomidine, sulfasomizole, sulfasymazine, sulfisoxazole, 4,4'-sulfinyldianiline, $N^4$-sulfanilylsulfanilamide, N-sulfanilyl-3,4-xylamide, sultamicillin, talampicillin, tambutol, taurolidine, teiclplanin, temocillin, tetracycline, tetroxoprim, thiabendazole, thiazolsulfone, tibezonium iodide, ticarcillin, tigemonam, tinidazole, tobramycin, tosufloxacin, trimethoprim, troleandromycin, trospectomycin, trovafloxacin, tubercidine, miokamycin, oleandomycin, troleandromycin, vancomycin, verazide, viomycin, virginiamycin, zalcitabine, PA-1806 and PA-2794, and the like. Suitable antimicrobial compounds are described more fully in the literature, such as in Goodman and Gilman, The Pharmacological Basis of Therapeutics (9th Edition), McGraw-Hill, (1996); Merck Index on CD-ROM, $13^{th}$ Edition; STN Express, file phar and file registry, the disclosures of each of which are incorporated by reference herein in their entirety.

In some embodiments the antimicrobial compounds include, but are not limited to, amikacin, azithromycin, aztreonam, bacitracin, carbenicillin, cefazolin, cefoxitin, cephaloridine, chibrorifamycin, chloramphenicol, colistin, duramycin, n-formamidoylthienamycin, gentamycin, gramicidin, kanamycin, neomycin, penicillin G, polymyxin B, sisomicin, tetracyclines, tigecycline, tobramycin, vancomycin, PA-1806 and PA-2794.

In other embodiments the antimicrobial compound is an antiviral compound, including but not limited to, acyclovir, amatadine, cidofovir, cytarabine, didanosine, dideoxyadenosine, edoxudine, famciclovir, floxuridine, gancyclovir, idoxuridine, indanavir, kethoxal, lamivudine, MADU, penciclovir, podophyllotoxin, ribavirine, rimantadine, saquinavir, sorivudine, stavudine, trifluridine, valacyclovir, vidarabine, xenazoic acid, zalcitabine, zidovudine, and the like.

Suitable anti-hyperlipidemic compounds include, but are not limited to, statins or HMG-CoA reductase inhibitors, such as, for example, atorvastatin (LIPITOR®), bervastatin, cerivastatin (BAYCOL®), dalvastatin, fluindostatin (Sandoz XU-62-320), fluvastatin, glenvastatin, lovastatin (MEVACOR®), mevastatin, pravastatin (PRAVACHOL®), rosuvastatin (CRESTRO®), simvastatin (ZOCOR®), velostatin (also known as synvinolin), VYTORIN™ (ezetimibe/simvastatin), GR-95030, SQ 33,600, BMY 22089, BMY 22,566, CI-980, and the like; gemfibrozil, cholystyramine, colestipol, niacin, nicotinic acid, bile acid sequestrants, such as, for example, cholestyramine, colesevelam, colestipol, poly(methyl-(3-trimethylaminopropyl) imino-trimethylene dihalide) and the like; probucol; fibric acid agents or fibrates, such as, for example, bezafibrate (Bezalip™), beclobrate, binifibrate, ciprofibrate, clinofibrate, clofibrate, etofibrate, fenofibrate (Lipidil™, Lipidil Micro™), gemfibrozil (Lopid™.), nicofibrate, pirifibrate, ronifibrate, simflbrate, theofibrate and the like; cholesterol ester transfer protein (CETP) inhibitors, such as for example, CGS 25159, CP-529414 (torcetrapid), JTT-705, substituted N-[3-(1,1,2,2-tetrafluoroethoxy)benzyl]-N-(3-phenoxyphenyl)-trifluoro-3-amino-2-propanols, N,N-disubstituted trifluoro-3-amino-2-propanols, PD 140195 (4-phenyl-5-tridecyl-4H-1,2,4-triazole-3-thiol), SC-794, SC-795, SCH 58149, and the like.

In some embodiments the anti-hyperlipidemic compounds are atorvastatin, fluvastatin, lovastatin, pravastatin, rosuvastatin or simvastatin. In more particular embodiments the atorvastatin is administered in an amount of about 10 milligrams to about 80 milligrams as a single dose or as multiple doses per day; the fluvastatin is administered in an amount of about 20 milligrams to about 80 milligrams as a single dose or as multiple doses per day; the lovastatin is administered in an amount of about 10 milligrams to about 80 milligrams as a single dose or as multiple doses per day; the pravastatin is administered in an amount of about 10 milligrams to about 80 milligrams as a single dose or as multiple doses per day; the rosuvastatin is administered in an amount of about 5 milligrams to about 40 milligrams as a single dose or as multiple doses per day; the simvastatin is administered in an amount of about 5 milligrams to about 80 milligrams as a single dose or as multiple doses per day.

Suitable angiotensin II antagonists include, but are not limited to, angiotensin, abitesartan, candesartan, candesartan cilexetil, elisartan, embusartan, enoltasosartan, eprosartan, fonsartan, forasartan, glycyllosartan, irbesartan, losartan, olmesartan, milfasartan, medoxomil, ripisartan, pomisartan, pratosartan, saprisartan, saralasin, sarmesin, tasosartan, telmisartan, valsartan, zolasartan, 3-(2'(tetrazole-5-yl)-1,1'-biphen-4-yl)methyl-5,7-dimethyl-2-ethyl-3H-imidazo[4,5-b]pyridine, antibodies to angiotensin II, A-81282, A-81988, BAY 106734, BIBR-363, BIBS-39, BIBS-222, BMS-180560, BMS-184698, BMS-346567, CGP-38560A, CGP-42112A, CGP-48369, CGP-49870, CGP-63170, CI-996, CP-148130, CL-329167, CV-11194, CV-11974, DA-2079, DE-3489, DMP-811, DuP-167, DuP-532, DuP-753, E-1477, E-4177, E-4188, EMD-66397, EMD-666R4, EMD-73495, EMD-66684, EXP-063, EXP-929, EXP-3134, EXP-3174, EXP-6155, EXP-6803, EXP-7711, EXP-9270, EXP-9954, FK-739, FRI 153332, GA-0050, GA-0056, HN-65021, HOE-720, HR-720, ICI-D6888, ICI-D7155, ICI-D8731, KRI-1177, KT3-671, KT-3579, KW-3433, L-158809, L-158978, L-159282 (MK-996), L-159689, L-159874, L-161177, L-162154, L-162234, L-162441, L-163007, L-163017, LF-70156, LRB-057, LRB-081, LRB-087, LY-235656, LY-266099, LY-285434, LY-301875, LY-302289, LY-315995, ME-3221, MK-954, PD-123177, PD-123319, PD-126055, PD-150304, RG-13647, RWJ-38970, RWJ-46458, S-8307, S-8308, SC-51757, SC-54629, SC-52458, SC-52459, SK 1080, SL-910102, SR-47436, TAK-536, UP-2696, U-96849, U-97018, UK-77778, UP-275-22, WAY-126227, WK-1260, WK-1360, WK-1492, WY 126227, YH-1498, YM-358, YM-31472, X-6803, XH-148, XR-510, ZD-6888, ZD-7155, ZD-8731, ZD 8131, the compounds of ACS registry numbers 133240-46-7, 135070-05-2, 139958-16-0, 145160-84-5, 147403-03-0, 153806-29-2, 439904-54-8P, 439904-55-9P, 439904-56-0P, 439904-57-1P, 439904-58-2P, 155918-60-8P, 155918-61-9P, 272438-16-1P, 272446-75-0P, 223926-77-0P, 169281-89-4, 165113-17-7P, 165113-18-8P, 165113-19-9P, 165113-20-2P, 165113-β-3P, 165113-14-4P, 165113-15-5P, 165113-16-6P, 165113-21-3P, 165113-22-4P, 165113-23-5P, 165113-24-6P, 165113-25-7P, 165113-26-8P, 165113-27-9P, 165113-28-0P, 165113-29-1P, 165113-30-4P, 165113-31-5P, 165113-32-6P, 165113-33-7P, 165113-34-8P, 165113-35-9P, 165113-36-0P, 165113-37-1P, 165113-38-2P, 165113-39-3P, 165113-40-6P, 165113-41-7P, 165113-42-8P, 165113-43-9P, 165113-44-0P, 165113-45-1P, 165113-46-2P, 165113-47-3P, 165113-48-4P, 165113-49-5P, 165113-50-8P, 165113-51-9P, 165113-52-0P, 165113-53-1P, 165113-54-2P, 165113-55-3P, 165113-56-4P, 165113-57-5P, 165113-58-6P, 165113-59-7P, 165113-60-0P, 165113-61-1P, 165113-62-2P, 165113-63-3P, 165113-64-4P, 165113-65-5P, 165113-66-6P, 165113-67-7P, 165113-68-8P, 165113-69-9P, 165113-70-2P, 165113-71-3P, 165113-72-4P, 165113-73-5P, 165113-74-6P, 114798-27-5, 114798-28-6, 114798-29-7, 124749-82-2, 114798-28-6, 124749-84-4, 124750-88-5, 124750-91-0, 124750-93-2, 161946-65-2P, 161947-47-3P, 161947-48-4P, 161947-51-9P, 161947-52-0P, 161947-55-3P, 161947-56-4P, 161947-60-0P, 161947-61-1P, 161947-68-8P, 161947-69-9P, 161947-70-2P, 161947-71-3P, 161947-72-4P, 161947-74-6P, 161947-75-7P, 161947-81-5P, 161947-82-6P, 161947-83-7P, 161947-84-8P, 161947-85-9P, 161947-86-0P, 161947-87-1P, 161947-88-2P, 161947-89-3P, 161947-90-6P, 161947-91-7P, 161947-92-8P, 161947-93-9P, 161947-94-0P, 161947-95-1P, 161947-96-2P, 161947-97-3P, 161947-98-4P, 161947-99-5P, 161948-00-1P, 161948-01-2P, 161948-02-3P, 168686-32-6P, 167301-42-0P, 166813-82-7P, 166961-56-4P, 166961-58-6P, 158872-96-9P, 158872-97-0P, 158807-14-8P, 158807-15-9P, 158807-16-0P, 158807-17-1P, 158807-18-2P, 158807-19-3P, 158807-20-6P, 155884-08-5P, 154749-99-2, 167371-59-7P, 244126-99-6P, 177848-35-0P, 141309-82-2P, and the like. Suitable angiotensin II antagonists are described more fully in the literature, such as in Goodman and Gilman, The Pharmacological Basis of Therapeutics (9th Edition), McGraw-Hill, 1995; and the Merck Index on CD-ROM, 13$^{th}$ Edition; and on STN Express, file phar and file registry.

In some embodiments the angiotensin II antagonists are candesartan, eprosartan, irbesartan, losartan, olmesartan, telmisartan or valsartan. In more particular embodiments the candesartan is administered as candesartan cilexetil in an amount of about 15 milligrams to about 100 milligrams as a single dose or as multiple doses per day; the eprosartan, is administered as eprosartan mesylate in an amount of about 400 milligrams to about 1600 milligrams as a single dose or as multiple doses per day; the irbesartan is administered in an amount of about 75 milligrams to about 1200 milligrams as a single dose or as multiple doses per day; the losartan is administered as losartan potassium in an amount of about 25 milligrams to about 100 milligrams as a single dose or as multiple doses per day; the olmesartan is administered as olmesartan medoxomil in an amount of about 5 milligrams to about 40 milligrams as a single dose or as multiple doses per day; the telmisartan is administered in an amount of about 20 milligrams to about 80 milligrams as a single dose or as multiple doses per day; the valsartan is administered in an amount of about 80 milligrams to about 320 milligrams as a single dose or as multiple doses per day.

Suitable angiotensin-converting enzyme inhibitors (ACE inhibitors) include, but are not limited to, alacepril, benazepril (LOTENSIN®, CIBACEN®), benazeprilat, captopril, ceronapril, cilazapril, delapril, duinapril, enalapril, enalaprilat, fasidotril, fosinopril, fosinoprilat, gemopatrilat, glycopril, idrapril, imidapril, lisinopril, moexipril, moveltipril, naphthopidil, omapatrilat, pentopril, perindopril, perindoprilat, quinapril, quinaprilat, ramipril, ramiprilat, rentipril, saralasin acetate, spirapril, temocapril, trandolapril, trandolaprilat, urapidil, zofenopril, acylmercapto and mercaptoalkanoyl pralines, carboxyalkyl dipeptides, carboxyalkyl dipeptide, phosphinylalkanoyl pralines, registry no. 796406, AVE 7688, BP1.137, CHF 1514, E 4030, ER 3295, FPL-66564, MDL 100240, RL 6134, RL 6207, RL 6893, SA 760, S-5590, Z 13752A, and the like. Suitable angiotensin-converting enzyme inhibitors are described more fully in the literature, such as in Goodman and Gilman, The Pharmacological Basis of Therapeutics (9th Edition), McGraw-Hill, 1995; and the Merck Index on CD-ROM, Twelfth Edition, Version 12:1, 1996; and on STN Express, file phar and file registry.

In some embodiments the angiotensin-converting enzyme inhibitors are benazepril, captopril, enalapril, fosinopril, lisinopril, moexipril, quinapril, ramipril, trandolapril or trandolaprilat. In more particular embodiments the benazepril is administered as benazepril hydrochloride in an amount of about 5 milligrams to about 80 milligrams as a single dose or as multiple doses per day; the captopril is administered in an amount of about 12.5 milligrams to about 450 milligrams as a single dose or as multiple doses per day; the enalapril is administered as enalapril maleate in an amount of about 2.5 milligrams to about 40 milligrams as a single dose or as multiple doses per day; the fosinopril is administered as fosinopril sodium in an amount of about 5 milligrams to about 60 milligrams as a single dose or as multiple doses per day; the lisinopril is administered in an amount of about 2.5 milligrams to about 75 milligrams as a single dose or as multiple doses per day; the moexipril is administered as moexipril hydrochloride in an amount of about 7.5 milligrams to about 45 milligrams as a single dose or as multiple doses per day; the quinapril is administered as quinapril hydrochloride in an amount of about 5 milligrams to about 40 milligrams as single or multiple doses per day; the ramipril hydrochloride in an amount of about 1.25 milligrams to about 40 milligrams as single or multiple doses per day; the trandolapril is administered as in an amount of about 0.5 milligrams to about 4 milligrams as single or multiple doses per day; the trandolaprilat is administered as in an amount of about 0.5 milligrams to about 4 milligrams as single or multiple doses per day.

Suitable antioxidants include, but are not limited to, small-molecule antioxidants and antioxidant enzymes. Suitable small-molecule antioxidants include, but are not limited to, hydralazine compounds, glutathione, vitamin C, vitamin E, cysteine, N-acetyl-cysteine, β-carotene, ubiquinone, ubiquinol-10, tocopherols, coenzyme Q, superoxide dismutase mimetics, such as, for example, 2,2,6,6-tetramethyl-1-piperidinyloxy (TEMPO), DOXYL, PROXYL nitroxide compounds; 4-hydroxy-2,2,6,6-tetramethyl-1-piperidinyloxy (Tempol), M-40401, M-40403, M-40407, M-40419, M-40484, M-40587, M-40588, and the like. Suitable antioxidant enzymes include, but are not limited to, superoxide dismutase, catalase, glutathione peroxidase, NADPH oxidase inhibitors, such as, for example, apocynin, aminoguanidine, ONO 1714, S17834 (benzo(b)pyran-4-one derivative), and the like; xanthine oxidase inhibitors, such as, for example, allopurinol, oxypurinol, amflutizole, diethyldithiocarbamate, 2-styrylchromones, chrysin, luteolin, kaempferol, quercetin, myricetin, isorhamnetin, benzophenones such as 2,2',4,4'-tetrahydroxybenzophenone, 3,4,5,2',3',4'-hexahydroxybenzophenone and 4,4'-dihydroxybenzophenone; benzothiazinone analogues such as 2-amino-4H-1,3-benzothiazine-4-one, 2-guanidino-4H-1,3-benzothiazin-4-one and rhodanine; N-hydroxyguanidine derivative such as, PR5 (1-(3,4-dimethoxy-2-chlorobenzylideneamino)-3-hydroxyguanidine); 6-formylpterin, and the like. The antioxidant enzymes can be delivered by gene therapy as a viral vertor and/or a non-viral vector. Suitable antioxidants are described more fully in the literature, such as in Goodman and Gilman, The Pharmacological Basis of Therapeutics (9th Edition), McGraw-Hill, 1995; and the Merck Index on CD-ROM, Thirteenth Edition; and on STN Express, file phar and file registry.

In some embodiments the antioxidants are apocynin, hydralazine compounds and superoxide dimutase mimetics.

Suitable antithrombotic and vasodilator compounds include, but are not limited to, abciximab, acetorphan, acetylsalicylic acid, argatroban, bamethan, benfurodil, benziodarone, betahistine, bisaramil, brovincamine, bufeniode, citicoline, clobenfurol, clopidogrel, cyclandelate, dalteparin, dipyridamol, droprenilamine, enoxaparin, fendiline, ifenprodil, iloprost, indobufen, isobogrel, isoxsuprine, heparin, lamifiban, midrodine, nadroparin, nicotinoyl alcohol, nylidrin, ozagrel, perhexyline, phenylpropanolamine, prenylamine, papaveroline, reviparin sodium salt, ridogrel, suloctidil, tinofedrine, tinzaparin, trifusal, vintoperol, xanthinal niacinate, and the like. Suitable antithrombotic and vasodilator compounds are described more fully in the literature, such as in Goodman and Gilman, The Pharmacological Basis of Therapeutics (9th Edition), McGraw-Hill, 1995; and the Merck Index on CD-ROM, Thirteenth Edition; and on STN Express, file phar and file registry.

Suitable β-adrenergic antagonists include, but are not limited to, acebutolol, alprenolol, amosulalol, arotinolol, atenolol, befunolol, betaxolol, bevantolol, bisoprolol, bopindolol, bucindolol, bucumolol, bufetolol, bufuralol, bunitrolol, bupranolol, butofilolol, carazolol, capsinolol, carteolol, carvedilol (COREG®), celiprolol, cetamolol, cindolol, cloranolol, dilevalol, diprafenone, epanolol, ersentilide, esmolol, esprolol, hydroxalol, indenolol, labetalol, landiolol, laniolol, levobunolol, mepindolol, methylpranol, metindol, metipranolol, metrizoranolol, metoprolol, moprolol, nadolol, nadoxolol, nebivolol, nifenalol, nipradilol, oxprenolol, penbutolol, pindolol, practolol, pronethalol, propranolol, sotalol, sotalolnadolol, sulfinalol, taliprolol, talinolol, tertatolol, tilisolol, timolol, toliprolol, tomalolol, trimepranol, xamoterol, xibenolol, 2-(3-(1,1-dimethylethyl)-amino-2-hydroxypropoxy)-3-pyridenecarbonitrilHCl, 1-butylamino-3-(2,5-dichlorophenoxy)-2-propanol, 1-isopropylamino-3-(4-(2-cyclopropylmethoxyethyl)phenoxy)-2-propanol, 3-isopropylamino-1-(7-methylindan-4-yloxy)-2-butanol, 2-(3-t-butylamino-2-hydroxy-propylthio)-4-(5-carbamoyl-2-thienyl)thiazol, 7-(2-hydroxy-3-t-butylaminpropoxy)phthalide, Acc 9369, AMO-140, BIB-165, CP-331684, Fr-172516, ISV-208, L-653328, LM-2616, SB-226552, SR-58894A, SR-59230A, TZC-5665, UK-1745, YM-430, and the like. Suitable β-adrenergic antagonists are described more fully in the literature, such as in Goodman and Gilman, The Pharmacological Basis of Therapeutics (9th Edition), McGraw-Hill, 1995; and the Merck Index on CD-ROM, 13th Edition; and on STN Express, file phar and file registry.

In some embodiments the β-adrenergic antagonists are atenolol, bisoprolol, carvedilol, metoprolol, nebivolol, propranolol or timolol. In more particular embodiments the atenolol is administered in an amount of about 50 milligrams to about 200 milligrams as a single dose or as multiple doses per day; the bisoprolol is administered as bisoprolol fumarate in an amount of about 2.5 milligrams to about 30 milligrams as a single dose or as multiple doses per day; the carvedilol is administered in an amount of about 3.125 milligrams to about 200 milligrams as a single dose or as multiple doses per day; the metoprolol is administered as metoprolol tartarate or metoprolol succinate in an amount of about 25 milligrams to about 300 milligrams as a single dose or as multiple doses per day; the nebivolol is administered as nebivolol hydrochloride in an amount of about 2.5 milligrams to about 20 milligrams as a single dose or as multiple doses per day; the propranolol is administered as propranolol hydrochloride in an amount of about 40 milligrams to about 240 milligrams as a single dose or as multiple doses per day; the timolol is administered as timolol maleate in an amount of about 10 milligrams to about 30 milligrams as a single dose or as multiple doses per day.

Suitable calcium channel blockers include, but are not limited to, amlodipine (NORVASC®), anipamil, aranidipine, amrinone, azelnidipine, barnidipine, bencyclane, benidipine, bepridil, cilnidipine, cinnarizine, clentiazem, diltiazem, dotarizine, efonidipine, elgodipine, fantofarone, felodipine, fendiline, flunarizine, fluspirilene, furnidipine, gallopamil, ipenoxazone, isradipine, lacidipine, lemildipine, lercanidipine, lomerizine, manidipine, mibefradil, monatepil, nicardipine, nifedipine, niguldipine, niludipine, nilvadipine, nimodipine, nisoldipine, nitrendipine, nivaldipine, oxodipine, perhexylene, phenyloin, phenylprenylamine, pranidipine, ranolazine, ryosidine, semotiadil, tamolarizine, temiverine hydrochloride, terodiline, tiapamil, vatanidipine hydrochloride, verapamil, ziconotide, AE-0047, CAI, JTV-519, CHF-1521, L-651582, NS-7, NW-1015, RO-2933, SB-237376, SL-34.0829-08, S-312d, SD-3212, TA-993, YM-430, and the like. Suitable calcium channel blockers are described more fully in the literature, such as in Goodman and Gilman, The Pharmacological Basis of Therapeutics (9th Edition), McGraw-Hill, 1995; and the Merck Index on CD-ROM, Thirteenth Edition; and on STN Express, file phar and file registry.

In some embodiments the calcium channel blockers are amlodipine, diltiazem, isradipine, nicardipine, nifedipine, nimodipine, nisoldipine, nitrendipine, verapamil.

Suitable carbonic anhydrase inhibitors include, but are not limited to, acetazolamide, brinzolamide, dorzolamide, ethoxzolamide, 6-hydroxy-2-benzothiazolesulfonamide, methazolamide, thiophene sulfonamide, an aromatic sulfonamide, an ester of 6-hydroxy-2-benzothiazolesulfonamide, an ester of 5-hydroxy-2-benzothiazolesulfonamide, and the like. Suitable carbonic anhydrase inhibitors are described more fully in the literature, such as in Goodman and Gilman, The Pharmacological Basis of Therapeutics (9th Edition), McGraw-Hill, 1995; and the Merck Index on CD-ROM, 13th Edition; and on STN Express, file phar and file registry.

In some embodiments the carbonic anhydrase inhibitors are brinzolamide and dorzolamide.

Suitable diuretics include, but are not limited to, thiazides (such as for example, althiazide, bendroflumethiazide, benzclortriazide, benzhydrochlorothiazide, benzthiazide, buthiazide, chlorothiazide, cyclopenethiazide, cyclothiazide, epithiazide, ethiazide, hydrobenzthiazide, hydrochlorothiazide, hydroflumethiazide, methylclothiazide, methylcyclothiazide, penflutazide, polythiazide, teclothiazide, trichlormethiazide, triflumethazide, and the like); alilusem, ambuside, amiloride, aminometradine, azosemide, bemetizide, bumetanide, butazolamide, butizide, canrenone, carperitide, chloraminophenamide, chlorazanil, chlormerodrin, chlorthalidone, cicletanide, clofenamide, clopamide, clorexolone, conivaptan, daglutril, dichlorophenamide, disulfamide, ethacrynic acid, ethoxzolamide, etozolon, fenoldopam, fenquizone, furosemide, indapamide, mebutizide, mefruside, meralluride, mercaptomerin sodium, mercumallylic acid, mersalyl, methazolamide, meticane, metolazone, mozavaptan, muzolimine, N-(5-1,3,4-thiadiazol-2-yl)acetamide, nesiritide, pamabrom, paraflutizide, piretanide, protheobromine, quinethazone, scoparius, spironolactone, theobromine, ticrynafen, torsemide, torvaptan, triamterene, tripamide, ularitide, xipamide or potassium, AT 189000, AY 31906, BG 9928, BG 9791, C 2921, DTI 0017, JDL 961, KW 3902, MCC 134, SLV 306, SR 121463, WAY 140288, ZP 120, and the like. Suitable diuretics are described more fully in the literature, such as in Goodman and Gilman, The Pharmacological Basis of Therapeutics (9th Edition), McGraw-Hill, 1995; and the Merck Index on CD-ROM, 13th Edition; and on STN Express, file phar and file registry.

Depending on the diuretic employed, potassium may also be administered to the patient in order to optimize the fluid balance while avoiding hypokalemic alkalosis. The administration of potassium can be in the form of potassium chloride or by the daily ingestion of foods with high potassium content such as, for example, bananas or orange juice. The method of administration of these compounds is described in further detail in U.S. Pat. No. 4,868,179, the disclosure of which is incorporated by reference herein in its entirety.

In some embodiments the diuretics are amiloride, furosemide, chlorthalidone, hydrochlorothiazide or triamterene. In more particular embodiments the amiloride is administered as amiloride hydrochloride in an amount of about 5 milligrams to about 15 milligrams as a single dose or as multiple doses per day; the furosemide is administered in an amount of about 10 milligrams to about 600 milligrams as a single dose or as multiple doses per day; the chlorthalidone is administered in an amount of about 15 milligrams to about 150 milligrams as a single dose or as multiple doses per day; the hydrochlorothiazide is administered in an amount of about 12.5 milligrams to about 300 milligrams as a single dose or as multiple doses per day; the triamterene is administered in an amount of about 35 milligrams to about 225 milligrams as a single dose or as multiple doses per day.

Suitable endothelin antagonists include, but are not limited to, atrasentan, bosentan, darusentan, endothelin, enrasentan, sitaxsentan, sulfonamide endothelin antagonists, tezosentan, BMS193884, BQ-123, SQ 28608, and the like. Suitable endothelin antagonists are described more fully in the literature, such as in Goodman and Gilman, The Pharmacological Basis of Therapeutics (9th Edition), McGraw-Hill, 1995; and the Merck Index on CD-ROM, Thirteenth Edition; and on STN Express, file phar and file registry.

Suitable hydralazine compounds include, but are not limited to, compounds having the formula:

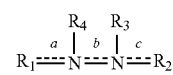

wherein a, b and c are independently a single or double bond; $R_1$ and $R_2$ are each independently a hydrogen, an alkyl, an ester or a heterocyclic ring, wherein alkyl, ester and heterocyclic rind are as defined herein; $R_3$ and $R_4$ are each independently a lone pair of electrons or a hydrogen, with the proviso that at least one of $R_1$, $R_2$, $R_3$ and $R_4$ is not a hydrogen. Exemplary hydralazine compounds include budralazine, cadralazine, dihydralazine, endralazine, hydralazine, pildralazine, todralazine, and the like. Suitable hydralazine compounds are described more fully in the literature, such as in Goodman and Gilman, The Pharmacological Basis of Therapeutics (9th Edition), McGraw-Hill, 1995; and the Merck Index on CD-ROM, Thirteenth Edition; and on STN Express, file phar and file registry.

In some embodiments the hydralazine compound is hydralazine or a pharmaceutically acceptable salt thereof such as hydralazine hydrochloride. In more particular embodiments the hydralazine is administered as hydralazine hydrochloride in an amount of about 10 milligrams to about 300 milligrams as a single dose or as multiple doses per day.

Suitable $H_2$ receptor antagonists include, but are not limited to, burimamide, cimetidine, ebrotidin, famotidine, nizatidine, roxatidine, rantidine, tiotidine, and the like. Suitable $H_2$ receptor antagonists are described more fully in the literature, such as in Goodman and Gilman, The Pharmacological Basis of Therapeutics (9th Edition), McGraw-Hill, 1995, Pgs. 901-915; the Merck Index on CD-ROM, 13$^{th}$ Edition; and in WO 00/28988 assigned to NitroMed. Inc., the disclosures of which are incorporated herein by reference in their entirety.

Suitable neutral endopeptidase inhibitors include, but are not limited to, atrial natriuretic peptides, diazapins, azepinones, ecadotril, fasidotril, fasidotrilat, omapatrilat, sampatrilat, BMS 189,921, Z 13752 A, and the like. Neutral endopeptidase inhibitors are described more fully in the literature, such as in Goodman and Gilman, The Pharmacological Basis of Therapeutics (9th Edition), McGraw-Hill, 1995; and the Merck Index on CD-ROM, Thirteenth Edition; and on STN Express, file phar and file registry.

Suitable NSAIDs include, but are not limited to, acetaminophen, acemetacin, aceclofenac, alminoprofen, amfenac, bendazac, benoxaprofen, bromfenac, bucloxic acid, butibufen, carprofen, cinmetacin, clopirac, diclofenac, etodolac, felbinac, fenclozic acid, fenbufen, fenoprofen, fentiazac, flunoxaprofen, flurbiprofen, ibufenac, ibuprofen, indomethacin, isofezolac, isoxepac, indoprofen, ketoprofen, lonazolac, loxoprofen, metiazinic acid, mofezolac, miroprofen, naproxen, oxaprozin, pirozolac, pirprofen, pranoprofen, protizinic acid, salicylamide, sulindac, suprofen, suxibuzone, tiaprofenic acid, tolmetin, xenbucin, ximoprofen, zaltoprofen, zomepirac, aspirin, acemetcin, bumadizon, carprofenac, clidanac, diflunisal, enfenamic acid, fendosal, flufenamic acid, flunixin, gentisic acid, ketorolac, meclofenamic acid, mefenamic acid, mesalamine, prodrugs thereof, and the like. Suitable NSAIDs are described more fully in the literature, such as in Goodman and Gilman, The Pharmacological Basis of Therapeutics (9th Edition), McGraw-Hill, 1995, Pgs. 617-657; the Merck Index on CD-ROM, 13$^{th}$ Edition; and in U.S. Pat. Nos. 6,057,347 and 6,297,260 assigned to NitroMed Inc., the disclosures of which are incorporated herein by reference in their entirety.

In some embodiments the NSAIDs are acetaminophen, diclofenac, flurbiprofen, ibuprofen, indomethacin, ketoprofen, naproxen or aspirin. In more particular embodiments the acetaminophen is administered in an amount of about 325 milligrams to about 4 grams as a single dose or as multiple doses per day; the diclofenac is administered in an amount of about 50 milligrams to about 250 milligrams as a single dose or as multiple doses per day; the flurbiprofen is administered in an amount of about 100 milligrams to about 300 milligrams as a single dose or as multiple doses per day; the ibuprofen is administered in an amount of about 400 milligrams to about 3.2 grams as a single dose or as multiple doses per day; the indomethacin is administered in an amount of about 25 milligrams to about 200 milligrams as a single dose or as multiple doses per day; the ketoprofen is administered in an amount of about 50 milligrams to about 300 milligrams as a single dose or as multiple doses per day; the naproxen is administered in an amount of about 250 milligrams to about 1.5 grams as a single dose or as multiple doses per day; the aspirin is administered in an amount of about 10 milligrams to about 2 grams as a single dose or as multiple doses per day.

Suitable phosphodiesterase inhibitors include, but are not limited to, filaminast, piclamilast, rolipram, Org 20241, MCI-154, roflumilast, toborinone, posicar, lixazinone, zaprinast, sildenafil, pyrazolopyrimidinones, motapizone, pimobendan, zardaverine, siguazodan, CI-930, EMD 53998, imazodan, saterinone, loprinone hydrochloride, 3-pyridinecarbonitrile derivatives, acefylline, albifylline, bamifylline, denbufyllene, diphylline, doxofylline, etofylline, torbafylline, theophylline, nanterinone, pentoxofylline, proxyphylline, cilostazol, cilostamide, MS 857, piroximone, milrinone, amrinone, tolafentrine, dipyridamole, papaveroline, E4021, thienopyrimidine derivatives, triflusal, ICOS-351, tetrahydropiperazino (1,2-b)beta-carboline-1,4-dione derivatives, carboline derivatives, 2-pyrazolin-5-one derivatives, fused pyridazine derivatives, quinazoline derivatives, anthranilic acid derivatives, imidazoquinazoline derivatives, tadalafil, vardenafil, and in Goodman and Gilman, The Pharmacological Basis of Therapeutics (9th Ed.), McGraw-Hill, Inc. (1995), The Physician's Desk Reference (49th Ed.), Medical Economics (1995), Drug Facts and Comparisons (1993 Ed), Facts and Comparisons (1993), and the Merck Index on CD-ROM, 13$^{th}$ Edition; and the like. Phosphodiesterase inhibitors and their nitrosated and/or nitrosylated derivatives are also disclosed in U.S. Pat. Nos. 5,932,538, 5,994,294, 5,874,437, 5,958,926 reissued as U.S. Pat. No. RE 0,377,234, 6,172,060, 6,197,778, 6,177,428, 6,172,068, 6,221,881, 6,232,321, 6,197,782, 6,133,272, 6,211,179, 6,316,457 and 6,331,542, the disclosures of each of which are incorporated herein by reference in their entirety.

Suitable potassium channel blockers include, but are not limited to, nicorandil, pinacidil, cromakalim (BRL 34915), aprikalim, bimakalim, emakalim, lemakalim, minoxidil, diazoxide, 9-chloro-7-(2-chlorophenyl)-5H-pyrimido(5,4,-d) (2)-benzazepine, Ribi, CPG-11952, CGS-9896, ZD 6169, diazixide, Bay X 9227, P1075, Bay X 9228, SDZ PCO 400, WAY-120,491, WAY-120,129, Ro 31-6930, SR 44869, BRL 38226, S 0121, SR 46142A, CGP 42500, SR 44994, artilide fumarate, lorazepam, temazepam, rilmazafone, nimetazepam, midazolam, lormetazepam, loprazolam, ibutilide fumarate, haloxazolam, flunitrazepam, estazolam, doxefazepam, clonazepam, cinolazepam, brotizolam, and the like. Suitable potassium channel blockers are described more fully in the literature, such as in Goodman and Gilman, The Pharmacological Basis of Therapeutics (9th Edition), McGraw-Hill, 1995; and the Merck Index on CD-ROM, Thirteenth Edition; and on STN Express, file phar and file registry.

Suitable platelet reducing agents include, but are not limited to, fibrinolytic agents such as for example, ancrod, anistreplase, bisobrin lactate, brinolase, Hageman factor (i.e. factor XII) fragments, plasminogen activators such as, for example, streptokinase, tissue plasminogen activators (TPA), urokinase, pro-Urokinase, recombinant TPA, plasmin, plasminogen, and the like; anti-coagulant agents including but are not limited to, inhibitors of factor Xa, factor TFPI, factor VIIa, factor IXc, factor Va, factor VIIIa, inhibitors of other coagulation factors, and the like; vitamin K antagonists, such as, for example, coumarin, coumarin derivatives (e.g., warfarin sodium); glycosoaminoglycans such as, for example, heparins both in unfractionated form and in low molecular weight form; ardeparin sodium, bivalirudin, bromindione, coumarin, dalteparin sodium, danaparoid sodium; dazoxiben hydrochloride, desirudin, dicumarol, efegatran sulfate, enoxaparin sodium, ifetroban, ifetroban sodium, lyapolate sodium, nafamostat mesylate, phenprocoumon, sulfatide, tinzaparin sodium, retaplase; trifenagrel, warfarin, dextrans and the like; abciximab, acadesine, anipamil, argatroban, aspirin, clopidogrel, diadenosine 5',5'''-P1,P4-tetraphosphate (Ap4A) analogs, difibrotide, dilazep dihydrochloride, dipyridamole, dopamine, 3-methoxytyramine, glucagon, glycoprotein IIb/IIIa antagonists, such as, for example, Ro-43-8857, L-700,462, iloprost, isocarbacyclin methyl ester, itazigrel, ketanserin, BM-13.177, lamifiban, lifarizine, molsidomine, nifedipine, oxagrelate, prostaglandins, platelet activating factor antagonists such as, for example, lexipafant, prostacyclins, pyrazines, pyridinol carbamate, ReoPro (i.e., abciximab), sulfinpyrazone, synthetic compounds BN-50727, BN-52021, CV-4151, E-5510, FK-409, GU-7, KB-2796, KBT-3022, KC-404, KF-4939, OP-41483, TRK-100, TA-3090, TFC-612, ZK-36374, 2,4,5,7-tetrathiaoctane, 2,4,5,7-tetrathiaoctane 2,2-dioxide, 2,4,5-trithiahexane, theophyllin pentoxifyllin, thromboxane and thromboxane synthetase inhibitors such as, for example, picotamide, sulotroban, ticlopidine, tirofiban, trapidil, ticlopidine, trifenagrel, trilinolein, 3-substituted 5,6-bis(4-methoxyphenyl)-1,2,4-triazines; antibodies to glycoprotein IIb/IIIa; antiserotonin drugs, such as, for example, clopridogrel; sulfinpyrazone and the like; aspirin; dipyridamole; clofibrate; pyridinol carbamate; glucagon, caffeine; theophyllin pentoxifyllin; ticlopidine, and the like.

Suitable prostaglandins include, but are not limited to, naturally occurring prostaglandins such as, for example, arbaprostil, alprostadil, beraprost, bimatoprost, carboprost, cloprostenol, dimoxaprost, dinoprost, enprostil, enisoprost, fluprostenol, fenprostalene, froxiprost, gemeprost, latanoprost, limaprost, meteneprost, mexiprostil, misoprostol, misoprost, misoprostol acid, nocloprost, ONO 373, ornoprostil, prostalene, $PGE_1$, $PGE_2$, $PGF_1$, $PGF_{2\alpha}$, rioprostil, rosaprostol, remiprostol, sulprostone, tafluprost, trimoprostil, tiprostanide, travoprost, unoprostone, viprostol and viprostol. Suitable prostaglandins are described more fully in the literature, such as in Goodman and Gilman, The Pharmacological Basis of Therapeutics (9th Edition), McGraw-Hill, 1995; and the Merck Index on CD-ROM, 13$^{th}$ Edition; and on STN Express, file phar and file registry.

In some embodiments the prostaglandins are PGE1, cloprostenol, fluprostenol, latanoprost and travoprost.

Suitable proton pump inhibitors include, but are not limited to, disulprazole, esomeprazole, lansoprazole, leminoprazole, omeprazole, pantoprazole, rabeprazole, timoprazole, tenatoprazole, 2-(2-benzimidazolyl)-pyridine, tricyclic imidazole, thienopydidine benzimidazole, fluoroalkoxy substituted benzimidazole, dialkoxy benzimidazole, N-substituted 2-(pyridylalkenesulfinyl)benzimidazole, cycloheptenepyridine, 5-pyrrolyl-2-pyridylmethylsulfinyl benzimidazole, alkylsulfinyl benzimidazole, fluoro-pyridylmethylsulfinyl benzimidazole, imidazo(4,5-b)pydridine, RO 18-5362, IY 81149, 4-amino-3-carbonyl quinoline, 4-amino-3-acylnaphthyride, 4-aminoquinoline, 4-amino-3-acylquinoline, 3-butyryl-4-(2-methylphenylamino)-8-(2-hydroxyethoxy)quinoline, quinazoline, tetrahydroisoquinolin-2-yl pyrimidine, YH 1885, 3-substituted 1,2,4-thiadiazolo(4,5-a) benzimidazole, 3-substituted imidazo(1,2-d)-thiadiazole, 2-sulfinylnicotinamide, pyridylsulfinylbenz imidazole, pyridylsulfinyl thieno imidazole, theinoimidazole-toluidine, 4,5-dihydrooxazole, thienoimidazole-toluidine, Hoe-731, imidazo[1,2-a]pyridine, pyrrolo[2,3-b]pyridine, and the like. Suitable proton pump inhibitors are described more fully in the literature, such as in Goodman and Gilman, The Pharmacological Basis of Therapeutics (9th Edition), McGraw-Hill, 1995; the Merck Index on CD-ROM, 13$^{th}$ Edition; and in WO 00/50037 assigned to NitroMed. Inc., the disclosures of which are incorporated herein by reference in their entirety.

Suitable renin inhibitors include, but are not limited to, aldosterone, aliskiren (SPP-100), ditekiren, enalkrein (A-64662), medullipin, terlkiren, tonin, zankiren, RO 42-5892 (remikiren), A 62198, A 64662, A 65317, A 69729, A 72517 (zankiren), A 74273, CP 80794, CGP 29287, CGP-38560A, EMD 47942, ES 305, ES 1005, ES 8891, FK 906, FK 744, H 113, H-142, KRI 1314, pepstatin A, RO 44-9375 (ciprokiren), RO 42-5892, RO 66-1132, RO 66-1168, SP 500, SP 800, SR-43845, SQ 34017, U 71038, YM-21095, YM-26365, urea derivatives of peptides, amino acids connected by nonpeptide bonds, di- and tri-peptide derivatives (e.g., Act-A, Act-B, Act-C, ACT-D, and the like), amino acids and derivatives thereof, diol sulfonamides and sulfinyls, modified peptides, peptidyl beta-aminoacyl aminodiol carbamates, monoclonal antibodies to renin. Suitable renin inhibitors are described more fully in U.S. Pat. Nos. 5,116,835, 5,114,937, 5,106,835, 5,104,869, 5,095,119, 5,098,924), 5,095,006, 5,089,471, 5,075,451, 5,066,643, 5,063,208, 4,845,079, 5,055,466, 4,980,283, 4,885,292), 4,780,401, 5,071,837, 5,064,965, 5,063,207, 5,036,054, 5,036,053, 5,034,512, and 4,894,437, the disclosures of each of which are incorporated herein by reference in their entirety; and in the literature, such as in Goodman and Gilman, The Pharmacological Basis of Therapeutics (9th Edition), McGraw-Hill, 1995; and the Merck Index on CD-ROM, Thirteenth Edition; and on STN Express, file phar and file registry.

Suitable COX-2 inhibitors include, but are not limited to, nimesulide, celecoxib (CELEBREX®), etoricoxib (ARCOXIA®), flosulide, lumiracoxib (PREXIG®, COX-189), parecoxib (DYNSTAT®), rofecoxib (VIOXX®), tiracoxib (JTE-522), valdecoxib (BEXTRA®), ABT 963, BMS 347070, CS 502, DuP 697, GW-406381, NS-386, SC-57666, SC-58125, SC-58635, and the like, and mixtures of two or more thereof. Suitable COX-2 inhibitors are in U.S. Pat. Nos. 5,344,991, 5,380,738, 5,393,790, 5,409,944, 5,434,178, 5,436,265, 5,466,823, 5,474,995, 5,510,368, 5,536,752, 5,550,142, 5,552,422, 5,604,253, 5,604,260, 5,639,780, 5,932,598 and 6,633,272, and in WO 94/03387, WO 94/15723, WO 94/20480, WO 94/26731, WO 94/27980, WO 95/00501, WO 95/15316, WO 96/03387, WO 96/03388, WO 96/06840, WO 96/21667, WO 96/31509, WO 96/36623, WO 97/14691, WO 97/16435, WO 01/45703 and WO 01/87343, the disclosures of each of which are incorporated herein by reference in their entirety; and in the literature, such as in Goodman and Gilman, The Pharmacological Basis of Therapeutics (9th Edition), McGraw-Hill, 1995; and the Merck Index on CD-ROM, Thirteenth Edition; and on STN Express, file phar and file registry.

In some embodiments the COX-2 inhibitors are celecoxib, etoracoxib, lumiracoxib, paracoxib, rofecoxib or valdecoxib. In more particular embodiments the celecoxib is administered in an amount of about 100 milligrams to about 800 milligrams as a single dose or as multiple doses per day; the etoricoxib is administered in an amount of about 50 milligrams to about 200 milligrams as a single dose or as multiple doses per day; the lumiracoxib is administered in an amount of about 40 milligrams to about 1200 milligrams as a single dose or as multiple doses per day; the paracoxib is administered in an amount of about 20 milligrams to about 100 milligrams as a single dose or as multiple doses per day; the rofecoxib is administered in an amount of about 12.5 milligrams to about 50 milligrams as a single dose or as multiple doses per day; the valdecoxib is administered in an amount of about 10 milligrams to about 40 milligrams as a single dose or as multiple doses per day.

Suitable steroids include, but are not limited to, 21-acetoxypregnenolone, alcolometasone, algestone, amcinonide, beclomethasone, betamethasone, budesonide, chlorprednisone, clobetasol, clobentasone, clocortolone, cloprednol, corticosterone, cortisine, corticazol (cortivatol), deflazacort, desonide, desoximetasone, dexamethasone, diflorasone, diflucortolone, difluprednate, enoxolone, fluazacort, flucloronide, flumethasone, flunisolide, flucinolone acetonide, fluocininide, fluocortin butyl, fluocortolone, fluorometholone, fluperolone acetate, fluprednidene acetate, fluprednisolone, flurandrenolide, fluticasone propionate, fluticasone propionate, formocortal, halcinonide, halobetasol propionate, halometasone, haloprednone acetate, hydrocortamate, hydrocortisone and its derivatives (such as phosphate, 21-sodium succinate and the like), hydrocortisone terbutate, isoflupredone, loteprednol etabonate, mazipredone, medrysone, meprednisone, methylprednisolone, mometasone furoate, paremethasone, prednicarbate, prednisolone and its derivatives (such as 21-stearoylglycolate, sodium phosphate and the like), prednisone, prednival, prednylidene and its derivatives (such as 21-diethylaminoactetate and the like), rimexolone, tixocortol, trimcinolone and its derivatives (such as acetonide, benetonide and the like), and the like. Suitable NSAIDs are described more fully in the literature, such as in Goodman and Gilman, The Pharmacological Basis of Therapeutics (9th Edition), McGraw-Hill, 1995, Pgs. 617-657; the Merck Index on CD-ROM, 13$^{th}$ Edition; and in U.S. Pat. Nos. 6,057,347 and 6,297,260 assigned to NitroMed. Inc., the disclosures of which are incorporated herein by reference in their entirety.

In some embodiments the steroids are dexamethasone, fluorometholone, hydrocortisone, and prednisolone.

Suitable compounds used for the treatment of glaucoma include, but are not limited to, acetylcholinesterase inhibitors (such as, for example, citicoline, donepezil, heptatigmine, galantamine, metafonate, physostignine, rivastignine, tarcine, velnacrine, and the like) carbachol, pilocarpine and the like. Suitable compounds used for the treatment of glaucoma are described more fully in the literature, such as in Goodman and Gilman, The Pharmacological Basis of Therapeutics (9th Edition), McGraw-Hill, 1995; and the Merck Index on CD-ROM, 13$^{th}$ Edition; and on STN Express, file phar and file registry.

The invention provides compositions comprising (i) a nitric oxide enhancing prostaglandin compound or a pharmaceutically acceptable salt thereof, (ii) a nitric oxide enhancing compound, such as, isosorbide dinitrate and/or isosorbide mononitrate (preferably isosorbide dinitrate), and (i) a hydralazine compound (such as hydralazine hydrochloride). In one embodiment, the hydralazine hydrochloride can be administered in an amount of about 30 milligrams per day to about 400 milligrams per day; the isosorbide dinitrate can be administered in an amount of about 10 milligrams per day to about 200 milligrams per day; or the isosorbide mononitrate can be administered in an amount of about 5 milligrams per day to about 120 milligrams per day. In another embodiment, the hydralazine hydrochloride can be administered in an amount of about 50 milligrams per day to about 300 milligrams per day; the isosorbide dinitrate can be administered in an amount of about 20 milligrams per day to about 160 milligrams per day; or the isosorbide mononitrate can be administered in an amount of about 15 milligrams per day to about 100 milligrams per day. In yet another embodiment, the hydralazine hydrochloride can be administered in an amount of about 37.5 milligrams to about 75 milligrams one to four times per day; the isosorbide dinitrate can be administered in an amount of about 20 milligrams to about 40 milligrams one to four times per day; or the isosorbide mononitrate can be administered in an amount of about 10 milligrams to about 20 milligrams one to four times per day. In another embodiment of the methods of the invention, the patient can be administered a composition comprising about 225 mg hydralazine hydrochloride and about 120 mg isosorbide dinitrate once per day (i.e., q.d.). In another embodiment of the methods of the invention, the patient can be administered a composition comprising about 112.5 mg hydralazine hydrochloride and about 60 mg isosorbide dinitrate twice per day (i.e., b.i.d.). In another embodiment of the methods of the invention, the patient can be administered a composition comprising about 56.25 mg hydralazine hydrochloride and about 30 mg isosorbide dinitrate twice per day (i.e., b.i.d.). In another embodiment of the methods of the invention, the patient can be administered a composition comprising about 75 mg hydralazine hydrochloride and about 40 mg isosorbide dinitrate three times per day (i.e., t.i.d.). In another embodiment of the methods of the invention, the patient can be administered a composition comprising about 37.5 mg hydralazine hydrochloride and about 20 mg isosorbide dinitrate three times per day (i.e., t.i.d.). The particular amounts of hydralazine and isosorbide dinitrate or isosorbide mononitrate can be administered as a single dose once a day; or in multiple doses several times throughout the day; or as a sustained-release oral formulation, or as an injectable formulation.

The invention provides methods for treating ophthalmic disorders by administering to the patient in need thereof an effective amount of the compounds and/or compositions described herein. For example, the patient can be administered an effective amount of at least one nitric oxide enhancing prostaglandin compound. In another embodiment, the patient can be administered an effective amount of at least one nitric oxide enhancing prostaglandin compound, and at least one nitric oxide enhancing compound. In yet another embodiment, the patient can be administered an effective amount of at least one nitric oxide enhancing prostaglandin compound, and, at least one therapeutic agent, including but not limited to, such as, for example, aldosterone antagonists, α-adrenergic receptor agonists, α-adrenergic receptor antagonists, β-adrenergic agonists, antidiabetic compounds, antimicrobial compounds, anti-hyperlipidemic drugs, angiotensin II antagonists, angiotensin-converting enzyme (ACE) inhibitors, antioxidants, antithrombotic and vasodilator drugs, β-adrenergic antagonists, calcium channel blockers, carbonic anhydrase inhibitors, diuretics, endothelin antagonists, hydralazine compounds, $H_2$ receptor antagonists, neutral endopeptidase inhibitors, nonsteroidal antiinflammatory compounds (NSAIDs), phosphodiesterase inhibitors, potassium channel blockers, platelet reducing agents, prostaglandins, proton pump inhibitors, renin inhibitors, selective cyclooxygenase-2 (COX-2) inhibitors, steroids, compounds used for the treatment of glaucoma, and combinations of two or more thereof. In another embodiment, the patient can be administered an effective amount of at least one nitric oxide enhancing prostaglandin compound, and, at least one therapeutic agent, and, at least one nitric oxide enhancing compound. In one embodiment the ophthalmic disorder is glaucoma, elevated ocular pressure, macular degeneration, ophthalmic infection, dry eye disorder, ocular hypertension, and diabetic retinopathy. The nitric oxide enhancing prostaglandin compounds, nitric oxide enhancing compounds, and/or therapeutic agents can be administered separately or as components of the same composition in one or more pharmaceutically acceptable carriers.

The invention provides methods for treating cerebrovascular disorders; treating cardiovascular disorders; treating benign prostatic hyperplasia (BPH); treating peptic ulcers; treating sexual dysfunctions and inducing abortions by administering to the patient in need thereof an effective amount of the compounds and/or compositions described herein. For example, the patient can be administered an effective amount of at least one nitric oxide enhancing prostaglandin compound. In another embodiment, the patient can be administered an effective amount of at least one nitric oxide enhancing prostaglandin compound, and at least one nitric oxide enhancing compound. In yet another embodiment, the patient can be administered an effective amount of at least one nitric oxide enhancing prostaglandin compound, and, at least one therapeutic agent including, but not limited to, such as, for example, aldosterone antagonists, α-adrenergic receptor agonists, α-adrenergic receptor antagonists, β-adrenergic agonists, antidiabetic compounds, antimicrobial compounds, anti-hyperlipidemic drugs, angiotensin II antagonists, angiotensin-converting enzyme (ACE) inhibitors, antioxidants, antithrombotic and vasodilator drugs, β-adrenergic antagonists, calcium channel blockers, carbonic anhydrase inhibitors, diuretics, endothelin antagonists, hydralazine compounds, $H_2$ receptor antagonists, neutral endopeptidase inhibitors, nonsteroidal antiinflammatory compounds (NSAIDs), phosphodiesterase inhibitors, potassium channel blockers, platelet reducing agents, prostaglandins, proton pump inhibitors, renin inhibitors, selective cyclooxygenase-2 (COX-2) inhibitors, steroids, compounds used for the treatment of glaucoma, and combinations of two or more thereof. In another embodiment, the patient can be administered an effective amount of at least one nitric oxide enhancing prostaglandin compound, and, at least one therapeutic agent, and, at least one nitric oxide enhancing compound. The nitric oxide enhancing prostaglandin compounds, nitric oxide enhancing compounds, and/or therapeutic agents can be administered separately or as components of the same composition in one or more pharmaceutically acceptable carriers.

When administered separately, the nitric oxide enhancing prostaglandin compound, nitric oxide enhancing compound and/or therapeutic agent can be administered about the same time as part of the overall treatment regimen, i.e., as a combination therapy. "About the same time" includes administering the nitric oxide enhancing prostaglandin compound, simultaneously, sequentially, at the same time, at different times on the same day, or on different days, as long as they are administered as part of an overall treatment regimen, i.e., combination therapy or a therapeutic cocktail.

When administered in vivo, the compounds and compositions of the invention can be administered in combination with pharmaceutically acceptable carriers and in dosages described herein. When the compounds and compositions of the invention are administered as a combination of at least one nitric oxide enhancing prostaglandin compound and/or at least one nitric oxide enhancing compound and/or therapeutic agent, they can also be used in combination with one or more additional compounds which are known to be effective against the specific disease state targeted for treatment. The nitric oxide enhancing compounds, therapeutic agents and/or other additional compounds can be administered simultaneously with, subsequently to, or prior to administration of the nitric oxide enhancing prostaglandin compound.

The compounds of the invention can be incorporated into various types of pharmaceutical compositions, such as, for example, ophthalmic formulations for delivery to the eye (e.g., topically, intracamerally, or via an implant). The compounds are preferably incorporated into topical ophthalmic formulations, such as for example, solutions, suspensions, gels, ointments, implants, and the like. The compounds of the invention may be combined with ophthalmologically acceptable preservatives, viscosity enhancers, penetration enhancers, buffers, sodium chloride, water to form an aqueous, sterile ophthalmic suspensions or solutions, and the like.

Suitable preservatives include, but are not limited to, benzalkonium chloride, thimerosal, chlorobutanol, methyl paraben, propyl paraben, phenylethyl alcohol, edetate disodium, sorbic acid, ONAMER®, and the like. The preservatives are typically employed at a concentration between about 0.001% and about 1.0% by weight. Appropriate co-solvents include, but are not limited to, Polysorbate 20, 60 and 80; Pluronic F-68, F-84 and P-103; Tyloxapol®; Cremophor® EL; sodium dodecyl sulfate; glycerol; PEG 400; propylene glycol; cyclodextrins, and the like. The co-solvents are typically employed at a concentration between about 0.01% and about 2% by weight. Viscosity enhancers are required as a viscosity greater than that of simple aqueous solutions may be desirable to increase ocular absorption of the active compound, to decrease variability in dispensing the formulations, to decrease physical separation of components of a suspension or emulsion of formulation and/or otherwise to improve the ophthalmic formulation. Suitable viscosity enhancers, include, but are not limited to, polyvinyl alcohol, methyl cellulose, hydroxy propyl carboxymethyl cellulose, hydroxymethylcellulose, hydroxyethylcellulose, hydroxypropylmethylcellulose, methylcellulose, polyvinylpyrrolidone, and the like. Gelling agents can also be used, including, but not limited to, gellan and xanthan gum, and the like. Viscosity enhancers are typically employed at a concentration between about 0.01% and about 2% by weight.

Ophthalmic solution formulations may be prepared by dissolving a compound in a physiologically acceptable isotonic aqueous buffer. Alternatively, the ophthalmic solution may include an ophthalmologically acceptable surfactant to assist in dissolving the compound. Additionally for sterile ophthalmic ointment formulations, the compounds of the invention may be combined with a preservative in an appropriate vehicle, such as, mineral oil, liquid lanolin, or white petrolatum. Sterile ophthalmic gel formulations may be prepared by suspending the active ingredient in a hydrophilic base prepared from the combination of, for example, carbopol-974, and the like.

Various delivery systems are known and can be used to administer the compounds or compositions of the invention, including, for example, encapsulation in liposomes, microbubbles, emulsions, microparticles, microcapsules and the like. The required dosage can be administered as a single unit or in a sustained release form.

The bioavailability of the compositions can be enhanced by micronization of the formulations using conventional techniques such as grinding, milling, spray drying and the like in the presence of suitable excipients or agents such as phospholipids or surfactants.

Sustained release dosage forms of the invention may comprise microparticles and/or nanoparticles having a therapeutic agent dispersed therein or may comprise the therapeutic agent in pure, preferably crystalline, solid form. For sustained release administration, microparticle dosage forms comprising pure, crystalline, therapeutic agents. The therapeutic dosage forms of this aspect of the invention may be of any configuration suitable for sustained release.

Nanoparticle sustained release therapeutic dosage forms are preferably biodegradable and, optionally, bind to the vascular smooth muscle cells and enter those cells, primarily by endocytosis. The biodegradation of the nanoparticles occurs over time (e.g., 30 to 120 days; or to 21 days) in prelysosomic vesicles and lysosomes. Larger microparticle therapeutic dosage forms of the invention release the therapeutic agents for subsequent target cell uptake with only a few of the smaller microparticles entering the cell by phagocytosis. A practitioner in the art will appreciate that the precise mechanism by which a target cell assimilates and metabolizes a dosage form of the invention depends on the morphology, physiology and metabolic processes of those cells. The size of the particle sustained release therapeutic dosage forms is also important with respect to the mode of cellular assimilation. For example, the smaller nanoparticles can flow with the interstitial fluid between cells and penetrate the infused tissue. The larger microparticles tend to be more easily trapped interstitially in the infused primary tissue, and thus are useful to deliver anti-proliferative therapeutic agents.

Particular sustained release dosage forms of the invention comprise biodegradable microparticles or nanoparticles. More particularly, biodegradable microparticles or nanoparticles are formed of a polymer containing matrix that biodegrades by random, nonenzymatic, hydrolytic scissioning to release therapeutic agent, thereby forming pores within the particulate structure.

The compounds and compositions of the invention can be formulated as pharmaceutically acceptable salt forms. Pharmaceutically acceptable salts include, for example, alkali metal salts and addition salts of free acids or free bases. The nature of the salt is not critical, provided that it is pharmaceutically-acceptable. Suitable pharmaceutically-acceptable acid addition salts may be prepared from an inorganic acid or from an organic acid. Examples of such inorganic acids include, but are not limited to, hydrochloric, hydrobromic, hydroiodic, nitric, carbonic, sulfuric and phosphoric acid and the like. Appropriate organic acids include, but are not limited to, aliphatic, cycloaliphatic, aromatic, heterocyclic, carboxylic and sulfonic classes of organic acids, such as, for example, formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, salicylic, p-hydroxybenzoic, phenylacetic, mandelic, embonic (pamoic), methanesulfonic, ethanesulfonic, benzenesulfonic, pantothenic, toluenesulfonic, 2-hydroxyethanesulfonic, sulfanilic, stearic, algenic, β-hydroxybutyric, cyclohexylaminosulfonic, galactaric and galacturonic acid and the like. Suitable pharmaceutically-acceptable base addition salts include, but are not limited to, metallic salts made from aluminum, calcium, lithium, magnesium, potassium, sodium and zinc or organic salts made from primary, secondary and tertiary amines, cyclic amines, N,N'-dibenzylethylenediamine, chloroprocaine, choline, diethanolamine, ethylenediamine, meglumine (N-methylglucamine) and procaine and the like. All of these salts may be prepared by conventional means from the corresponding compound by reacting, for example, the appropriate acid or base with the compound. In one embodiment, the pharmaceutically acceptable salts of the compounds of the invention do not include the nitrate salt.

While individual needs may vary, determination of optimal ranges for effective amounts of the compounds and/or compositions is within the skill of the art. Generally, the dosage required to provide an effective amount of the compounds and compositions, which can be adjusted by one of ordinary skill in the art, will vary depending on the age, health, physical condition, sex, diet, weight, extent of the dysfunction of the recipient, frequency of treatment and the nature and scope of the dysfunction or disease, medical condition of the patient, the route of administration, pharmacological considerations such as the activity, efficacy, pharmacokinetic and toxicology profiles of the particular compound used, whether a drug delivery system is used, and whether the compound is administered as part of a drug combination.

The amount of a given prostaglandin compound of the invention compound comprising at least one nitric oxide enhancing group that will be effective in the treatment of a particular disorder or condition will depend on the nature of the disorder or condition, and can be determined by standard clinical techniques, including reference to Goodman and Gilman, supra; The Physician's Desk Reference, Medical Economics Company, Inc., Oradell, N.J., 1995; and Drug Facts and Comparisons, Inc., St. Louis, Mo., 1993. The precise dose to be used in the formulation will also depend on the route of administration, and the seriousness of the disease or disorder, and should be decided by the physician and the patient's circumstances.

The invention also provides pharmaceutical kits comprising one or more containers filled with one or more of the ingredients of the pharmaceutical compounds and/or compositions of the invention, including, at least, one or more of the novel nitric oxide enhancing prostaglandin compound, and one or more of the nitric oxide enhancing compounds described herein. Associated with such kits can be additional therapeutic agents or compositions (e.g., aldosterone antagonists, α-adrenergic receptor agonists, α-adrenergic receptor antagonists, β-adrenergic agonists, antidiabetic compounds, antimicrobial compounds, anti-hyperlipidemic drugs, angiotensin II antagonists, angiotensin-converting enzyme (ACE) inhibitors, antioxidants, antithrombotic and vasodilator drugs, β-adrenergic antagonists, calcium channel blockers, carbonic anhydrase inhibitors, diuretics, endothelin antagonists, hydralazine compounds, $H_2$ receptor antagonists, neutral endopeptidase inhibitors, nonsteroidal antiinflammatory compounds (NSAIDs), phosphodiesterase inhibitors, potassium channel blockers, platelet reducing agents, prostaglandins, proton pump inhibitors, renin inhibitors, selective cyclooxygenase-2 (COX-2) inhibitors, steroids, compounds used for the treatment of glaucoma, and combinations of two or more thereof), devices for administering the compositions, and notices in the form prescribed by a governmental agency regulating the manufacture, use or sale of pharmaceuticals or biological products which reflects approval by the agency of manufacture, use or sale for humans.

The disclosure of each patent, patent application and publication cited or described in the present specification is hereby incorporated by reference herein in its entirety.

Although the invention has been set forth in detail, one skilled in the art will appreciate that numerous changes and modifications can be made to the invention, and that such changes and modifications can be made without departing from the spirit and scope of the invention.

What is claimed is:

1. A method for treating glaucoma, elevated ocular pressure or ocular hypertension in a patient in need thereof comprising administering to the patient an effective amount of a composition comprising a pharmaceutically acceptable carrier and a nitric oxide enhancing arbaprostil compound of Formula (II), a nitric oxide enhancing alprostadil or $PGE_1$ compound of Formula (III), a nitric oxide enhancing bimatoprost compound of Formula (IV), a nitric oxide enhancing carboprost compound of Formula (V), a nitric oxide enhancing cloprostenol compound of Formula (VI), a nitric oxide enhancing dimoxaprost compound of Formula (VII), a nitric oxide enhancing dinoprost compound of Formula (VIII), a nitric oxide enhancing enprostil compound of Formula (IX), a nitric oxide enhancing enisoprost compound of Formula (X), a nitric oxide enhancing fenprostalene compound of Formula (XI), a nitric oxide enhancing froxiprost compound of Formula (XII), a nitric oxide enhancing gemeprost compound of Formula (XIII), a nitric oxide enhancing latanoprost compound of Formula (XIV), a nitric oxide enhancing meteneprost compound of Formula (XV), a nitric oxide enhancing mexiprostil compound of Formula (XVI), a nitric oxide enhancing misoprostol compound of Formula (XVII), a nitric oxide enhancing misoprostol acid compound of Formula (XVIII), a nitric oxide enhancing nocloprost compound of Formula (XIX), a nitric oxide enhancing ONO 373 compound of Formula (XX), a nitric oxide enhancing ornoprostil compound of Formula (XXI), a nitric oxide enhancing prostalene compound of Formula (XXII), a nitric oxide enhancing $PGE_2$ compound of Formula (XOH), a nitric oxide enhancing $PGF_1$ compound of Formula (XXIV), a nitric oxide enhancing $PGF_{2\alpha}$ compound of Formula (XXV), a nitric oxide enhancing rioprostil compound of Formula (XXVI), a nitric oxide enhancing rosaprostol compound of Formula (XXVII), a nitric oxide enhancing remiprostol compound of Formula (XXVIII), a nitric oxide enhancing sulprostone compound of Formula (XXIX), a nitric oxide enhancing tafluprost compound of Formula (XXX), a nitric oxide enhancing travoprost compound of Formula (XXXI), a nitric oxide enhancing trimoprostil compound of Formula (XXXII), a nitric oxide enhancing tiprostanide compound of Formula (XXXIII), a nitric oxide enhancing unoprostone compound of Formula (XXXIV), and pharmaceutically acceptable salts thereof;

wherein the compound of Formula (II) is:

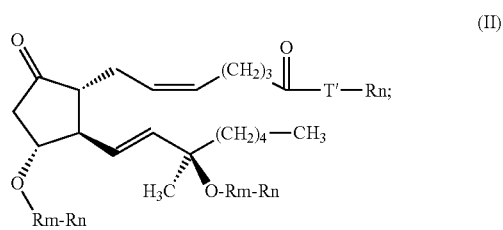

(II)

wherein the compound of Formula (III) is:

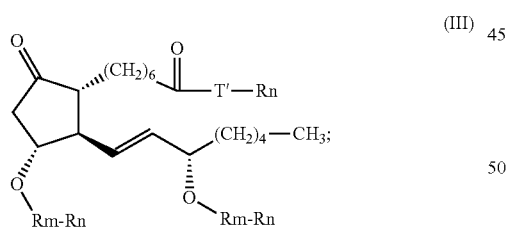

(III)

wherein the compound of Formula (IV) is:

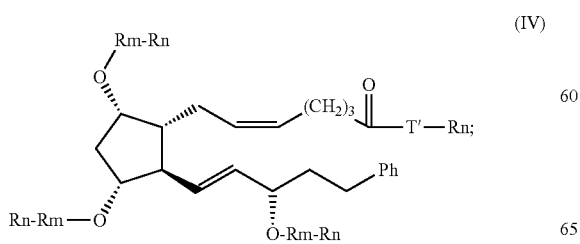

(IV)

wherein the compound of Formula (V) is:

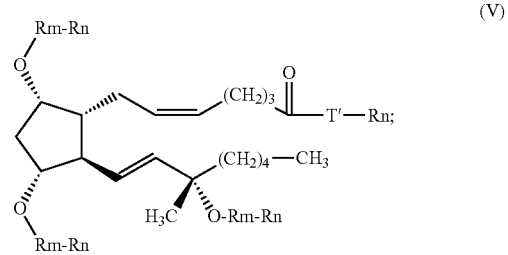

(V)

wherein the compound of Formula (VI) is:

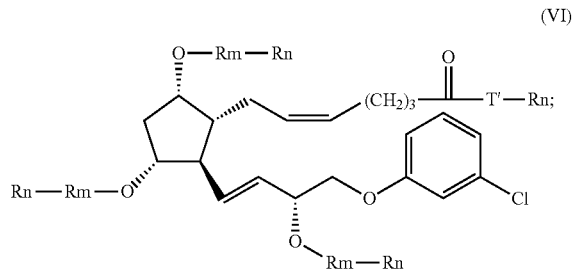

(VI)

wherein the compound of Formula (VII) is:

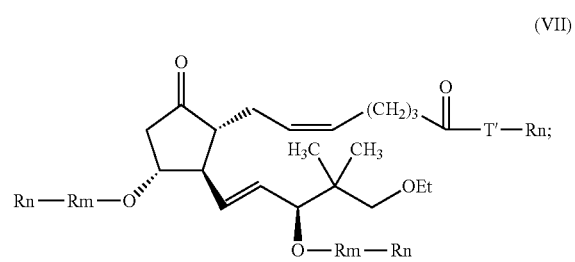

(VII)

wherein the compound of Formula (VIII) is:

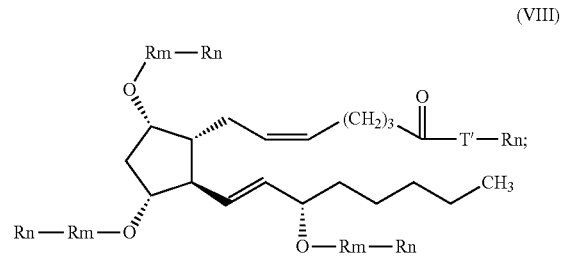

(VIII)

wherein the compound of Formula (IX) is:

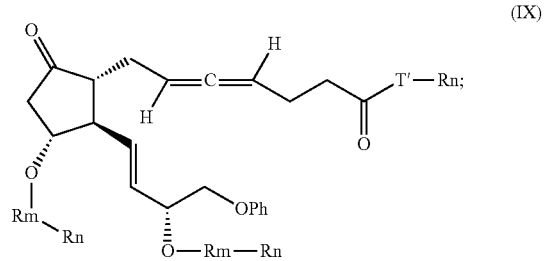

(IX)

wherein the compound of Formula (X) is:

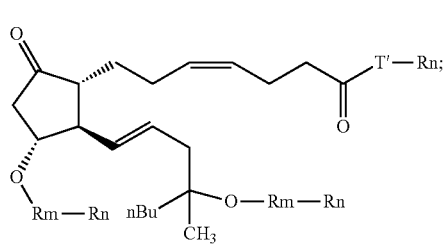
(X)

wherein the compound of Formula (XI) is:

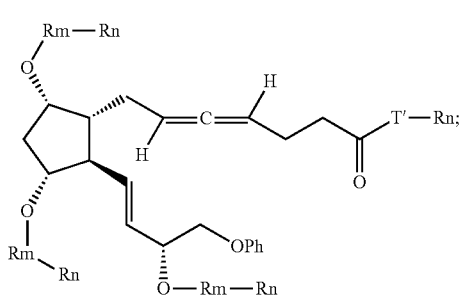
(XI)

wherein the compound of Formula (XII) is:

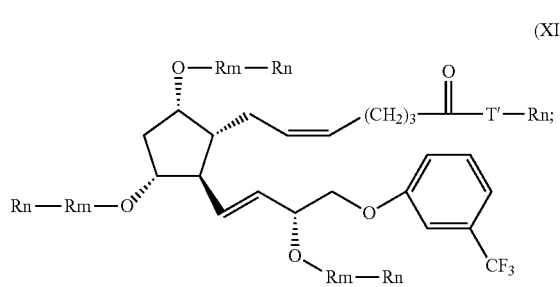
(XII)

wherein the compound of Formula (XIII) is:

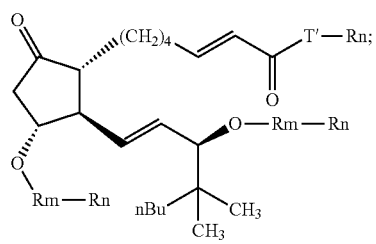
(XIII)

wherein the compound of Formula (XIV) is:

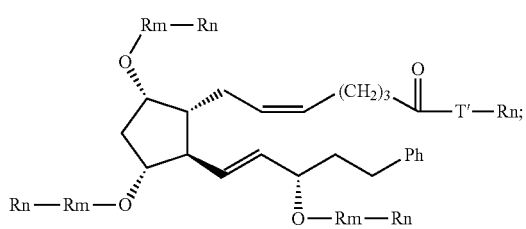
(XIV)

wherein the compound of Formula (XV) is:

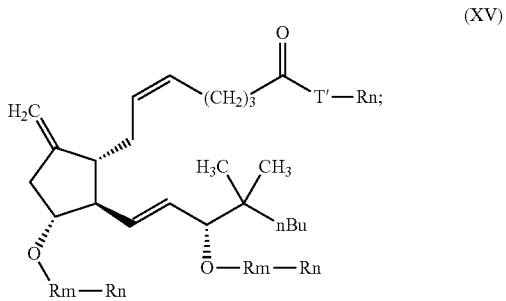
(XV)

wherein the compound of Formula (XVI) is:

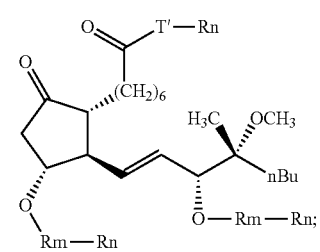
(XVI)

wherein the compound of Formula (XVII) is:

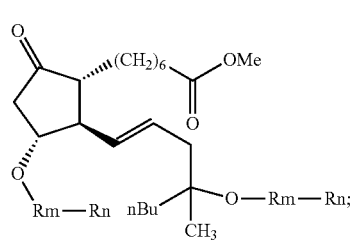
(XVII)

wherein the compound of Formula (XVIII) is:

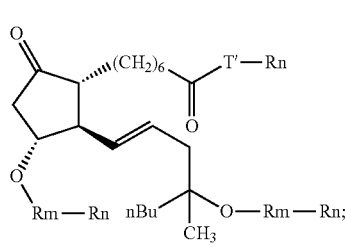
(XVIII)

wherein the compound of Formula (XIX) is:

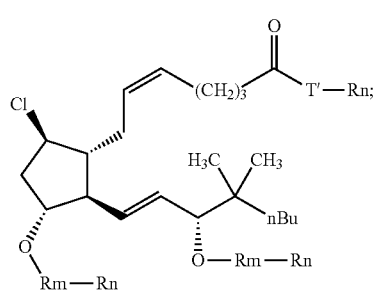
(XIX)

wherein the compound of Formula (XX) is:

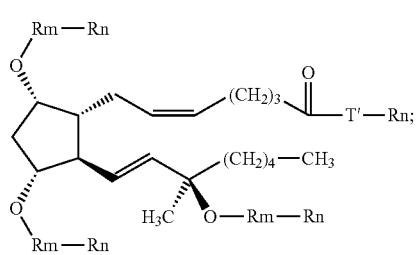
(XX)

wherein the compound of Formula (XXI) is:

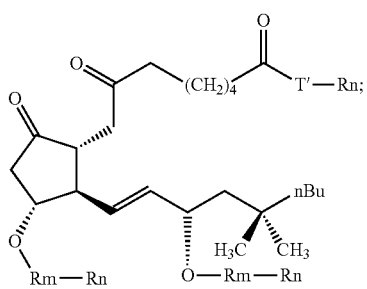
(XXI)

wherein the compound of Formula (XXII) is:

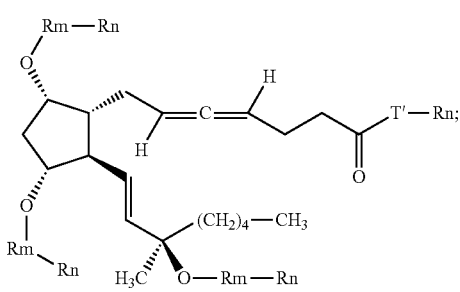
(XXII)

wherein the compound of Formula (XXIII) is:

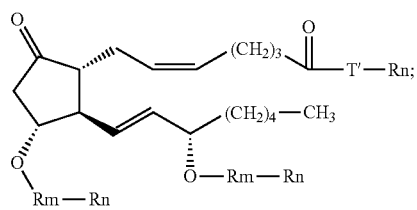
(XXIII)

wherein the compound of Formula (XXIV) is:

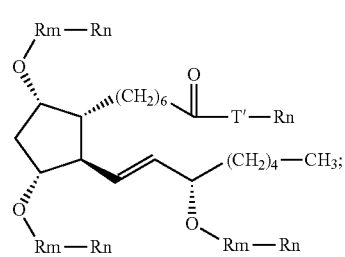
(XXIV)

wherein the compound of Formula (XXV) is:

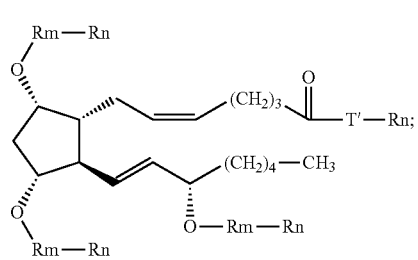
(XXV)

wherein the compound of Formula (XXVI) is:

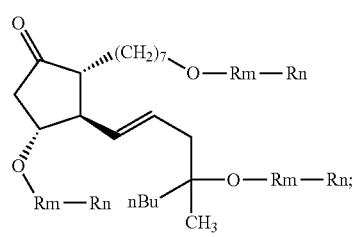
(XXVI)

wherein the compound of Formula (XXVII) is:

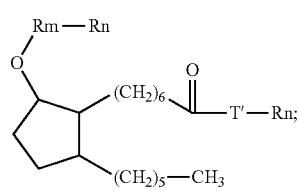
(XXVII)

wherein the compound of Formula (XXVIII) is:

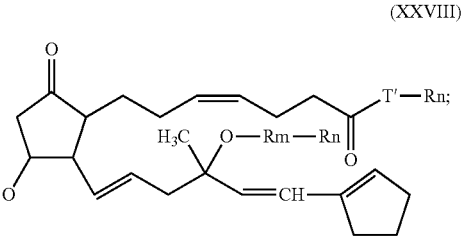
(XXVIII)

wherein the compound of Formula (XXIX) is:

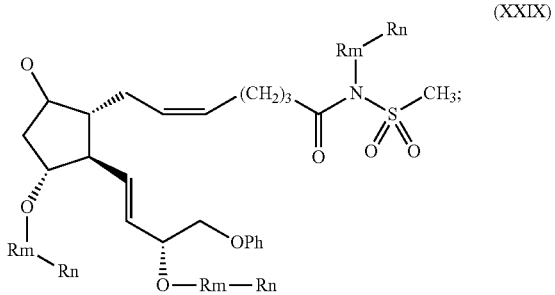
(XXIX)

wherein the compound of Formula (XXX) is:

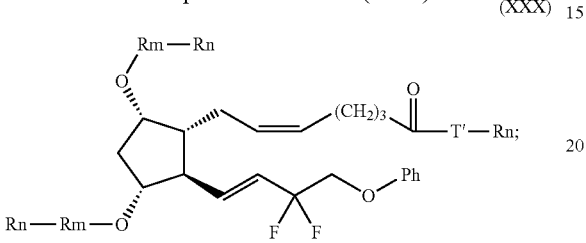
(XXX)

wherein the compound of Formula (XXXI) is:

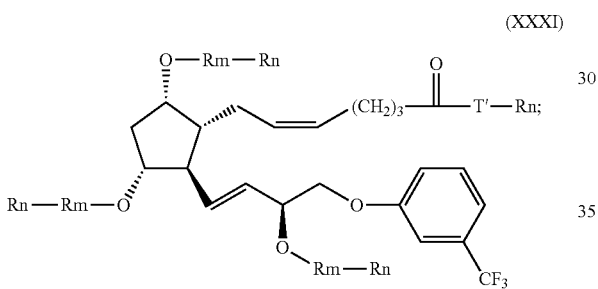
(XXXI)

wherein the compound of Formula (XXXII) is:

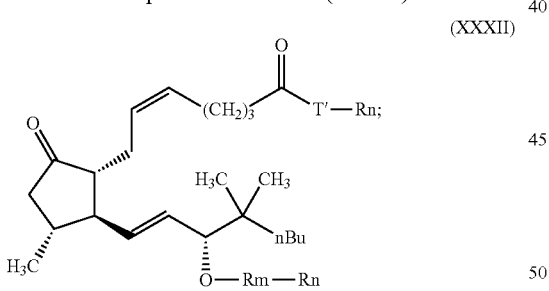
(XXXII)

wherein the compound of Formula (XXXIII) is:

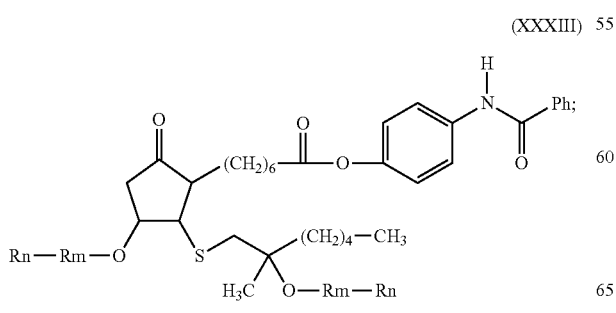
(XXXIII)

wherein the compound of Formula (XXXIV) is:

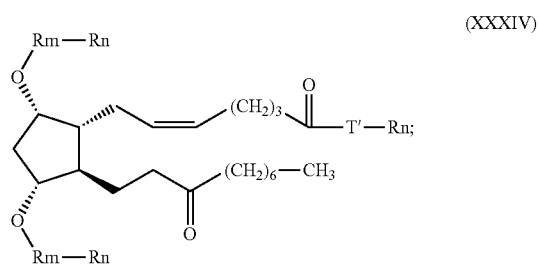
(XXXIV)

wherein:
T' is oxygen, sulfur or $NR_{16}$;
nBu is the lower alkyl group $CH_3$—$CH_2$-$CH_2$—$CH_2$-;
OEt is the alkoxy group —$OCH_2$—$CH_3$;
OPh is the alkoxy group —$OC_6H_5$;
Ph is a aryl group —$C_6H_5$;
$R_{16}$ is a hydrogen, a lower alkyl group, an aryl group;
wherein
$R_m$-$R_n$ taken together are a hydrogen atom; or
$R_m$ is:
    (i) —C—(O)—;
    (ii) —C—(O)—$NR_{16}$;
    (iii) —C(O)—O—;
    (iv) —C(O)—S;
    (v) —$CH_2$—O—;
    (vi) —$CH(CH_3)$—O—;
    (vii) a covalent bond;
    (viii) —$(C—(R_e)(R_f))_{2-5}$—;
    (ix) —$(C—(R_e)(R_f))_{2-5}$—T'-;
    (x) —$(C—(R_e)(R_f))_{2-5}$—T'—C(O)—;
    (xi) —N—C(O)—S—;
    (xii) —N—C(O)—$CH_2$—; or
    (xiii) —N—C(O)—O—;
$R_n$ is:
a hydrogen or:

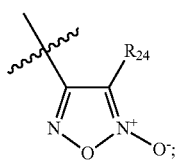
(1)

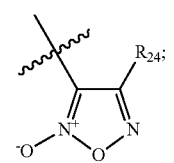
(2)

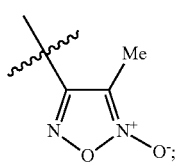
(3)

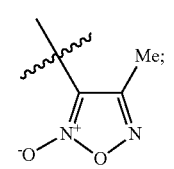
(4)

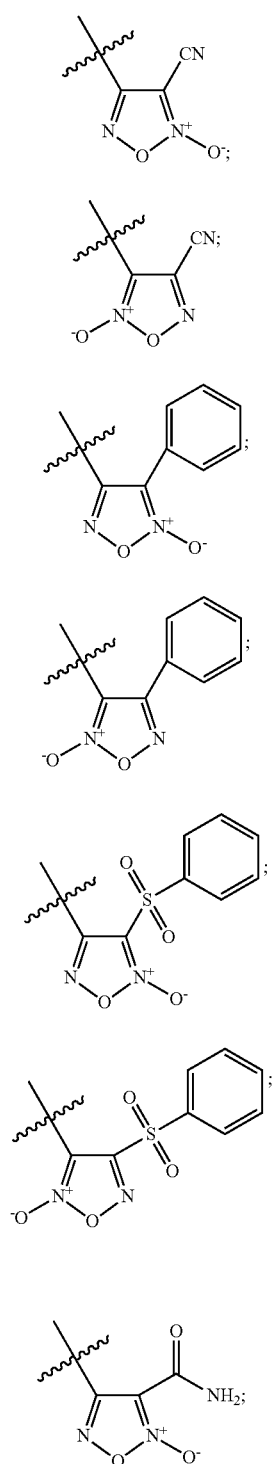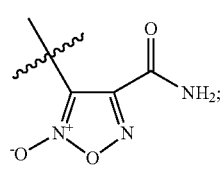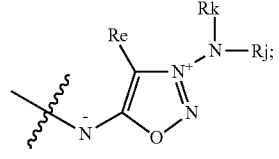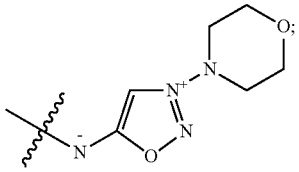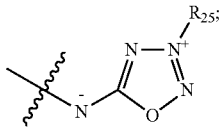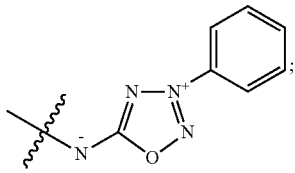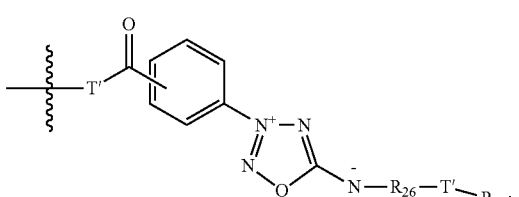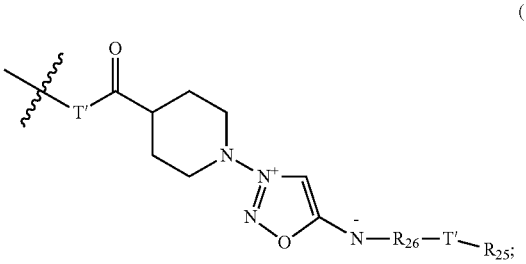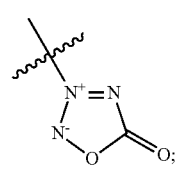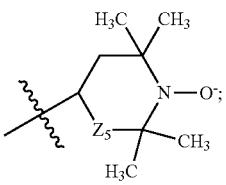

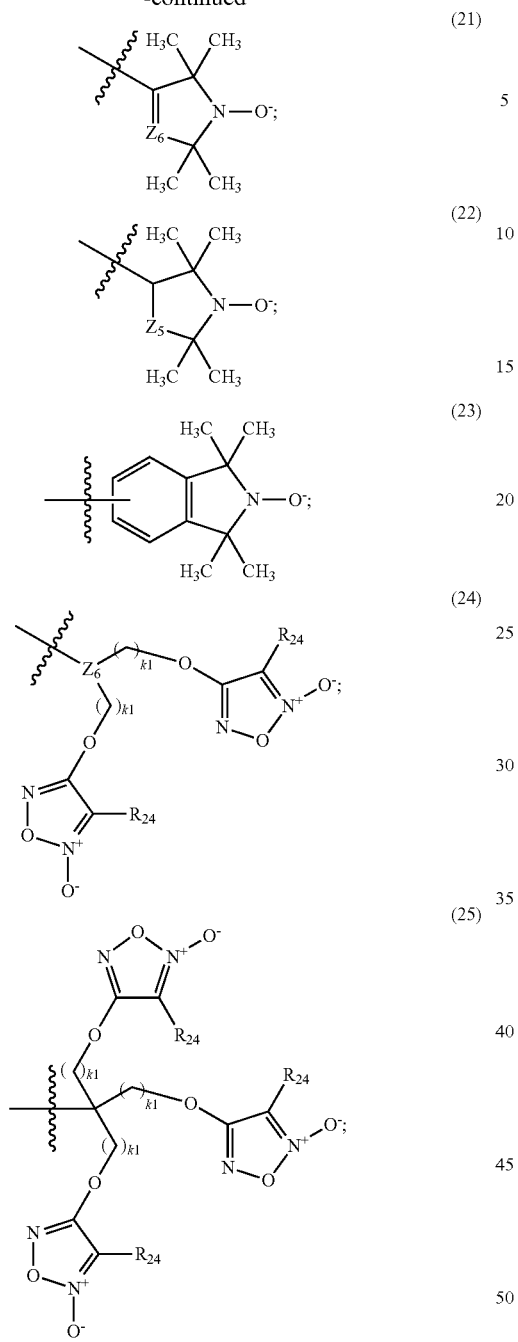

$Z_5$ is —$CH_2$ or oxygen;
$Z_6$ is —CH or nitrogen;
$R_{24}$ is —$C_6H_4R_{37}$, —CN, —$S(O)_2$—$C_6H_4R_{37}$, —C(O)—$N(R_a)(R_i)$, —$NO_2$, —C(O)—$OR_{25}$ or —$S(O)_2$—$R_{25}$;
$R_{25}$ is an aryl group, a lower alkyl group, a haloalkyl group, a hydroxyalkyl group or an arylalkyl group;
$R_{26}$ is —C(O)— or —$S(O)_2$—;
$R_{37}$ is a hydrogen, —CN, —$S(O)_2$—$R_{25}$, —C(O)—N$(R_a)(R_i)$, —$NO_2$ or —C(O)—$OR_{25}$;
T' is oxygen, sulfur or $NR_{16}$;
$k_1$ is an integer from 1 to 3;
$R_e$ and $R_f$ are each independently a hydrogen, an alkyl, a cycloalkoxy, a halogen, a hydroxy, an hydroxyalkyl, an alkoxyalkyl, an arylheterocyclic ring, an alkylaryl, an alkylcycloalkyl, an alkylheterocyclic ring, a cycloalkylalkyl, a cycloalkylthio, an arylalklythio, an arylalklythioalkyl, an alkylthioalkyl, a cycloalkenyl, an heterocyclicalkyl, an alkoxy, a haloalkoxy, an amino, an alkylamino, a dialkylamino, an arylamino, a diarylamino, an alkylarylamino, an alkoxyhaloalkyl, a sulfonic acid, a sulfonic ester, an alkylsulfonic acid, an arylsulfonic acid, an arylalkoxy, an alkylthio, an arylthio, a cyano, an aminoalkyl, an aminoaryl, an aryl, an arylalkyl, an alkylaryl, a carboxamido, an alkylcarboxamido, an arylcarboxamido, an amidyl, a carboxyl, a carbamoyl, an alkylcarboxylic acid, an arylcarboxylic acid, an alkylcarbonyl, an arylcarbonyl, an ester, a carboxylic ester, an alkylcarboxylic ester, an arylcarboxylic ester, a sulfonamido, an alkylsulfonamido, an arylsulfonamido, an alkylsulfonyl, an alkylsulfonyloxy, an arylsulfonyl, arylsulphonyloxy, a sulfonic ester, an alkyl ester, an aryl ester, a urea, a phosphoryl, a nitro, —$U_3$—$V_5$, $V_6$, —$(C(R_o)(R_p))_{k1}$—$U_3$—$V_5$, —$(C(R_o)(R_p))_{k1}$—$U_3$—$V_3$, —$(C(R_o)(R_p))_{k1}$—$U_3$—$V_6$, —$(C(R_o)(R_p))_{k1}$—$U_3$—C(O)—$V_6$, or $R_e$ and $R_f$ taken together with the carbons to which they are attached form a carbonyl, a methanthial, a heterocyclic ring, a cycloalkyl group, an aryl group, an oxime, an imine, a hydrazone, a bridged cycloalkyl group,

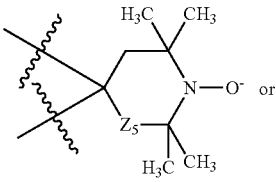

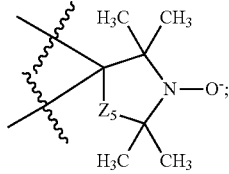

$R_o$ and $R_p$ are each independently a hydrogen, an alkyl, a cycloalkoxy, a halogen, a hydroxy, an hydroxyalkyl, an alkoxyalkyl, an arylheterocyclic ring, an alkylaryl, an alkylcycloalkyl, an alkylheterocyclic ring, a cycloalkylalkyl, a cycloalkylthio, an arylalklythio, an arylalklythioalkyl, an alkylthioalkyl a cycloalkenyl, an heterocyclicalkyl, an alkoxy, a haloalkoxy, an amino, an alkylamino, a dialkylamino, an arylamino, a diarylamino, an alkylarylamino, an alkoxyhaloalkyl, a sulfonic acid, a sulfonic ester, an alkylsulfonic acid, an arylsulfonic acid, an arylalkoxy, an alkylthio, an arylthio, a cyano an aminoalkyl, an aminoaryl, an aryl, an arylalkyl, an alkylaryl, a carboxamido, an alkylcarboxamido, an arylcarboxamido, an amidyl, a carboxyl, a carbamoyl, an alkylcarboxylic acid, an arylcarboxylic acid, an alkylcarbonyl, an arylcarbonyl, an ester, a carboxylic ester, an alkylcarboxylic ester, an arylcarboxylic ester, a sulfonamido, an alkylsulfonamido, an arylsulfonamido, an alkylsulfonyl, an alkylsulfonyloxy, an arylsulfonyl, arylsulphonyloxy, a sulfonic ester, an alkyl ester, an aryl ester, a urea, a phosphoryl, a nitro, —$U_3$—$V_5$, $V_6$, or $R_o$ and $R_p$ taken together with the carbons to which they are attached form a carbonyl, a methanthial, a heterocyclic ring, a cycloalkyl group, an aryl group, an oxime, an imine, a hydrazone a bridged cycloalkyl group,

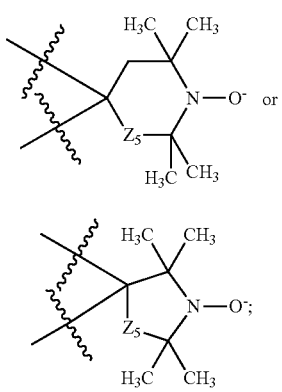

$V_6$ is:

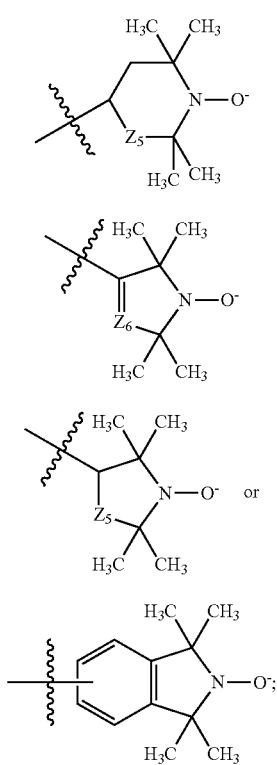

$U_3$ is an oxygen, sulfur or —N($R_a$)$R_i$;
$V_5$ is —NO or —$NO_2$ (i.e. an oxidized nitrogen);
$R_a$ is a lone pair of electrons, a hydrogen or an alkyl group;
$R_i$ is a hydrogen, an alkyl, an aryl, an alkylcarboxylic acid, an arylcarboxylic acid, an alkylcarboxylic ester, an arylcarboxylic ester, an alkylcarboxamido, an arylcarboxamido, an alkylaryl, an alkylsulfinyl, an alkylsulfonyl, an alkylsulfonyloxy, an arylsulfinyl, an arylsulfonyl, an arylsulphonyloxy, a sulfonamido, a carboxamido, a carboxylic ester, an aminoalkyl, an aminoaryl, a bond to an adjacent atom creating a double bond to that atom or —($N_2O_2$-).$M_1^+$, wherein $M_1^+$ is an organic or inorganic cation;

$R_j$ and $R_k$ are independently selected from an alkyl group, an aryl group, or $R_j$ and $R_k$ taken together with the nitrogen atom to which they are attached are a heterocyclic ring; and with the proviso that both Rn and Rm-Rn taken together cannot be a hydrogen.

2. A method for treating glaucoma, elevated ocular pressure or ocular hypertension in a patient in need thereof comprising administering to the patient an effective amount of a composition comprising a pharmaceutically acceptable carrier and a nitric oxide enhancing arbaprostil-compound of Formula (XXXV), a nitric oxide enhancing alprostadil or $PGE_1$ compound of Formula (XXXVI), a nitric oxide enhancing bimatoprost-compound of Formula (XXXVII), a nitric oxide enhancing carboprost compound of Formula (XXXVIII), a nitric oxide enhancing cloprostenol compound of Formula (XXXIX), a nitric oxide enhancing dimoxaprost compound of Formula (XL), a nitric oxide enhancing dinoprost compound of Formula (XLI), a nitric oxide enhancing enprostil compound of Formula (XLII), a nitric oxide enhancing enisoprost compound of Formula (XLIII), a nitric oxide enhancing fenprostalene compound of Formula (XLIV), a nitric oxide enhancing froxiprost compound of Formula (XLV), a nitric oxide enhancing gemeprost compound of Formula (XLVI), a nitric oxide enhancing latanoprost compound of Formula (XLVII), a nitric oxide enhancing meteneprost compound of Formula (XLVIII), a nitric oxide enhancing mexiprostil compound of Formula (XLIX), a nitric oxide enhancing misoprostol compound of Formula (L), a nitric oxide enhancing misoprostol acid compound of Formula (LI), a nitric oxide enhancing nocloprost compound of Formula (LII), a nitric oxide enhancing ONO 373 compound of Formula (LIII), a nitric oxide enhancing ornoprostil compound of Formula (LIV), a nitric oxide enhancing prostalene compound of Formula (LV), a nitric oxide enhancing $PGE_2$ compound of Formula (LVI), a nitric oxide enhancing $PGF_1$ compound of Formula (LVII), a nitric oxide enhancing $PGF_{2\alpha}$ compound of Formula (LVIII), a nitric oxide enhancing rioprostil compound of Formula (LIX), a nitric oxide enhancing rosaprostol compound of Formula (LX), a nitric oxide enhancing remiprostol compound of Formula (LXI), a nitric oxide enhancing sulprostone compound of Formula (LXII), a nitric oxide enhancing tafluprost compound of Formula (LXIII), a nitric oxide enhancing travoprost compound of Formula (LXIV), a nitric oxide enhancing trimoprostil compound of Formula (LXV), a nitric oxide enhancing tiprostanide compound of Formula (LXVI), a nitric oxide enhancing unoprostone compound of Formula (LXVII), and pharmaceutically acceptable salts thereof;

wherein the compound of Formula (XXXV) is:

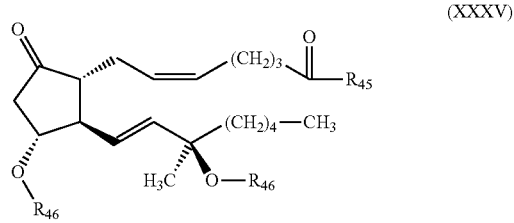

wherein the compound of Formula (XXXVI) is:

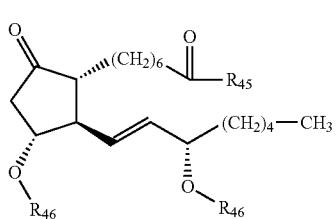
(XXXVI)

wherein the compound of Formula (XXXVII) is:

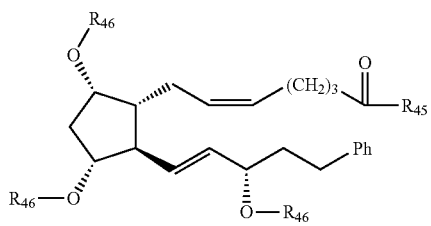
(XXXVII)

wherein the compound of Formula (XXXVIII) is:

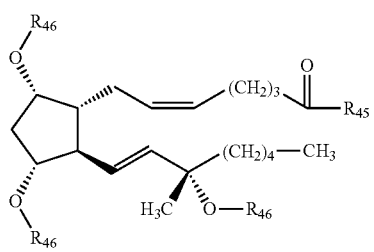
(XXXVIII)

wherein the compound of Formula (XXXIX) is:

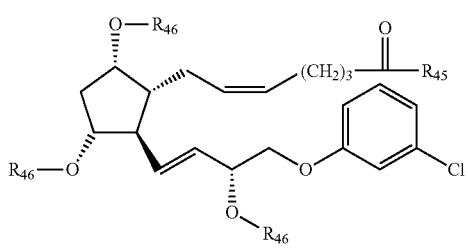
(XXXIX)

wherein the compound of Formula (XL) is:

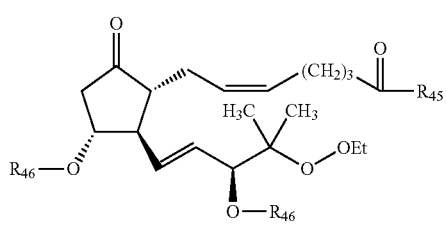
(XL)

wherein the compound of Formula (XLI) is:

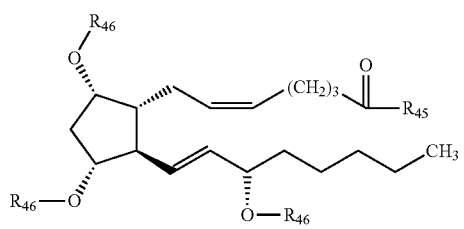
(XLI)

wherein the compound of Formula (XLII) is:

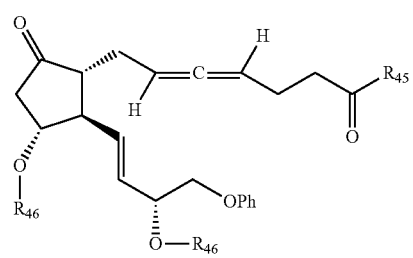
(XLII)

wherein the compound of Formula (XLIII) is:

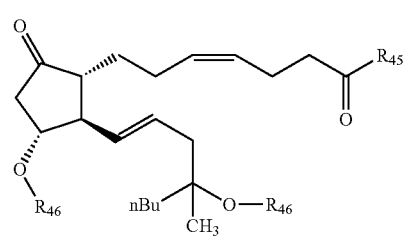
(XLIII)

wherein the compound of Formula (XLIV) is:

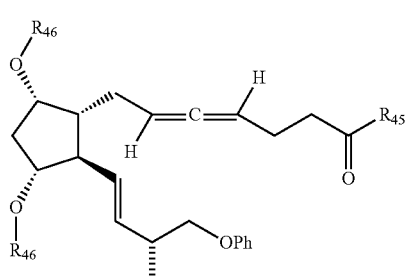
(XLIV)

wherein the compound of Formula (XLV) is:

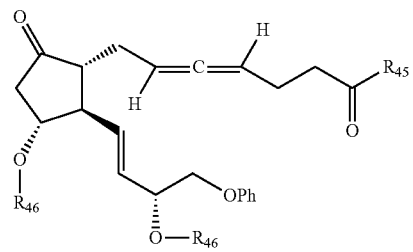
(XLV)

wherein the compound of Formula (XLVI) is:

(XLVI)

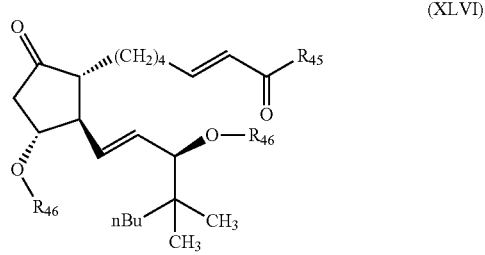

wherein the compound of Formula (XLVII) is:

(XLVII)

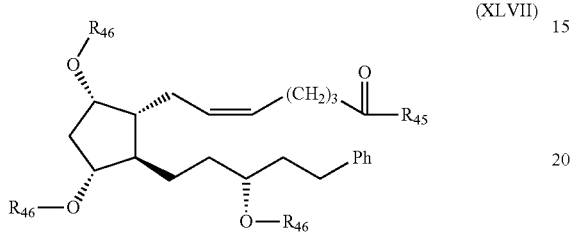

wherein the compound of Formula (XLVIII) is:

(XLVIII)

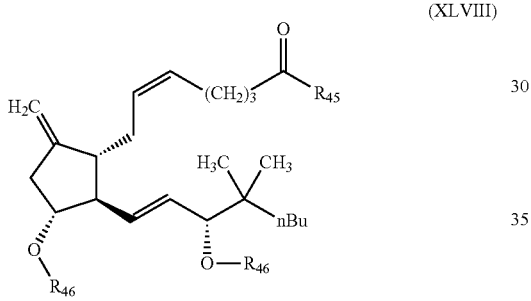

wherein the compound of Formula (XLIX) is:

(XLIX)

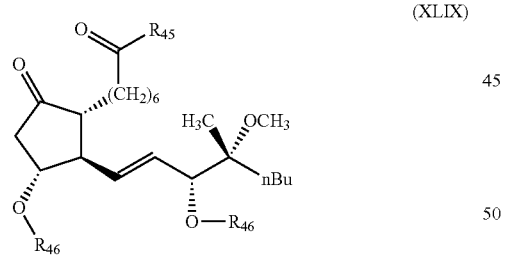

wherein the compound of Formula (L) is:

(L)

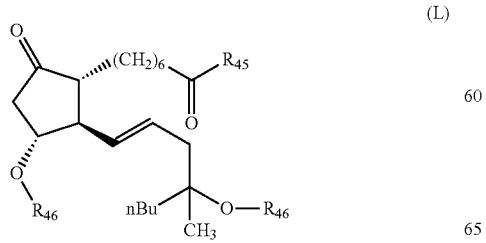

wherein the compound of Formula (LI) is:

(LI)

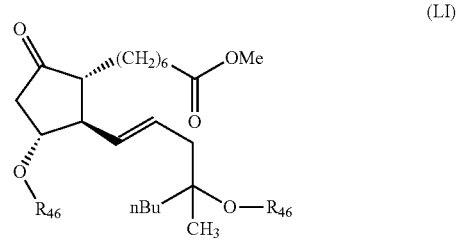

wherein the compound of Formula (LII) is:

(LII)

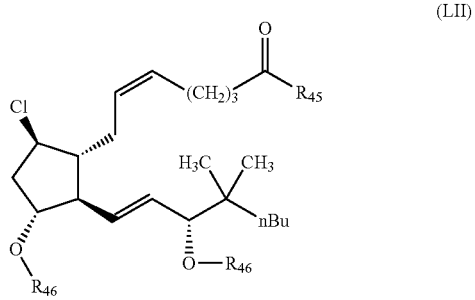

wherein the compound of Formula (LIII) is:

(LIII)

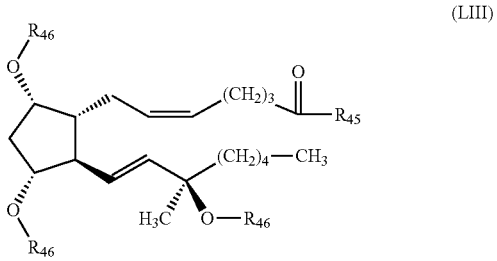

wherein the compound of Formula (LIV) is:

(LIV)

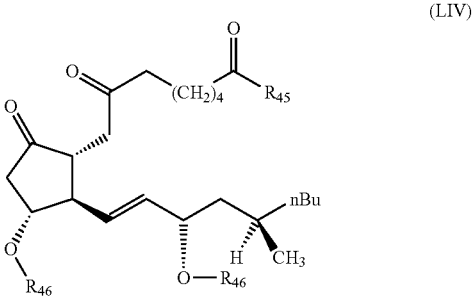

wherein the compound of Formula (LV) is:

(LV)

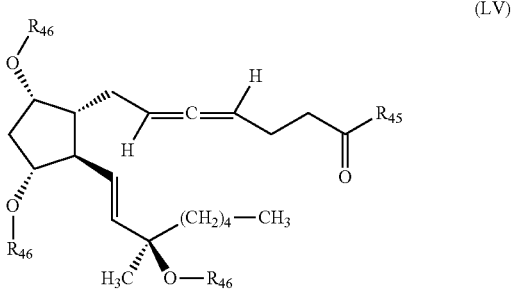

wherein the compound of Formula (LVI) is:

(LVI)

wherein the compound of Formula (LVII) is:

(LVII)

wherein the compound of Formula (LVIII) is:

(LVIII)

wherein the compound of Formula (LIX) is:

(LIX)

wherein the compound of Formula (LX) is:

(L)

wherein the compound of Formula (LXI) is:

(LXI)

wherein the compound of Formula (LXII) is:

(LXII)

wherein the compound of Formula (LXIII) is:

(LXIII)

wherein the compound of Formula (LXIV) is:

(LXIV)

wherein the compound of Formula (LXV) is:

(LXV)

wherein the compound of Formula (LXVI) is:

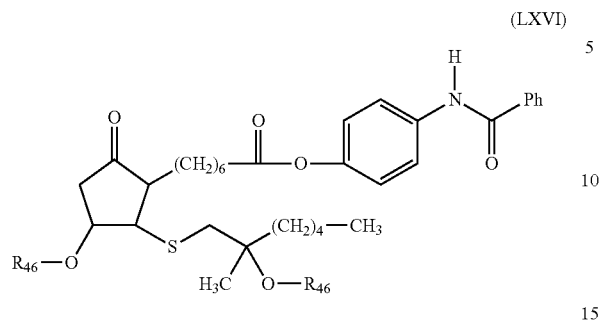
(LXVI)

wherein the compound of Formula (LXVII) is:

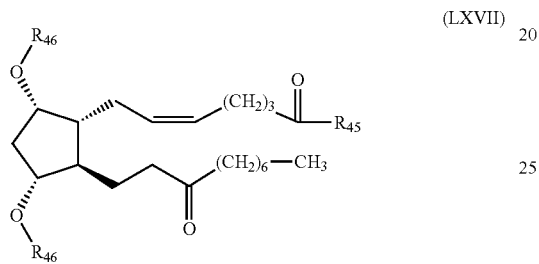
(LXVII)

wherein:
nBu is the lower alkyl group $CH_3-CH_2-CH_2-CH_2-$;
OMe is the alkoxy group $-O-CH_3$;
OEt is the alkoxy group $-OCH_2-CH_3$;
OPh is the alkoxy group $-OC_6H_5$;
Ph is a aryl group $-C_6H_5$;
$R_{45}$ is:

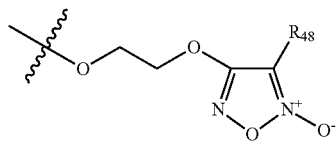
(1)

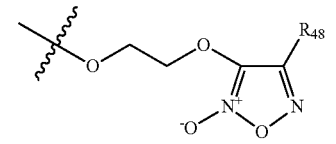
(2)

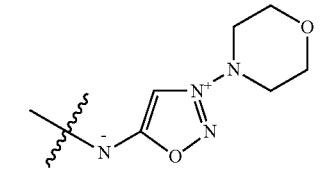
(3)

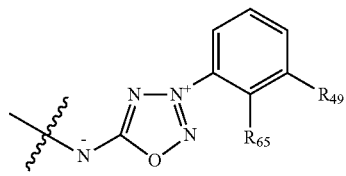
(4)

$-OH$; (5)

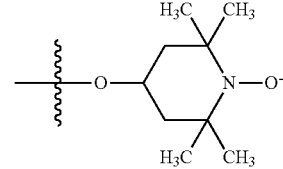
(6)

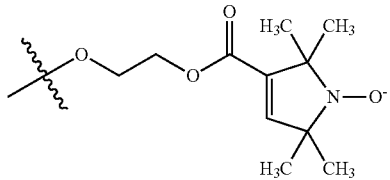
(7)

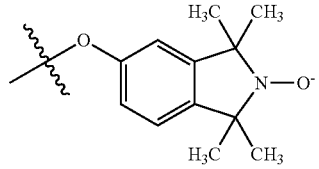
(8)

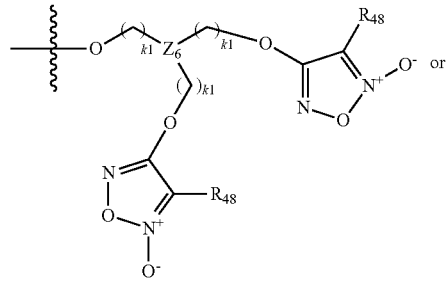
(9)

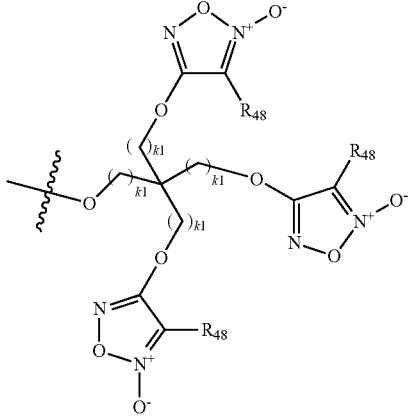
(10)

$R_{48}$ is $-S(O)_2-C_6H_5$; $-CN$, $-C(O)-NH_2$ or $-C(O)OCH_3$, and $R_{49}$ is a hydrogen or chlorine;

$R_{65}$ is a hydrogen or a methyl group;

$k_1$ is an integer from 1 to 3;

$Z_6$ is CH or nitrogen;

R$_{46}$ is:
(1) 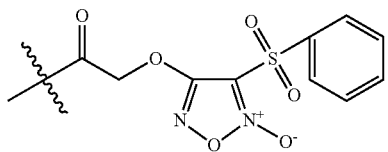
(2) 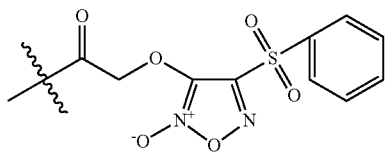
(3) 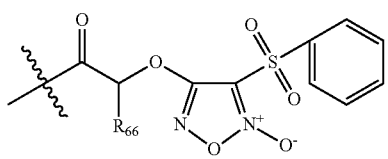
(4) 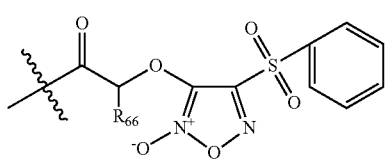
(5) 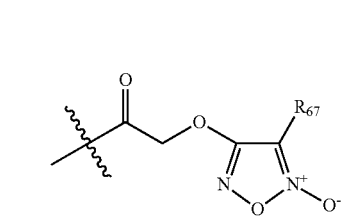
(6) 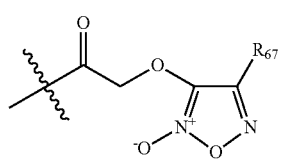
(7) 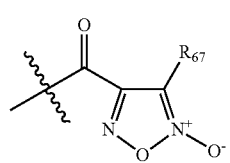
(8) 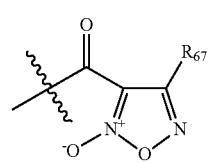
(9) 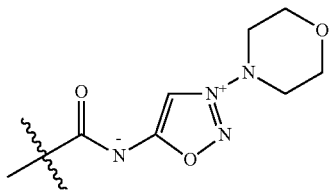
(10) 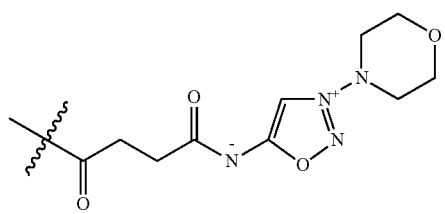
(11) 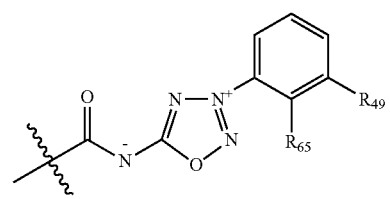
(12) 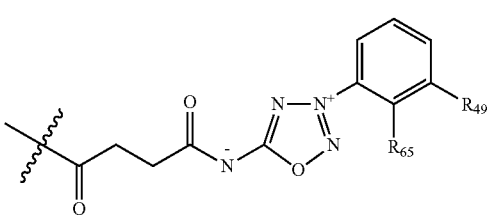
(13) 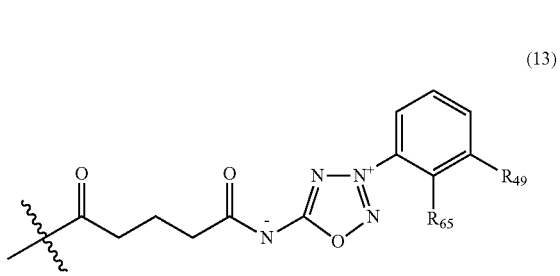
(14) H;
(15) 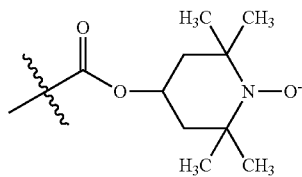
(16) 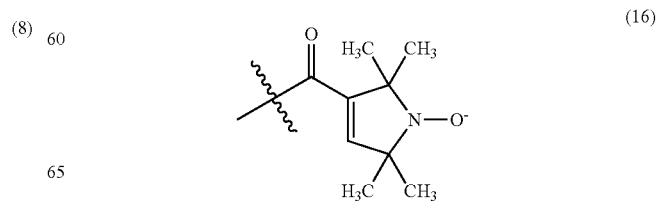

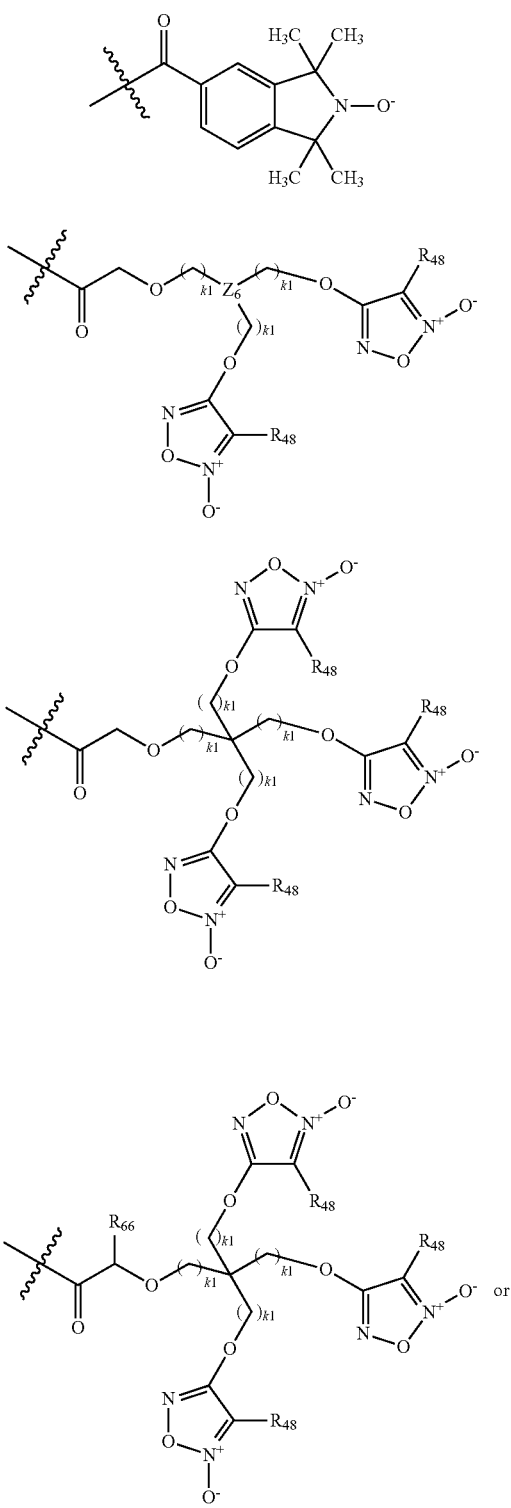

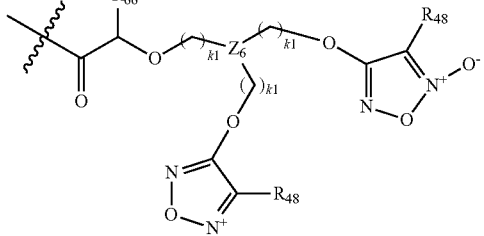

wherein:
$R_{66}$ is $-(CH_2)_2-O-C(O)-CH_3$ or $-(CH_2)_2-NH-C(O)-CH_3$; and
$R_{67}$ is $-CN$, $-C(O)-NH_2$ or $-C(O)-OCH_3$;
with the proviso that in the compounds of Formula (XXXV) to (LXVII) when $R_{45}$ is $-OH$ at least one of $R_{46}$ cannot be a hydrogen; or when each of $R_{46}$ is a hydrogen, $R_{45}$ cannot be $-OH$.

3. The method of claim 1 or 2, further comprising administering (i) at least one therapeutic agent; (ii) at least one nitric oxide enhancing compound; or (iii) at least one therapeutic agent and at least one nitric oxide enhancing compound.

4. The method of claim 3, wherein the therapeutic agent is an aldosterone antagonist, an α-adrenergic receptor agonist, an α-adrenergic receptor antagonist, a β-adrenergic agonist, an antidiabetic compound, an antimicrobial compound, an anti-hyperlipidemic drug, an angiotensin II antagonist, an angiotensin-converting enzyme inhibitor, an antioxidant, an antithrombotic and vasodilator drug, a β-adrenergic antagonist, a calcium channel blocker, a carbonic anhydrase inhibitor, a diuretic, an endothelin antagonist, a hydralazine compound, a $H_2$ receptor antagonist, a neutral endopeptidase inhibitor, a nonsteroidal antiinflammatory compound, a phosphodiesterase inhibitor, a potassium channel blocker, a platelet reducing agent, a prostaglandin, a proton pump inhibitor, a renin inhibitor, a selective cyclooxygenase-2 inhibitor, a steroid, a compound used for the treatment of glaucoma or a combinations of two or more thereof.

5. The method of claim 4, wherein the therapeutic agent is at least one compound selected from the group consisting of an α-adrenergic receptor antagonist, a β-adrenergic agonist, an antimicrobial compound, a β-adrenergic antagonist, a calcium channel blocker, a carbonic anhydrase inhibitor, a nonsteroidal antiinflammatory compound (NSAID), a phosphodiesterase inhibitor, a potassium channel blocker, a prostaglandin, a proton pump inhibitor, a selective cyclooxygenase-2 (COX-2) inhibitor and a steroid.

6. The method of claim 3, wherein the nitric oxide enhancing compound is selected from the group consisting of a S-nitrosothiol, a nitrite, a nitrate, a S-nitrothiol, a sydnonimine, a NONOate, a N-nitrosoamine, a N-hydroxyl nitrosamine, a nitrosimine, a diazetine dioxide, an oxatriazole 5-imine, an oxime, a hydroxylamine, a N-hydroxyguanidine, a hydroxyurea, a furoxan or a nitroxide.

\* \* \* \* \*